(12) United States Patent
Thomas et al.

(10) Patent No.: US 11,407,812 B2
(45) Date of Patent: Aug. 9, 2022

(54) TARGETED EXPRESSION OF CHLORIDE CHANNELS AND METHODS OF USE THEREOF

(71) Applicant: GOLEINI INC., Burlingame, CA (US)

(72) Inventors: Griffith Roger Thomas, Burlingame, CA (US); Shawnalea Jimee Frazier, San Anselmo, CA (US)

(73) Assignee: GOLEINI INC., Burlingame, CA (US)

( * ) Notice: Subject to any disclaimer, the term of this patent is extended or adjusted under 35 U.S.C. 154(b) by 432 days.

(21) Appl. No.: 15/764,733

(22) PCT Filed: Sep. 28, 2016

(86) PCT No.: PCT/US2016/054199
§ 371 (c)(1),
(2) Date: Mar. 29, 2018

(87) PCT Pub. No.: WO2017/058926
PCT Pub. Date: Apr. 6, 2017

(65) Prior Publication Data

US 2019/0010210 A1    Jan. 10, 2019

Related U.S. Application Data

(60) Provisional application No. 62/378,509, filed on Aug. 23, 2016, provisional application No. 62/303,907, filed on Mar. 4, 2016, provisional application No. 62/235,920, filed on Oct. 1, 2015, provisional application No. 62/235,914, filed on Oct. 1, 2015.

(51) Int. Cl.
| | |
|---|---|
| *C07K 14/705* | (2006.01) |
| *A61P 25/00* | (2006.01) |
| *A61P 29/00* | (2006.01) |
| *A61K 45/06* | (2006.01) |
| *C12N 15/86* | (2006.01) |
| *A61K 48/00* | (2006.01) |

(52) U.S. Cl.
CPC ........ *C07K 14/70571* (2013.01); *A61K 45/06* (2013.01); *A61P 25/00* (2018.01); *A61P 29/00* (2018.01); *C07K 14/705* (2013.01); *C12N 15/86* (2013.01); *A61K 48/00* (2013.01); *C12N 2710/16143* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 3,644,643 A * | 2/1972 | Krantz | A61K 31/195 514/561 |
| 4,559,157 A | 12/1985 | Smith et al. | |
| 4,608,392 A | 8/1986 | Jacquet et al. | |
| 4,820,508 A | 4/1989 | Wortzman | |
| 4,873,192 A | 10/1989 | Kunkel | |
| 4,992,478 A | 2/1991 | Geria | |
| 5,527,703 A | 6/1996 | Cully et al. | |
| 6,156,303 A | 12/2000 | Russell et al. | |
| 8,945,918 B2 | 2/2015 | Chen | |
| 8,957,036 B2 | 2/2015 | Cascio et al. | |
| 2003/0032608 A1* | 2/2003 | Feder | C07K 14/705 514/44 A |
| 2006/0088913 A1 | 4/2006 | Wallace et al. | |
| 2008/0138364 A1 | 6/2008 | Aoki et al. | |
| 2008/0289058 A1 | 11/2008 | Cascio et al. | |
| 2010/0069467 A1 | 3/2010 | Boye et al. | |
| 2010/0240739 A1* | 9/2010 | Barkats | A61P 37/02 514/44 R |
| 2011/0086389 A1 | 4/2011 | Dolly et al. | |
| 2011/0213017 A1 | 9/2011 | Cascio et al. | |
| 2012/0282242 A1 | 11/2012 | Abreu | |
| 2012/0289534 A1 | 11/2012 | Pergolizzi et al. | |
| 2013/0184318 A1 | 7/2013 | Russell et al. | |
| 2015/0217133 A1 | 8/2015 | Angeley et al. | |
| 2017/0081384 A1 | 3/2017 | Cascio et al. | |

FOREIGN PATENT DOCUMENTS

| | | |
|---|---|---|
| WO | 2008143875 A1 | 11/2008 |
| WO | 2010042799 A2 | 4/2010 |
| WO | 2014018423 A2 | 1/2014 |
| WO | 2014020149 A1 | 2/2014 |
| WO | 2014093251 A1 | 6/2014 |
| WO | 2015106005 A1 | 7/2015 |

(Continued)

OTHER PUBLICATIONS

Raol et al. Enhancing GABAA Receptor α1 Subunit Levels in Hippocampal Dentate Gyrus Inhibits Epilepsy Development in an Animal Model of Temporal Lobe Epilepsy. The Journal of Neuroscience, 2006. 26(44):11342-11346.*
Shan et al. Asymmetric Contribution of α and β Subunits to the Activation of Heteromeric Glycine Receptors. Journal of Neurochemistry, 2003. 86:498-507.*
Borras, Terete. Advances in Glaucoma Treatment and Management: Gene Therapy. Investigative Ophthalmology & Visual Science, Special Issue, 2012. 53(5):2506-2510.*
Genbank Accession Nos. NM_000171.1, 2006. 2 pages.*
Genbank Accession No. NP_000162.1, 2006; 3 pages.*

(Continued)

*Primary Examiner* — James D Schultz
*Assistant Examiner* — Kimberly A Aron
(74) *Attorney, Agent, or Firm* — Viksnins Harris Padys Malen LLP

(57) ABSTRACT

Certain embodiments of the invention provide a method of treating an excitable cell-related disease or condition in a mammal in need thereof, comprising administering to the mammal an effective amount of a vector comprising an expression cassette, wherein the expression cassette comprises a promoter operably linked to a nucleic acid encoding a subunit of a multimeric ion channel.

27 Claims, 14 Drawing Sheets

Specification includes a Sequence Listing.

(56) References Cited

FOREIGN PATENT DOCUMENTS

| WO | 2015149033 A1 | 10/2015 |
|---|---|---|
| WO | 2016055437 A1 | 4/2016 |
| WO | 2017049252 A1 | 3/2017 |
| WO | 2017072498 A1 | 5/2017 |
| WO | 2017184879 A1 | 10/2017 |

OTHER PUBLICATIONS

Ishibashi et al. cDNA Microarray Analysis of Gene Expression Changes Induced by Dexamethasone in Cultured Human Trabecular Meshwork Cells. Investigative Ophthalmology & Visual Sciences, 2002. 43(12):3691-3697.*

Dalziel et al. Mutating the Highly Conserved Second Membrane-Spanning Region 9' Leucine Residue in the α1 or β1 Subunit Produces Subunit-Specific Changes in the Function of Human α1β1 γ-Aminobutyric AcidA Receptors. Molecular Pharmacology, 2000. 57:875-882.*

Becker et al. Disease-Specific Human Glycine Receptor α1 Subunit Causes Hyperekplexia Phenotype and Impaired Glycine-and GABAA-Receptor Transmission in Transgenic Mice. The Journal of Neuroscience, 2002.*

UniProtKB Entry P23415, priority to 2006. 7 pages.*

Genbank Accession No. BC114947. Priority to 2008. 4 pages.*

Taleb et al., Expression of the Human Glycine Receptor alpha1 Subunit In Xenopus Oocytes: Apparent Affinities of Agonists Increase at High Receptor Density. The EMBO Journal, 1994. 13(6) 1318-1324.*

Scott et al. Correlating Structural and Energetic Changes in Glycine Receptor Activation. The Journal of Biological Chemistry, Feb. 2015. 290(9): 5621-5634.*

Akagi, H , et al., "Functional properties of strychnine-sensitive glycine receptors expressed in Xenopus oocytes injected with a single mRNA", Neurosci Res 11(1), 28-40 (1991).

Cynober, L , "Plasma amino acid levels with a note on membrane transport: characteristics, regulation, and metabolic significance", Nutrition 18(9), 761-766 (2002).

Davies, I , et al., "Measurements of plasma zinc", J Clin Path 21, 359-365 (1968).

Frazier, S , et al., "Optimization of the GluCI/IVM Neuronal Silencing Tool via Protein Engineering", Thesis In Partial Fulfillment of the Requirements for the Degree of Doctor of Philosophy, California Institute of Technology, 171 pages (2012).

Gonzalez, P , et al., "Expression Analysis of the Matrix GLA Protein and VE-Cadherin Gene Promoters in the Outflow Pathway.", Invest Ophthalmol Vis Sci 45, 1389-1395 (2004).

Goss, J R , et al., "HSV Delivery of a Ligand-regulated Endogenous Ion Channel Gene to Sensory Neurons Results in Pain Control Following Channel Activation", Molecular Therapy 19(3), 500-506 (2010).

Grant, S , et al., "Determination of d-serine and related neuroactive amino acids in human plasma by high-performance liquid chromatography with fluorimetric detection", J Chromatogr B Analyt Technol Biomed Life Sci 844(2), 278-282 (2006).

Griffon, N , et al., "Molecular determinants of glycine receptor subunit assembly", EMBO J 18(17), 4711-4721 (1999).

Hahn, R , "Dose-dependent half-life of glycine", Urol Res 21(4), 289-291 (1993).

Han, N , et al., "Comparison of taurine- and glycine-induced conformational changes in the M2-M3 domain of the glycine receptor", J Biol Chem 279(19), 19559-19565 (2004).

Jensen, A , et al., "Functional characterisation of the human alpha1 glycine receptor in a fluorescence-based membrane potential assay", Biochemical Pharmacology 67(9), 1789-1799 (2004).

Kirson, D , et al., "Positive allosteric modulators differentially affect full versus partial agonist activation of the glycine receptor", JPET 342(1), 61-70 (2012).

Kugler, S , et al., "Human synapsin 1 gene promoter confers highly neuron-specific long-term transgene expression from an adenoviral vector in the adult rat brain depending on the transduced area", Gene Therapy 10, 337-347 (2003).

Kumamoto, E , et al., "Glycine current in rat septal cholinergic neuron in culture: monophasic positive modulation by Zn2+", J Neurophysiol 76(1), 227-241 (1996).

Langlhofer, G , et al., "The Intracellular Loop of the Glycine Receptor: It's not all about the Size", Frontiers in Molecular Neuroscience 9(41), 14 pages (2016).

Laube, B , et al., "Modulation by zinc ions of native rat and recombinant human inhibitory glycine receptors", J Physiol 483(Pt3), 613-619 (1995).

Malosio, M , et al., "Alternative Splicing Generates Two Variants of the alpha 1 Subunit of the Inhibitory Glycine Recepto", Journal of Biological Chemistry 266(4), 2048-2053 (1991).

Mori, M , et al., "Beta-alanine and taurine as endogenous agonists at glycine receptors in rat hippocampus in vitro", J Physiol 539(1), 191-200 (2002).

Pan, Z H , et al., "Agonist-induced closure of constitutively open γ-aminobutyric acid channels with mutated M2 domains", Proc Natl Acad Sci USA 94, 6490-6495 (1997).

Patent Cooperation Treaty , International Searching Authority, Search Report and Written Opinion for PCT/US2016/054199, 17 pages, dated Feb. 1, 2017.

Psychogios, N , et al., "The human serum metabolome", PLoS One 6(2), e16957 (2011).

Rajendra, S , et al., "The glycine receptor", Pharmacol Ther 73(2), 121-146 (1997).

Schmieden, V , et al., "Pharmacology of the Inhibitory Glycine receptor: Agonist and Antagonist Actions of Amino Acids and Piperidine Carboxylic Acid Compounds", Mol Pharmacol 48(4), 919-927 (1995).

Slimko, E , et al., "Selective Electrical Silencing of Mammalian Neurons In Vitro by the Use of Invertebrate Ligand-Gated Chloride Channels", J Neurosci 22(17), 7373-7379 (2002).

Sontheimer, H , et al., "Functional chloride channels by mammalian cell expression of rat glycine receptor subunit", Neuron 2(5), 1491-1497 (1989).

Towne, C , et al., "Recombinant adeno-associated virus serotype 6 (rAAV2/6)-mediated gene transfer to nociceptive neurons through different routes of delivery", Molecular Pain 5(1), 52 (2009).

Xue, H , et al., "A recombinant glycine receptor fragment forms homo-oligomers distinct from its GABA(A) counterpart", J Mol Biol 312(5), 915-920 (2001).

Decosterd, I , et al., "Spared nerve injury: an animal model of persistent peripheral neuropathic pain.", Pain 87(2), 149-158 (2000).

Durham, D. , et al., "Ion-exchange chromatography of free amino acids in human intraocular fluids", Clin Chem 17, 285-289 (1971).

El Hafidi, M , et al., "Is glycine effective against elevated blood pressure?", Curr Opin Clin Nutr Metab Care 9, 26-31 (2006).

Findlay, G , et al., "Transgenic Expression of a Mutant Glycine Receptor Decreases Alcohol Sensitivity of Mice", Journal of Pharmacology and Experimental Therapeutics 300(2), 526-534 (2002).

Frazier, S , et al., "An Engineered Glutamate-gated Chloride (GluCl) Channel for Sensitive, Consistent Neuronal Silencing by Ivermectin", Journal of Biological Chemistry 288(29), 21029-21042 (2013).

Froh, M. , et al., "Molecular evidence for a glycine-gated chloride channel in macrophages and leukocytes", Am J Physiol Gastrointest Liver Physiol 283, G856-G863 (2002).

Geigy Scientific Tables , 8th Rev edition, pp. 93 and 105. Edited by C. Lentner, West Cadwell, N.J.: Medical Education Div., Ciba-Geigy Corp. West Caldwell, New Jersey, 1984 (4 pages).

Glover, C. , et al., "Adenoviral-Mediated, High-Level, Cell-Specific Transgene Expression: A SYN1-WPRE Cassette Mediates Increased Transgene Expression with No Loss of Neuron Specificity", Molecular Therapy, 5(5), 509-516 (2002).

Harvey, R. , et al., "Glycine receptors containing the alpha4 subunit in the embryonic sympathetic nervous system, spinal cord and male genital ridge", Euro J Neurosci 12, 994-1001 (2000).

Heinze, L , et al., "Diversity of glycine receptors in the mouse retina: localization of the alpha4 subunit", J Comp Neurol 500, 693-707 (2007).

(56) References Cited

OTHER PUBLICATIONS

Islam, R , et al., "Ivermectin-activated, cation-permeable glycine receptors for the chemogenetic control of neuronal excitation", ACS Chem Neurosci, DOI: 10.1021/acschemneuro.6b00168 • Publication Date (Web): (Sep. 9, 2016).
Jiang, Z. , et al., "Nitric oxide synthase isoforms expression in fibroblasts isolated from human normal peritoneum and adhesion tissues", Fertil Steril 90, 769-774 (2008).
Liu, Y. , et al., "On the Dependency of Cellular Protein Levels on mRNA Abundance", Cell 165, 535-550 (2016).
Lynagh, T. , et al., "A glycine residue essential for high ivermectin sensitivity in Cys-loop ion channel receptors", International Journal for Parasitology 40, 1477-1481 (2010).
Lynagh, T , et al., "An Improved Ivermectin-activated Chloride Channel Receptor for Inhibiting Electrical Activity in Defined Neuronal Populations", Journal of Biological Chemistry 285 (20), 14890-14897 (2010).
Lynagh, T. , et al., "Molecular Determinants of Ivermectin Sensitivity at the Glycine Receptor Chloride Channel", The Journal of Biological Chemistry, 286(51), 43913-43924 (2011).
Lynch, J. , "Native glycine receptor subtypes and their physiological roles", Neuropharmacol 56, 303-309 (2009).
Matzenbach, B. , et al., "Structural analysis of mouse glycine receptor alpha subunit genes. Identification and chromosomal localization of a novel variant", J Biol Chem 269, 2607-2612 (1994).
Nathanson, J. , "Nitrovasodilators as a new class of ocular hypotensive agents", J Pharmacol Exp Ther. 260, 956-965 (1992).
Piechotta, K. , et al., "Localization of rat glycine receptor alpha1 and alpha2 subunit transcripts in the developing auditory brainstem", J Comp Neurol 438, 336-352 (2001).
Simon, J. , et al., "Analysis of the set of GABA(A) receptor genes in the human genome", J Biol Chem 279, 41422-35 (2004).
Vogel, C. , et al., "Insights into the regulation of protein abundance from proteomic and transcriptomic analyses", Nat Rev Genet 13(4), 227-232 (2012).
Yaksh, T , et al., "Peripheral release of substance P from primary afferents", Chapter 6, Proceedings from the Vth World Congress on Pain, Edited by Dubner R, Gebhart GF. Bond MR. Amsterdam: Elsevier, pp. 51-54 (1988).
Yim, P D , et al., "Novel expression of a functional glycine receptor chloride channel that attenuates contraction in airway smooth muscle.", The FASEB Journal 25(5), 1706-1717 (2011).
Zhang, G , et al., "Enhanced peripheral analgesia using virally mediated gene transfer of the mu-opioid receptor in mice.", Anesthesiology 108, 305-313 (2008).
Bode, A , et al., "The impact of human hyperekplexia mutations on glycine receptor structure and function", Molecular Brain 7(2), 1-12 (2014).
Du , et al., "Glycine Receptor mechanism elucidated by electron cyro-microscopy". Nature 526:224-229 (2015).
Kim, H , et al., "Divergence, demography and gene loss along the human lineage", Phil Trans R Soc B 365, 2451-2457 (2010).
Leacock, S , et al., "Structure/Function Studies of the α4 Subunit Reveal Evolutionary Loss of a GlyR Subtype Involved in Startle and Escape Responses", Front Mol Neurosci 11(23), 1-19 (2018).
Legendre , et al., "Desensitization of homomeric alpha1 glycine receptor increases with receptor density", Mol Pharmacol 62(4), 817-827 (2002).
Lorenzo, L , et al., "Gephyrin clusters are absent from small diameter primary afferent terminals despite the presence of GABA(A) receptors", J Neurosci. 34(24), 8300-8317 (2014).
NCBI , "GLRA4 glycine receptor alpha 4 (pseudogene) [ *Homo sapiens* (human) ]", https://www.ncbi.nlm.nih.gov/gene/441509, 11 pages (downloaded Dec. 14, 2021).
NIH National Cancer Institute , "pseudogene", https://www.cancer.gov/publications/dictionaries/genetics-dictionary/def/pseudogene, 1 page (downloaded Dec. 13, 2021).

Roberts, D , et al., "Egr3 stimulation of GABRA4 promoter activity as a mechanism for seizure-induced up-regulation of GABAA receptor alpha4 subunit expression", PNAS 102(33), 11894-11899 (2005).
Webb, T , et al., "Molecular pharmacology of the glycine receptor chloride channel", Curr Pharm Des. 3(23), 2350-2367 (2007).
Xiao , et al., "Identification of gene expression profile of dorsal root ganglion in the rat peripheral axotomy model of neuropathic pain", Proc Natl Acad Sci USA 99(12), 8360-8365 (2002).
Liton, P B , et al., "Specific Targeting of Gene Expression to a Subset of Human Trabecular Meshwork Cells Using the Chitinase 3-Like 1 Promoter.", Invest Ophthalmol Vis Sci 46, 183-190 (2005).
Liu, Y , et al., "Gene Expression Profile in Human Trabecular Meshwork From Patients With Primary Open-Angle Glaucoma ", Invest Ophthalmol Vis Sci 54(9), 6382-6389 (2013).
Mandel, R J , et al., "Recombinant adeno-associated viral vectors as therapeutic agents to treat neurological disorders.". Mol Ther 13(3), 463-83 (2006).
Mata, M , et al., "Applications of Gene Therapy to the Treatment of Chronic Pain.", Curr Gene Ther 8(1), 42-48 (2008) (NIH-PA Author Manuscript version, pp. 1-12).
McCarty, D , "Arthritis and Allied 20 Conditions, Chapter 4 Synovial Fluid", Edited by Koopman WJ. Baltimore: Williams and Wilkins, 81-102 (1997).
McNearney, T A , et al., "A peripheral neuroimmune link: glutamate agonists upregulate NMDA NR1 receptor mRNA and protein, vimentin, TNF-α, and RANTES in cultured human synoviocytes.", Am J Physiol Regul Integr Comp Physiol 298(3), R584-R598 (2010).
McNearney, T , et al., "Excitatory amino acid profiles of synovial fluid from patients with arthritis.", J Rheumatol 27(3), 739-745 (2000) (Author Manuscript version, pp. 1-13).
McNearney, T , et al., "Excitatory amino acids display compartmental disparity between plasma and synovial fluid in clinical arthropathies.", Int J Clin Exp Pathol 6(3), 492-497 (2013).
McNearney, T , et al., "Excitatory amino acids, TNF-alpha, and chemokine levels in synovial fluids of patients with active arthropathies.", Clin Exp Immunol 137(3), 621-627 (2004).
Meinkoth, J , et al., "Hybridization of nucleic acids immobilized on solid supports ", Anal Biochem 138(2), 267-284 (1984).
Meuli-Simmen, C , et al., "Gene expression along the cerebralspinal axis after regional gene delivery.", Hum Gene Ther 10, 2689-2700 (1999).
Meunier, A , et al., "Lentiviral-mediated targeted transgene expression in dorsal spinal cord glia: tool for the study of glial cell implication in mechanisms underlying chronic pain development.", J Neurosci Methods 167(2), 148-159 (2008).
Milligan, E D , et al., "Repeated intrathecal injections of plasmid DNA encoding interleukin-10 produce prolonged reversal of neuropathic pain.", Pain 126(1-3), 294-308 (2006).
Miyazawa, A , et al., "Structure and gating mechanism of the acetylcholine receptor pore.", Nature 423(6943), 949-955 (2003).
Myers, E , et al., "Optimal alignments in linear space", Cabios 4(1), 11-17 (1988).
Nathwani, A C , et al., "Long-term safety and efficacy following systemic administration of a self-complementary AAV vector encoding human FIX pseudotyped with serotype 5 and 8 capsid proteins.", Mol Ther 19(5), 876-885 (2011).
Nathwani, A C , et al., "Long-term safety and efficacy of factor IX gene therapy in hemophilia B.", N Engl J Med 371(21), 1994-2004 (2014) (NIH-PA Author Manuscript version, pp. 1-17).
Needleman, S , et al., "A General Method Applicable to the Search for Similarities in the Amino Acid Sequence of Two Proteins", J Mol Biol 48, 443-453 (1970).
Nordstrom, B L , et al., "Persistence and adherence with topical glaucoma therapy.", Am J Ophthalmol 140(4), 598.e1-598e.11 (2005).
Ogawa, K , et al., "Pharmacological characterization of lysophosphatidic acid-induced pain with clinically relevant neuropathic pain drugs.", Eur J Pain 16(7), 994-1004 (2012).
Ohtsuka, E , et al., "An Alternative Approach to Deoxyoligonucleotides as Hybridization Probes by Insertion of Deoxyinosine at Ambiguous Codon Positions", JBC 260(5), 2605-2608 (1985).

(56) References Cited

OTHER PUBLICATIONS

Palmer, J A , et al., "Development and optimization of herpes simplex virus vectors for multiple long-term gene delivery to the peripheral nervous system.", J Virol 74(12), 5604-5618 (2000).
Paylakhi, S H , et al., "Non-housekeeping genes expressed in human trabecular meshwork cell cultures.", Mol Vis 18, 241-254 (2012).
Pearson, W , et al., "Improved tools for biological sequence comparison", Proc Natl Acad Sci 85, 2444-2448 (1988).
Pearson, W , et al., "Using the FASTA program to search protein and DNA sequence databases.", Meth Mol Biol 24, 307-331 (1994).
Pezet, S , et al., "Reversal of neurochemical changes and pain-related behavior in a model of neuropathic pain using modified lentiviral vectors expressing GDNF.", Mol Ther 13(6), 1101-1109 (2006).
Rajendra, S , et al., "Mutation of an arginine residue in the human glycine receptor transforms beta-alanine and taurine from agonists into competitive antagonists.", Neuron 14(1), 169-175 (1995).
Ramage, L , et al., "NMDA receptor expression and activity in osteoarthritic human articular chondrocytes.", Osteoarthritis Cartilage 16, 1576-1584 (2008).
Richner, M , et al., "The spared nerve injury (SNI) model of induced mechanical allodynia in mice.", Journal of Visualized Experiments 18(54), pii 3092 (2011).
Rossolini, G , et al., "Use of deoxyinosine-containing primers vs degenerate primers for polymerase chain reaction based on ambiguous sequence information", Mol. Cell. Probes 8, 91-98 (1994).
Rupert, M , et al., "Evaluation of sacroiliac joint interventions: a systematic appraisal of the literature.", Pain Physician 12(2), 399-418 (2009).
Schrnieden, V , et al., "Mutation of glycine receptor subunit creates beta-alanine receptor responsive to GABA.", Science 262(5131), 256-258 (1993).
Schuelert, N , et al., "Grading of monosodium iodoacetate-induced osteoarthritis reveals a concentration-dependent sensitization of nociceptors in the knee joint of the rat.", Neuroscience Letters 465(2), 184-188 (2009).
Skerry, T M , et al., "Glutamate signalling in non-neuronal tissues ", Trends Pharmacol Sci 22(4), 174-181 (2001).
Smith, T , et al., "Comparison of biosequences", Adv Appl Math 2(4), 482-489 (1981).
Storek, B , et al., "Intrathecal long-term gene expression by self-complementary adeno-associated virus type 1 suitable for chronic pain studies in rats.", Mol Pain 2(4), 1-11 (2006).
Storek, B , et al., "Sensory neuron targeting by self-complementary AAV8 via lumbar puncture for chronic pain.", Proc Natl Acad Sci USA 105(3), 1055-1060 (2008).
Stumpff, F , et al., "Regulation of trabecular meshwork contractility.", Ophthalmologica 214(1), 33-53 (2000).
Stumpff, F , et al., "Stimulation of maxi-K channels in trabecular meshwork by tyrosine kinase inhibitors.", Invest Ophthalmol Vis Sci 40(7), 1404-1417 (1999).
Thompson, S A , et al., "Mutation at the putative GABAA ion-channel gate reveals changes in allosteric modulation.", Br J Pharmacol 127, 1349-1358 (1999).
Tomarev, S I , et al., "Gene Expression Profile of the Human Trabecular Meshwork: NEIBank Sequence Tag Analysis.", Invest Ophthalmol Vis Sci 44, 2588-2596 (2003).
Towne, C , et al., "Efficient transduction of non-human primate motor neurons after intramuscular delivery of recombinant AAV serotype 6.", Gene Therapy 17(1), 141-146 (2010).
Towne, C , et al., "Systemic AAV6 delivery mediating RNA interference against SOD1: neuromuscular transduction does not alter disease progression in fALS mice.", Mol Ther 16(6), 1018-1025 (2008).
Trang, L E , et al., "Plasma amino acids in rheumatoid arthritis.", Scand J Rheumatol 14, 393-402 (1985).
Turner , et al., "The potential exploitation of plant viral translational enhancers in biotechnology for increased gene axpression", Molecular Biotechnology, vol. 3, pp. 225-236, (1995).

Unwin, N , et al., "Nicotinic acetylcholine receptor at 9 A resolution.", J Mol Biol 229, 1101-1124 (1993).
Westlund, K N , et al., "Neural changes in acute arthritis in monkeys. II. Increased glutamate immunoreactivity in the medial articular nerve.", Brain Res Rev 17, 15-27 (1992).
Wilson, S P , et al., "Antihyperalgesic effects of infection with a preproenkephalin-encoding herpes virus.", Proc Natl Acad Sci USA 96, 3211-3216 (1999).
Wirtz , et al., "Expression Profile and Genome Location of cDNA Clones from an Infant Human Trabecular Meshwork Cell Library.", Invest Ophthalmol Vis Sci 43, 3698-3704 (2002).
Xu, Y , et al., "Efficiencies of Transgene Expression in Nociceptive Neurons Through Different Routes of Delivery of Adeno-Associated Viral Vectors.", Hum Gene Ther 14(9), 897-906 (2003).
Aalbers, C , et al., "Empty Capsids and Macrophage Inhibition/Depletion Increase rAAV Transgene Expression in Joints of Both Healthy and Arthritic Mice", Human Gene Therapy 28(2), 168-178 (2016).
Boissier, M , et al., "Synoviocyte Infection with Adeno-Associated Virus (AAV) Is Neutralized by Human Synovial Fluid from Arthritis Patients and Depends on AAV Serotype", Human Gene Ther 18, 525-535 (2007).
Gao, G , et al., "Novel adeno-associated viruses from rhesus monkeys as vectors for human gene therapy", PNAS 99(18), 11854-11859 (2002).
Genbank, Accession No. NM_000171.3, 4 pages 2015.
Genbank, Accession No. NM_001146040.1, 4 pages 2014.
Goodrich, L , et al., "scAAVIL-1ra dosing trial in a large animal model and validation of long-term expression with repeat administration for osteoarthritis therapy", Gene Therapy (2015) 22(7), 536-545 (2015) (Author Manuscript version, 20 pages).
Huttner, N , et al., "Genetic modifications of the adeno-associated virus type 2 capsid reduce the affinity and the neutralizing effects of human serum antibodies", Gene Therapy 10, 2139-2147 (2003).
Geiselbach, H , et al., "Single Expressed Glycine Receptor Domains Reconstitute Functional Ion Channels without Subunit-specific Desensitization Behavior", Journal of Biological Chemistry 289(42), 29135-29147 (2014).
Mingozzi, F , et al., "Prevalence and pharmacological modulation of humoral immunity to AAV vectors in gene transfer to synovial tissue", Gene Therapy 20, 417-424 (2012).
Rice, A , et al., "Animal models and the prediction of efficacy in clinical trials of analgesic drugs: A critical appraisal and call for uniform reporting standards", Pain 139, 243-247 (2008).
Royo, N , et al., "Specific AAV serotypes stably transduce primary hippocampal and cortical cultures with high efficiency and low toxicity", Brain research 1190, 15-22 (2007) (NIH-PA Author Manuscript version, 14 pages).
Velazquez, V , et al., "Effective Depletion of Pre-existing Anti-AAV Antibodies Requires Broad Immune Targeting", Mol Ther Meth Clin Dev 4, 159-168 (2017).
Altschul, S , et al., "Basic local alignment search tool", J Mol Biol 215, 403-410 (1990).
Altschul, S , et al., "Gapped BLAST and PSI-BLAST: a new generation of protein database search programs.", Nucleic Acids Res 25(17), 3389-3402 (1997).
Antunes Bras, J M , et al., "Herpes simplex virus 1-mediated transfer of preproenkephalin A in rat dorsal root ganglia.", J Neurochem 70(3), 1299-1303 (1998).
Appelgren, A , et al., "Neuropeptides in temporomandibular joints with rheumatoid arthritis: a clinical study.", Scand J Dent Res 99(6), 519-521 (1991).
Austin, P J , et al., "Chronic constriction of the sciatic nerve and pain hypersensitivity testing in rats.", Journal of Visualized Experiments 13(61), pii 3393 (2012).
Azeredo Da Silveira, S , et al., "Phosphorylation does not prompt, nor prevent, the formation of a-synuclein toxic species in a rat model of Parkinson's disease", Human Molecular Genetics 18(5), 872-887 (2009).
Batzer, M , et al., "Enhanced evolutionary PCR using oligonucleotides with inosine at the 3'-terminus", Nucl Acids Res 19(18), 5081 (1991).

(56) References Cited

OTHER PUBLICATIONS

Beckstein, O., et al., "A hydrophobic gate in an ion channel: the closed state of the nicotinic acetylcholine receptor.", Phys Biol 3(2), 147-159 (2006).
Borras, T., et al., "Gene therapy for glaucoma: treating a multifaceted, chronic disease.", Invest Ophthalmol Vis Sci 43(8), 2513-2518 (2002).
Bove, S E, et al., "Weight bearing as a measure of disease progression and efficacy of anti-inflammatory compounds in a model of monosodium iodoacetate-induced osteoarthritis.", Osteoarthritis and Cartilage 11(11), 821-830 (2003).
Buie, L K, et al., "Self-complementary AAV virus (scAAV) safe and long-term gene transfer in the trabecular meshwork of living rats and monkeys.", Invest Ophthalmol Vis Sci 51(1), 236-248 (2010).
Chang, Y, et al., "Allosteric activation mechanism of the alpha1 beta2gamma2 gamma-aminobutyric acid type A receptor revealed by mutation of the conserved M2 leucine.", Biophys J 77(5), 2542-2551 (1999).
Chang, Y, et al., "Substitutions of the Highly Conserved M2 Leucine Create Spontaneously Opening p1 γ-Aminobutyric Acid Receptors.", Mol Pharmacol 53(3), 511-523 (1998).
Chao, H, et al., "Several log increase in therapeutic transgene delivery by distinct adeno-associated viral serotype vectors.". Molecular Therapy 2(6), 619-623 (2000).
Chaplan, S R, et al., "Quantitative assessment of tactile allodynia in the rat paw.", J Neurosci Methods 53(1), 55-63 (1994).
Childers, M, et al., "Gene therapy prolongs survival and restores function in murine and canine models of myotubular myopathy.", Sci Transl Med 6(220), 220ra10 (2014).
Chung, J M, et al., "Segmental Spinal Nerve Ligation Model of Neuropathic Pain.", Methods Mol Med 99, 35-45 (2004).
Combe, R, et al., "The monosodium iodoacetate model of osteoarthritis: a model of chronic nociceptive pain in rats?", Neuroscience Letters 370(2-3), 236-240 (2004).
Corpei, F, et al., "Multiple sequence alignment with hierarchical clustering", Nucl Acids Res 16, 10881-10890 (1988).
Dixon, W J, "Efficient analysis of experimental observations.", Ann Rev Pharmacol Toxicol 20, 441-462 (1980).
Falk, D J, et al., "Comparative impact of AAV and enzyme replacement therapy on respiratory and cardiac function in adult Pompe mice.", Molecular Therapy— Methods & Clinical Development 2, 15007 (2015).
Fan, B J, et al., "Gene Expression Profiles of Human Trabecular Meshwork Cells Induced by Triamcinolone and Dexamethasone.", Invest Ophthalmol Vis Sci 49, 1886-1897 (2008).
Fehrenbacher, J C, et al., "Models of inflammation: Carrageenan- or Complete Freund's Adjuvant (CFA)-induced edema and hypersensitivity in the rat", Curr Protoc Pharmacol, Supplement 56, 5.4.1-5.4.7 (2012).
Fertuck, H C, et al., "In vivo recovery of muscle contraction after alpha-bungarotoxin binding.", J Cell Biol 66, 209-213 (1975).
Flood, S, et al., "Modulation of Interleukin-6 and Matrix Metalloproteinase 2 Expression in Human Fibroblast-like Synoviocytes by Functional Ionotropic Glutamate Receptors.", Arthritis Rheum 56, 2523-2534 (2007).
Franco, J A, "An in vitro adult mouse muscle-nerve preparation for studying the firing properties of muscle afferents.", J Vis Exp (91), e51948 (2014).
Fuchshofer, R, et al., "Gene expression profiling of TGFβ2- and/or BMP7-treated trabecular meshwork cells: Identification of Smad7 as a critical inhibitor of TGF-β2 signaling", Exp Eye Res 88, 1020-1032 (2009) (NIH-PA Author Manuscript version, pp. 1-28).
Gerometta, R, et al., "Steroid-Induced Ocular Hypertension in Normal Sheep", Investigative Ophthalmology & Visual Science 50(2), 669-673 (2008).

Ghadge, G D, et al., "CNS gene delivery by retrograde transport of recombinant replication-defective adenoviruses.", Gene Ther 2(2), 132-137 (1995).
Gonzalez, P, et al., "Characterization of Gene Expression in Human Trabecular Meshwork Using Single-Pass Sequencing of 1060 Clones.", Invest Ophthalmol Vis Sci 41, 3678-3693 (2000).
Gu, Y, et al., "The NMDA Type Glutamate Receptors Expressed by Primary Rat Osteoblasts Have the Same Electrophysiological Characteristics as Neuronal Receptors.", Calcif Tissue Intl 70(3), 194-203 (2002).
Hemmings, H C, et al., "Emerging molecular mechanisms of general anesthetic action.", Trends Pharmacol Sci 26(10), 503-510 (2005).
Higgins, D, et al., "Clustal: a package for performing multiple sequence alignment on a microcomputer", Gene 73, 237-244 (1988).
Higgins, D, et al., "Fast and sensitive multiple sequence alignments on a microcomputer.", Cabios 5(2), 151-153 (1989).
Hirzel, K, et al., "Hyperekplexia phenotype of glycine receptor alpha1 subunit mutant mice identifies Zn(2+) as an essential endogenous modulator of glycinergic neurotransmission.", Neuron 52(4), 679-690 (2006).
Huang, X, et al., "Parallelization of a local similarity algorithm.", Cabios 8(2), 155-165 (1992).
Inoue, M, et al., "Initiation of neuropathic pain requires lysophosphatidic acid receptor signaling.", Nat Med 10(7), 712-718 (2004).
Iyer, S M, et al., "Virally mediated optogenetic excitation and inhibition of pain in freely moving nontransgenic mice.", Nature Biotechnology 32(3), 274-278 (2014) (Advance Online version, pp. 1-5; and 3 pages of online methods).
Karlin, S, et al., "Applications and statistics for multiple high-scoring segments in molecular sequences", Proc Natl Acad Sci 90, 5873-5877 (1993).
Karlin, S, et al., "Methods for assessing the statistical significance of molecular sequence features by using general scoring schemes", Proc Natl Acad Sci 87(6), 2264-2268 (1990).
Keramidas, A, et al., "Cation-selective mutations in the M2 domain of the inhibitory glycine receptor channel reveal determinants of ion-charge selectivity.", J Gen Physiol 119, 393-410 (2002).
Kunkel, T, "Rapid and efficient site-specific mutagenesis without phenotypic selection", Proc Natl Acad Sci USA 82, 488-492 (1985).
Kunkel, T, et al., "Rapid and Efficient Site-Specific Mutagenesis without Phenotypic Selection", Meth Enzymol 154, 367-382 (1987).
Laketic-Ljubojevic, I, et al., "Functional characterization of N-methyl-D-aspartic acid-gated channels in bone cells.", Bone 25(6), 631-637 (1999).
Larsson, J, et al., "Concentration of substance P, neurokinin A, calcitonin gene-related peptide, neuropeptide Y and vasoactive intestinal polypeptide in synovial fluid from knee joints in patients suffering from rheumatoid arthritis.", Scand J Rheumatol 20(5), 326-335 (1991).
Lawand, N B, et al., "Amino acid release into the knee joint: key role in nociception and inflammation.", Pain 86(1-2), 69-74 (2000).
Lawand, N B, et al., "Excitatory amino acid receptor involvement in peripheral nociceptive transmission in rats.", Eur J Pharmacol 324, 169-177 (1997).
Lepple-Wienhues, A, et al., "Differential smooth muscle-like contractile properties of trabecular meshwork and ciliary muscle.", Exp Eye Res 53(1), 33-38 (1991).
Lin, C R, et al., "Electroporation for direct spinal gene transfer in rats.", Neurosci Lett 317(1), 1-4 (2002).
Liton, P B, et al., "Genome-wide expression profile of human trabecular meshwork cultured cells, nonglaucomatous and primary open angle glaucoma tissue.", Mol Vis 12, 774-790 (2006) (NIH-PA Author Manuscript version, pp. 1-31).

\* cited by examiner

FIGURES 1A-B
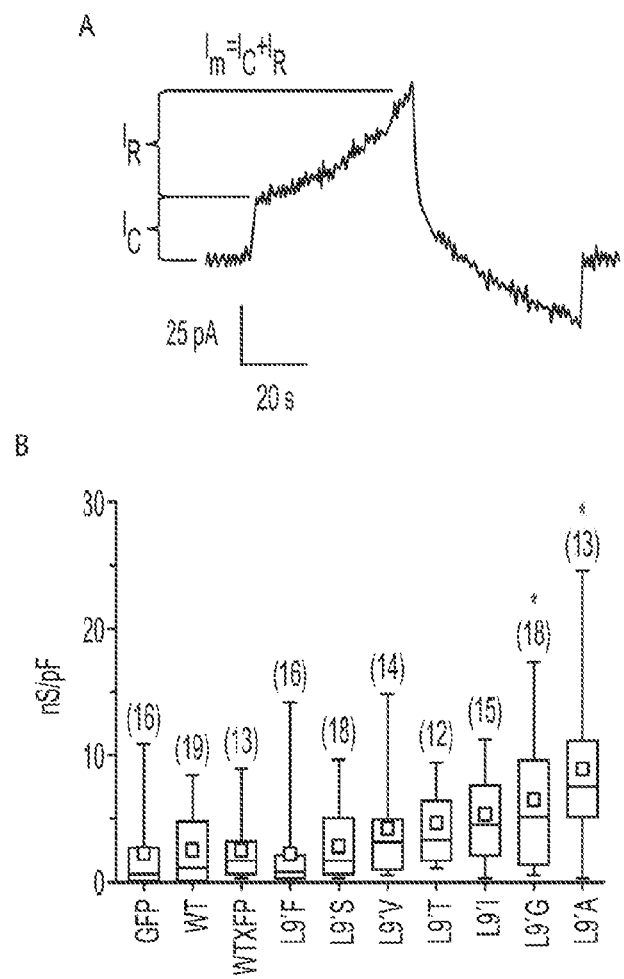
FIGURE 2A
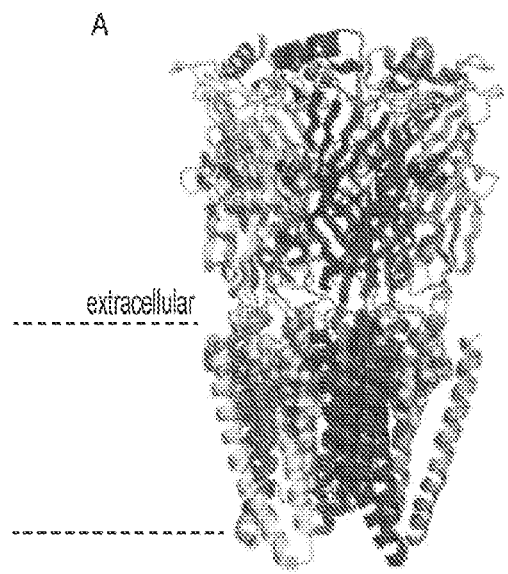

FIGURES 2B-F
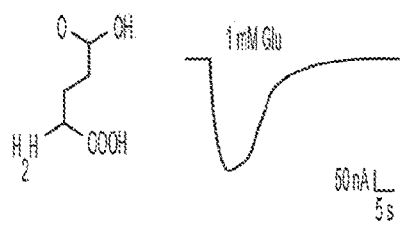
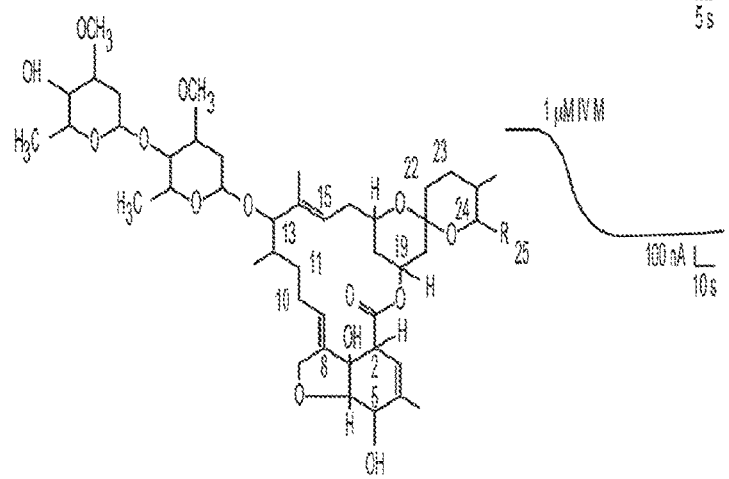
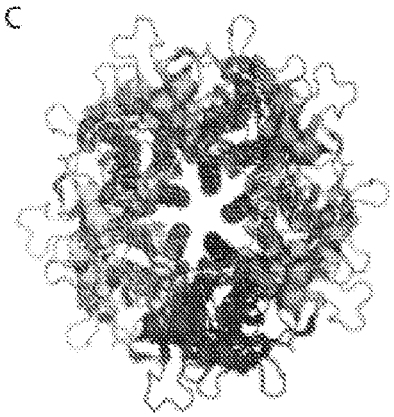
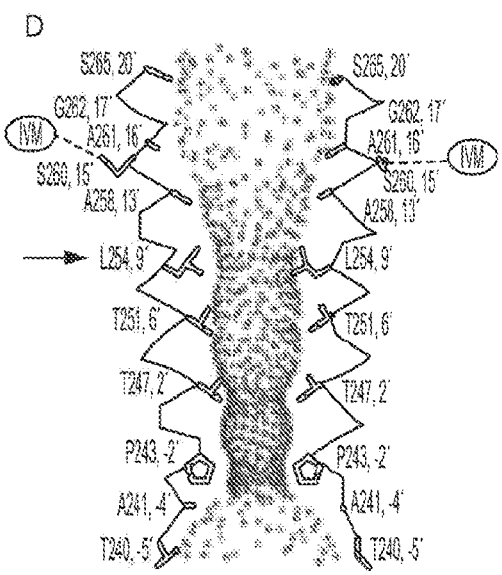
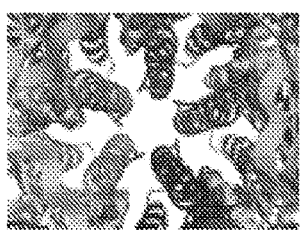

FIGURES 5A-B
A
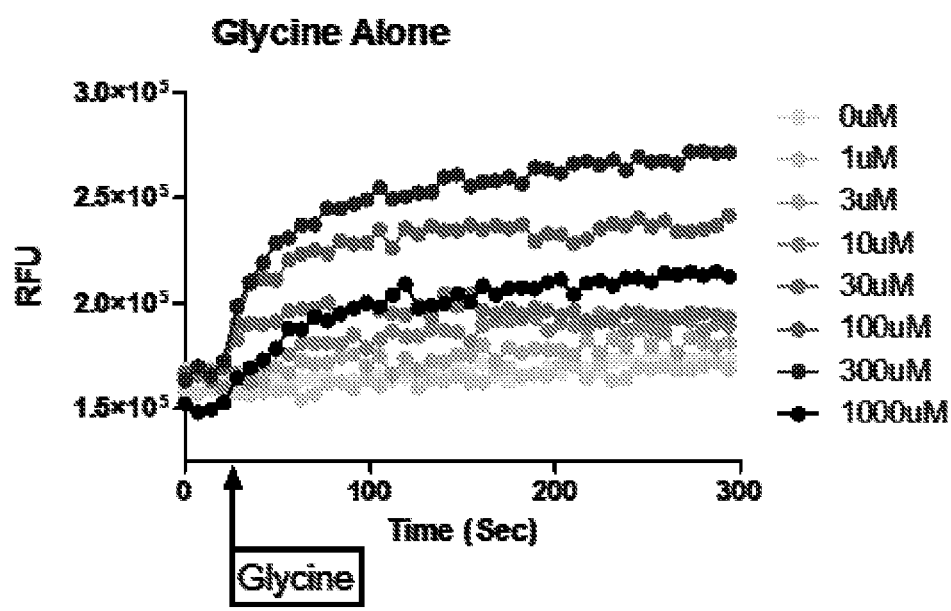
B
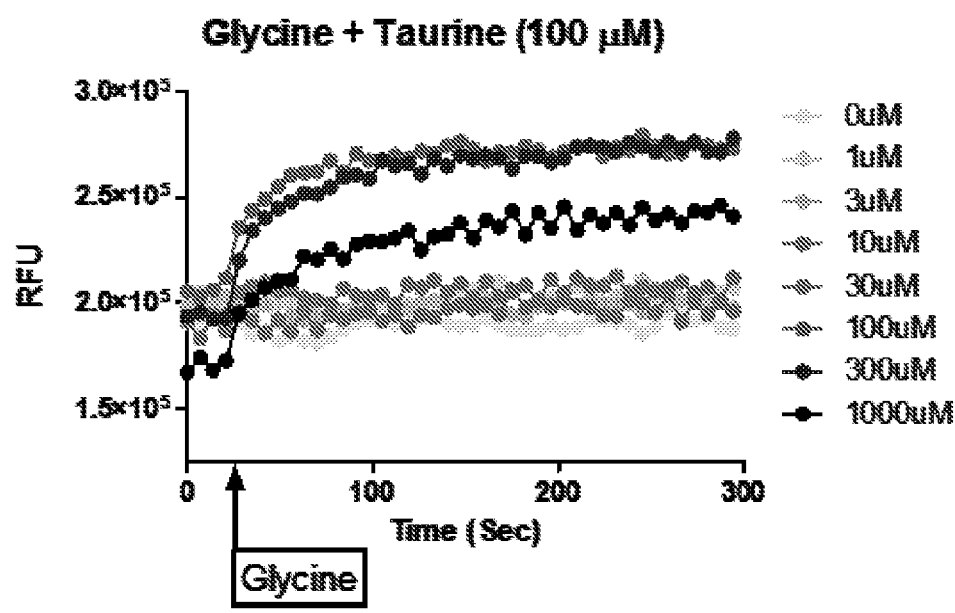

TARGETED EXPRESSION OF CHLORIDE CHANNELS AND METHODS OF USE THEREOF

RELATED APPLICATIONS

This application claims the benefit of priority of U.S. Provisional Application Ser. No. 62/235,914, filed on Oct. 1, 2015, U.S. Provisional Application Ser. No. 62/235,920, filed Oct. 1, 2015, U.S. Provisional Application Ser. No. 62/303,907, filed Mar. 4, 2016 and U.S. Provisional Application Ser. No. 62/378,509, filed on Aug. 23, 2016, which applications are incorporated by reference herein.

SEQUENCE LISTING

The instant application contains a Sequence Listing which has been submitted electronically in ASCII format and is hereby incorporated by reference in its entirety. Said ASCII copy, created on Nov. 9, 2016, is named 01989 007US1 SL.txt and is 15,948 bytes in size.

BACKGROUND

The potential to modulate the electrophysiological response of excitable cells (e.g., neurons and muscle cells) could potentially lead to treatment of neuromuscular conditions, pain, and other disorders associated with the activity of such cells. However, the administration of ligands that act on endogenous ion channels poses significant hurdles because of the potential for widespread side effects due to systemic delivery. Moreover, agents that act locally (such as silver or capsaicin) have unwanted side effects and can potentially cause permanent damage. Modulation of neuronal activity by expression of a ligand gated anionic channel has been shown previously wherein expression of a glutamate-gated chloride channel (GluCl), a nicotinicoid family receptor found in invertebrates, was used to silence neurons (Slimko E. et al. (2002) J Neurosci. 22(17): 7373-9). GluCl could be selectively activated by the addition of ivermectin, a high-potency ligand that has little or no effects on endogenous mammalian ion channels at low concentrations. For use in vertebrates, and particularly in human patients, however, this approach poses a risk of generating an immune response against such a foreign protein, leading to potential autoimmune disorders. To overcome the immune risk the human glycine-gated chloride channel (GlyR) was used in a similar fashion (Goss J R. et al. (2010) Molecular Therapy 19(3): 500-506; U.S. Pat. No. 8,957, 036). However, as was the case with GluCl, where the administration of ivermectin was needed to activate the channel, activation of the GlyR channel and subsequent physiological effect was accomplished by the administration of an agonist (glycine) either locally or systemically. Glycine has a short half-life in the body in the range of 26-245 min (Hahn R. (1993) Urol Res. 21: 289-91) so the maintenance of a physiological effect for the treatment of persistent or chronic conditions, such as chronic pain, ocular hypertension or spastic hypertonia by the methods and reagents described by U.S. Pat. No. 8,957,036 would necessitate either repeated injections or ingestion of large doses of glycine; or the development and subsequent repeated administration of selective long half-life synthetic agonists of the GlyR channel. Accordingly, additional methods and reagents for long-term modulation of the electrophysiological activity of excitable cells are needed. Additionally, new compositions and methods are needed to treat excitable cell-related diseases and conditions.

SUMMARY OF THE INVENTION

Accordingly, certain embodiments of the invention provide methods and reagents for modulating the electrophysiological activity of an excitable cell.

Certain embodiments of the invention provide a vector comprising an expression cassette, wherein the expression cassette comprises a promoter operably linked to a nucleic acid encoding a subunit of a multimeric chloride channel, for the modulation of a mammalian cell's electrophysiological activity (e.g., in vivo modulation).

Certain embodiments of the invention provide a method for the modulation (e.g., in vivo modulation) of a mammalian cell's electrophysiological activity comprising contacting the cell (e.g., in vivo) with a vector comprising an expression cassette comprising a promoter operably linked to a nucleic acid encoding a subunit of a multimeric chloride channel.

Certain embodiments of the invention provide the use of a vector comprising an expression cassette, wherein the expression cassette comprises a promoter operably linked to a nucleic acid encoding a subunit of a multimeric ion channel, to prepare a medicament for the modulation of a mammalian cell's electrophysiological activity (e.g., in vivo modulation).

Such a method may involve causing exogenous expression of a GlyR protein in an excitable cell of a mammal (e.g., a human). Thereafter, the excitable cell is exposed to endogenous glycine acting as an agonist of the GlyR protein. Modulation of the exogenous GlyR protein (an ion channel) in response to endogenous glycine modulates the electrophysiological activity of the excitable cell without the administration of exogenous agonists or allosteric modulators of the receptor.

In certain embodiments of the invention, a subunit of an ion channel may be modified so as to form a constitutively active channel, in which case exposure to an agonist is no longer necessary. The methods can be used to treat excitable cell-related diseases or conditions, such as pain, ocular hypertension and spasticity.

Accordingly, certain embodiments of the invention provide a vector comprising an expression cassette, wherein the expression cassette comprises a promoter operably linked to a nucleic acid encoding a subunit of a multimeric ion channel, for the prophylactic or therapeutic treatment of an excitable cell-related disease or condition.

Certain embodiments of the invention provide a method of treating an excitable cell-related disease or condition in a mammal in need thereof, comprising administering to the mammal (e.g., a human) an effective amount of a vector comprising an expression cassette, wherein the expression cassette comprises a promoter operably linked to a nucleic acid encoding a subunit of a multimeric ion channel.

Certain embodiments of the invention provide the use of a vector comprising an expression cassette, wherein the expression cassette comprises a promoter operably linked to a nucleic acid encoding a subunit of a multimeric ion channel, to prepare a medicament for the treatment of an excitable cell-related disease or condition in a mammal in need thereof.

Certain embodiments of the invention provide a vector comprising an expression cassette, wherein the expression cassette comprises a promoter operably linked to a nucleic acid encoding a subunit of a multimeric chloride channel for use in medical therapy.

Certain embodiments of the invention provide a pharmaceutical composition for the prophylactic or therapeutic treatment of an excitable cell-related disease or condition, comprising a vector comprising an expression cassette, wherein the expression cassette comprises a promoter operably linked to a nucleic acid encoding a subunit of a multimeric ion channel, and a pharmaceutically acceptable carrier.

Certain embodiments of the invention provide a combination of a) a vector comprising an expression cassette, wherein the expression cassette comprises a promoter operably linked to a nucleic acid encoding a subunit of a multimeric ion channel; and b) one or more other therapeutic agents; for the prophylactic or therapeutic treatment of an excitable cell-related disease or disorder.

Certain embodiments of the invention provide a kit comprising a vector comprising an expression cassette, wherein the expression cassette comprises a promoter operably linked to a nucleic acid encoding a subunit of a multimeric ion channel; packaging material, and instructions for administering the vector to a mammal in need thereof to treat an excitable cell-related disease or condition.

BRIEF DESCRIPTION OF THE DRAWINGS

FIGS. 1A-B illustrate the background conductance of GluCl receptors in absence of ligand. FIG. 1A. Example of a current response from GluCl WT. Whole-cell voltage-clamped cells, with no capacitive compensation, were ramped from −60 mV to +60 mV over 50 ms. The total current across the membrane Im is the sum of the capacitive current Ic, and the resistive current, $I_R$. FIG. 1B. Background conductance normalized by the mean capacitance of each receptor for the number of cells recorded (shown in parentheses). Soluble GFP was used as a mock-transfection control.

FIGS. 2A-2F illustrate the GluCl channel. FIG. 2A. Crystal structure (side view) of a modified GluCl α-homomeric channel with glutamate and IVM molecules bound (3RIF.pdb). Agonists bind at subunit interfaces; glutamate binds in the extracellular domain, IVM binds at the top half of the transmembrane domain. FIG. 2B. GluCl is differentially activated by glutamate and IVM. Electrophysiological traces were obtained from heteromeric GluCl αβ channels expressed in Xenopus oocytes. FIG. 2C. Top view of the GluCl channel showing symmetrical arrangement of subunits forming the pore. FIGS. 2D, 2E, & 2F. Residues of the helical pore-lining M2 domain. Leucine 9' is a highly conserved pore-lining residue. FIG. 2F discloses SEQ ID NOS 9-13, 4, 14 and 15, respectively, in order of appearance.

FIGS. 5A-5B show the effect of glycine on the membrane potential of HEK-293 cells expressing the GlyR α-Subunit (hGlyRa1). FIG. 5A) Glycine exhibits a dose-dependent effect on the membrane potential of HEK-293 cells expressing the GlyR α-Subunit (hGlyRa1). FIG. 5B) The response to Glycine is not affected by the presence of taurine (100 µM).

All rats are hypersensitive to mechanical stimulation (allodynia) at day 10 post-surgery. GTX-01* or a control vector was administered on Day 10. A time-dependent reversal of allodynia consistent with viral delivery of gene therapy in peripheral nerves was observed with a 33% reversal of allodynia by 13 days post-treatment and a 77% reversal at both day 22 and day 35 post-treatment. Data points represent the mean of 6 animals (5 animals on final data point)±SD. *** $P<0.001$.

Figure 13:
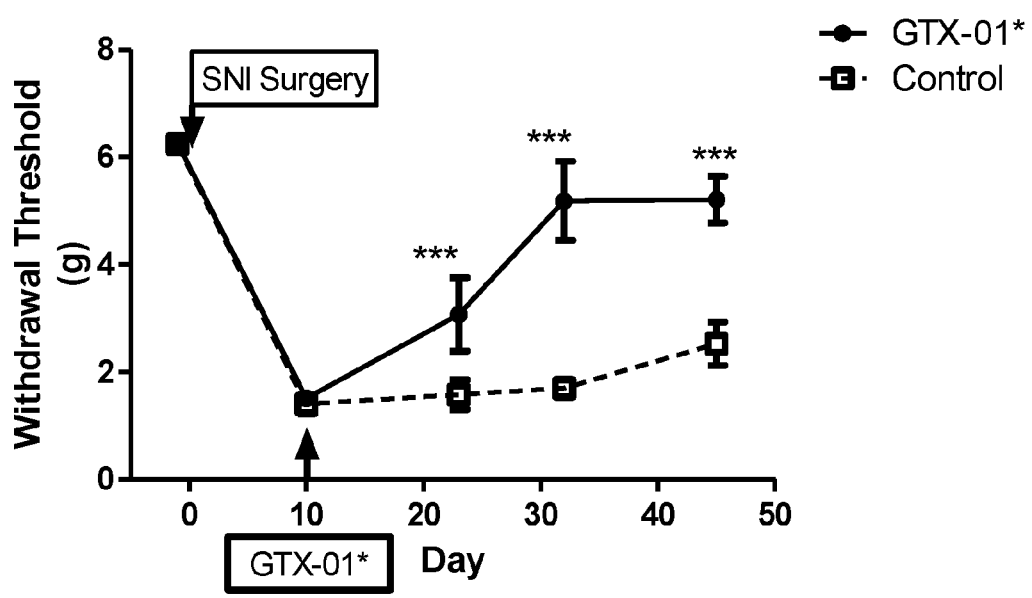
FIG. 13 shows a time-course of the analgesic effects of GTX-01* in the SNI model of neuropathic pain in the rat. Baseline evaluations were measured at Day −1 and surgery to sever the peroneal and tibial nerves was done on Day 0.
Figure 14:
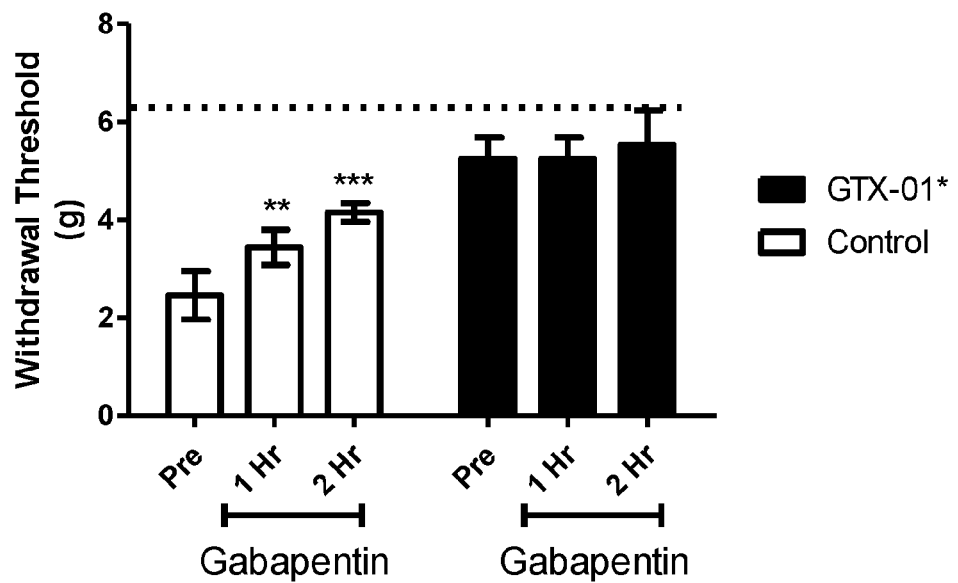

FIG. 14 illustrates the response when Gabapentin (100 mg/kg: IP) was administered on day 46 post-surgery. In those animals treated previously with a control vector (Control) and remained hypersensitive to mechanical stimulation gabapentin reduced the allodynic response by 25% at 1 hour and 44% at 2 hours post-dose. Gabapentin had no effect on the near-normal response to mechanical stimulation in those animals previously treated with GTX-01*. The dotted line represents the mean baseline withdrawal threshold measured in these animals prior to surgery (see FIG. 13). Data points represent the mean of 5 animals±SD. $P<0.01$; *$P<0.001$.

Figure 15:
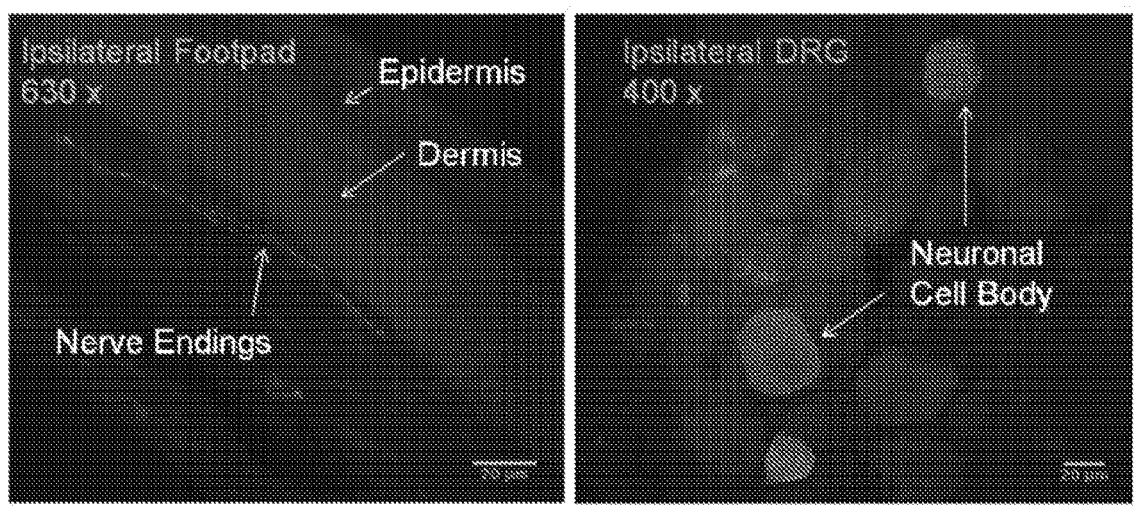

FIG. 15 shows the immunohistochemical evaluation of the DRG from the GTX-01*-treated animal harvested at day 22 post-treatment. In the right panel, individual cell bodies that stained positive for EYFP (a product of the pFB-hSyn-GluCloptalpha-mEYFP-L9'A gene delivered by GTX-01*). Similarly, in the left panel, nerve endings situated beneath the dermis layer of the paw from the same animal stained positive for EYFP.

Figure 16:
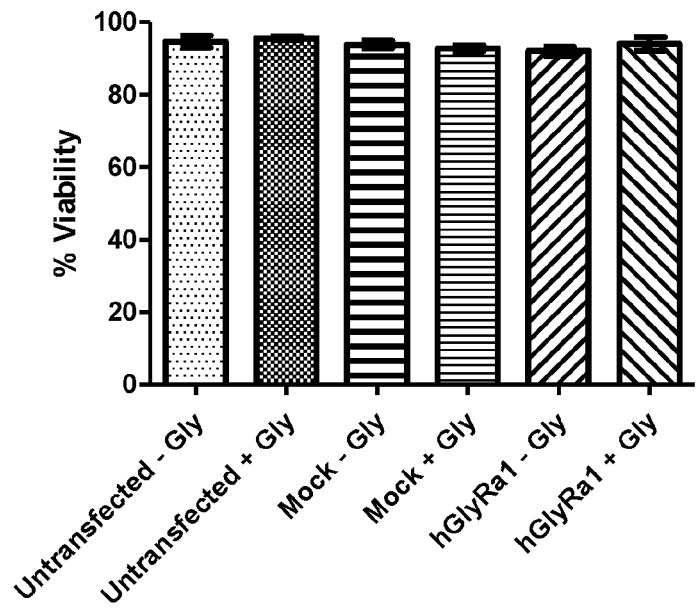

FIG. 16 shows the viability of HEK-293 cells that were untransfected, mock-transfected (Mock) or transfected with the alpha-1 subunit of the GlyR receptor channel (hGlyRa1) which forms an active $Cl^-$ channel that is activated by glycine. Post transfection the cells were cultured in either glycine-free media or DMEM which contains glycine (400 μM). Cell viability was measured using trypan blue dye exclusion at 72 hours post-transfection.

Figure 17:
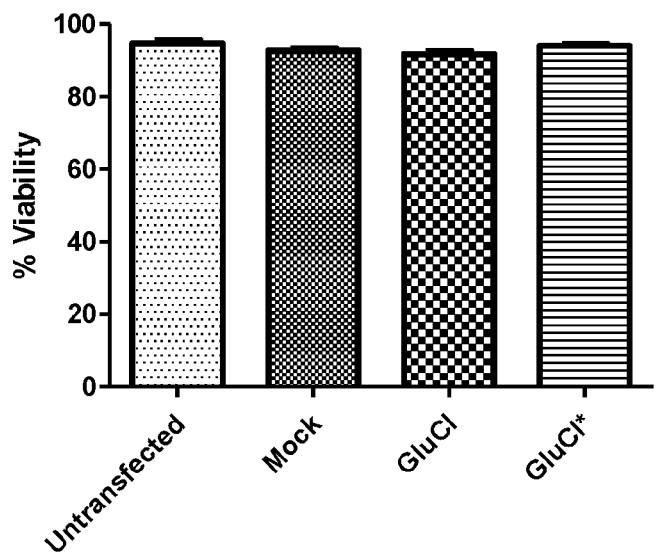

FIG. 17 shows cell viability of HEK-293 cells that were untransfected, mock-transfected (Mock) or transfected with wild-type GluCl alpha subunit (GluCl) or the L9'A mutation of the GluCl alpha subunit which forms a constitutively active $Cl^-$ channel (GluCl*). Cell viability was measured using trypan blue dye exclusion at 48 hours post-transfection.

Figure 18A:
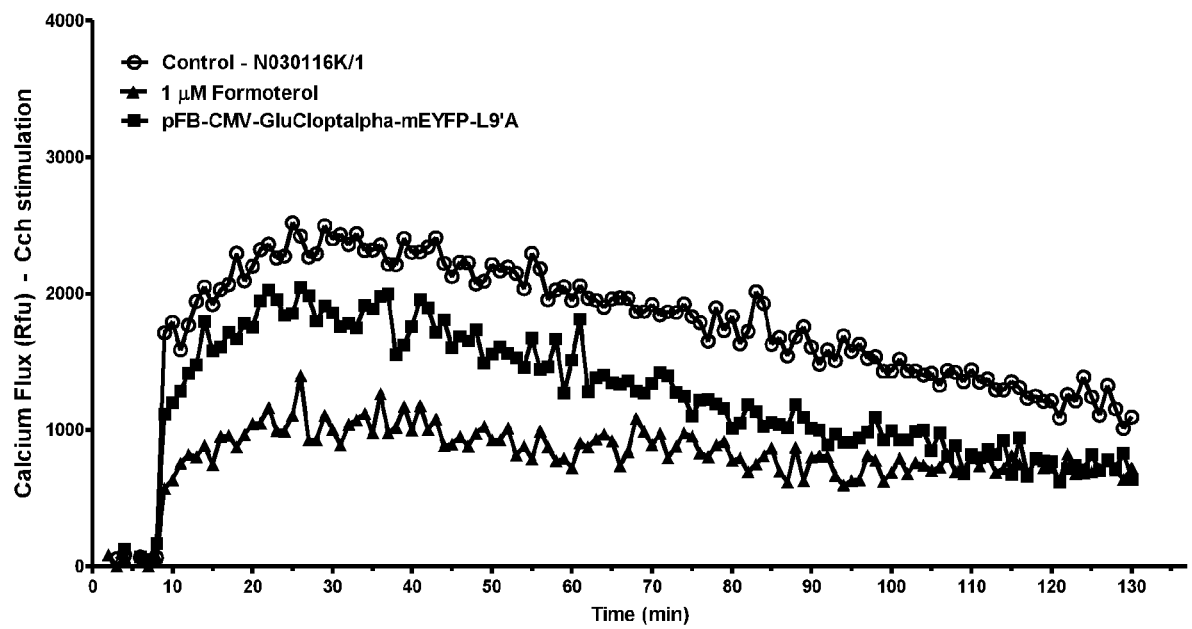
Figure 18B:
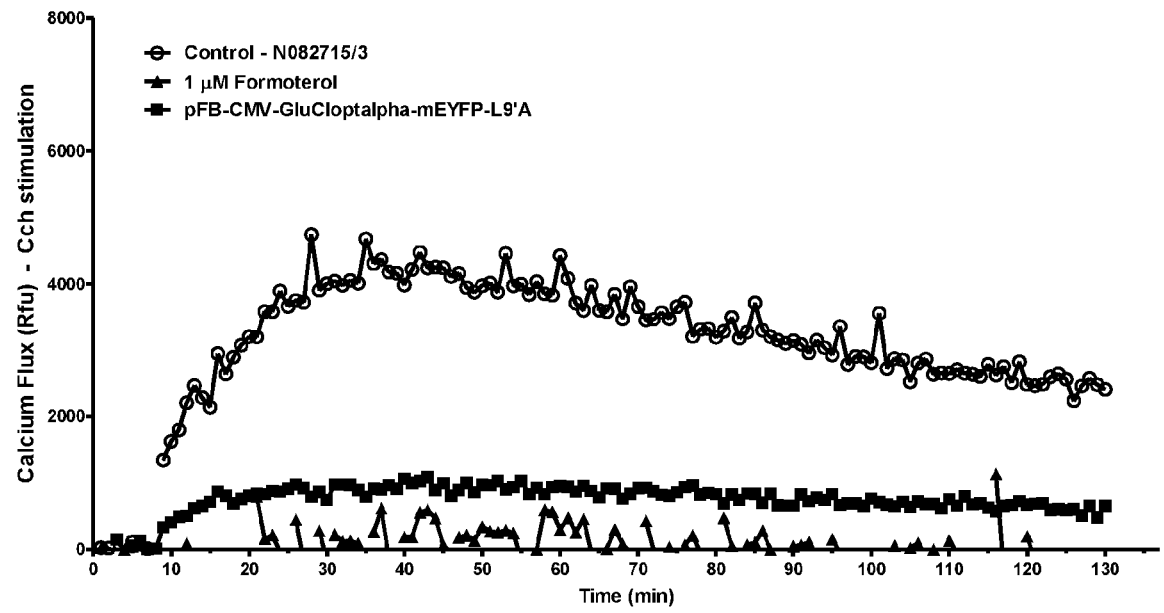

FIGS. 18A-B show the carbachol (Cch)-induced increase in intracellular $Ca^{++}$ and its antagonism by Formoterol (1 μM) in smooth muscle cells cultured from the lungs of normal healthy donors. The response to Cch is reduced in those cells, from both donors, that were transfected with GluCl alpha subunit L9'A mutation (pFB-CMV-GluCloptalpha-mEYFP-L9'A).

Figure 19A:
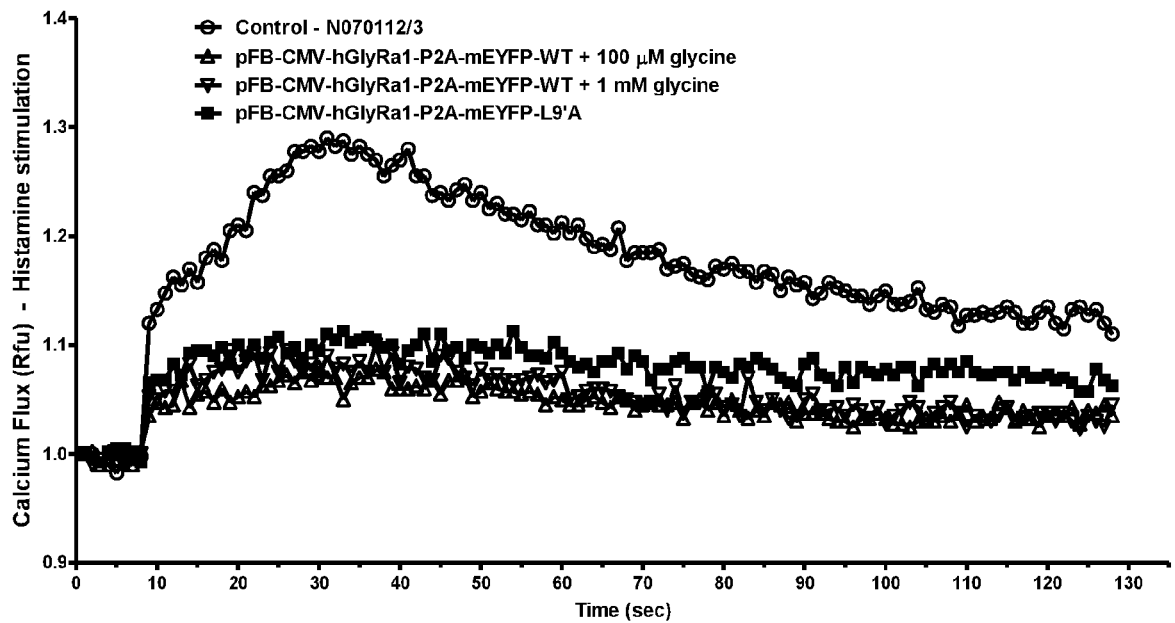
Figure 19B:
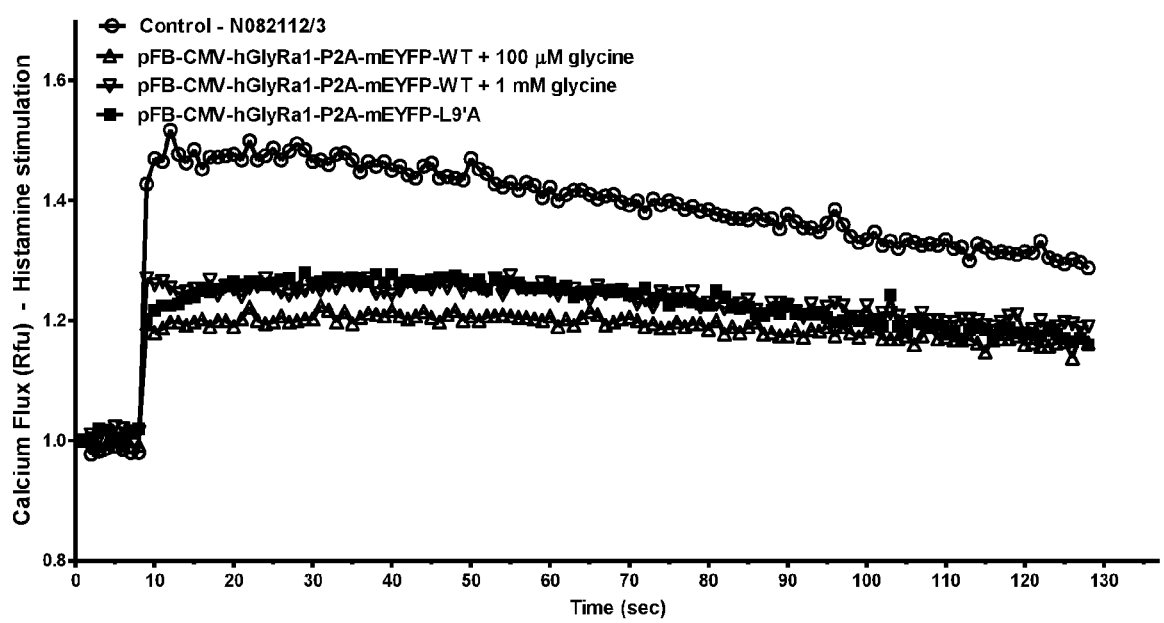

FIGS. 19A-B show the histamine-induced increase in intracellular $Ca^{++}$ in smooth muscle cells cultured from the lungs of normal healthy donors. The histamine response was attenuated in cells transfected with pFB-CMV-hGlyRa1-P2A-mEYFP-WT (wild-type GlyR alpha-1 subunit) and exposed to glycine (100 μm or 1 mM). The histamine response was also attenuated in cells transfected with pFB-CMV-hGlyRa1-P2A-mEYFP-L9'A (GlyR alpha-1 subunit L9'A) without the addition of glycine.

Figure 20:
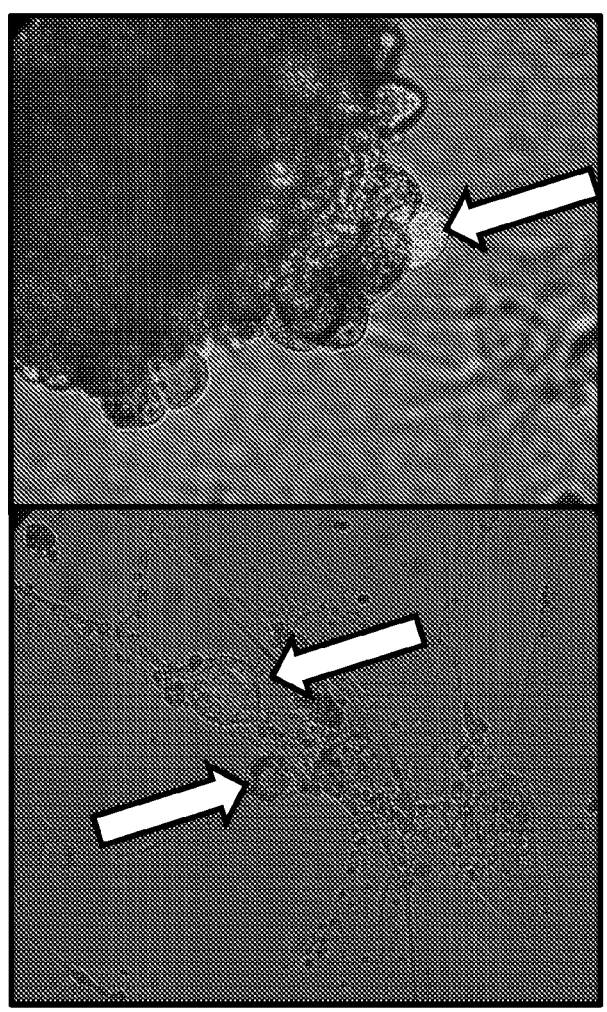

FIG. 20 shows images of human DRG cells in culture. At four days post exposure to AAV6-hSyn-GFP neuronal cells (arrows) show expression of GFP. GFP expression is limited to neuronal vs. glial cells.

DETAILED DESCRIPTION OF THE INVENTION

Methods of the Invention

Certain embodiments of the invention provide a method of modulating the electrophysiological activity of an excitable cell.

Certain embodiments of the invention also provide a method for the in vivo modulation of a mammalian cell's electrophysiological activity comprising contacting the cell in vivo with a vector as described herein.

Certain embodiments of the invention provide a vector as described herein for the in vivo modulation of a mammalian cell's electrophysiological activity.

Certain embodiments of the invention provide the use of a vector as described herein to prepare a medicament for the in vivo modulation of a mammalian cell's electrophysiological activity.

As used herein, the term "modulation of a mammalian cell's electrophysiological activity" refers to changes in the membrane potential of the cell, which is the difference in electric potential between the interior and the exterior of a biological cell. With respect to the exterior of the cell, typical values of membrane potential range from −40 mV to −80 mV. Increasing this membrane potential by making the interior of the cell more negative (hyperpolarization), for example via the introduction of chloride ions ($Cl-$), decreases the activity of excitable cells by reducing the likelihood of electrical activation of the cell (depolarization). The electrophysiology of a cell may be measured using techniques known in the art, for example, using a patch clamp procedure or a fluorescence-based assay described herein employing a FLIPR membrane potential assay used to detect voltage changes across the cell membrane.

Such methods may involve causing exogenous expression of a subunit of a multimeric ion channel (e.g., a subunit of a glycine receptor (GlyR)) in an excitable cell of a mammal (e.g., a human). In certain embodiments, the excitable cell may be exposed to an endogenous agonist (e.g., glycine) of the ion channel. Modulation of the ion channel (comprising the exogenous subunit) in response to endogenous agonist, modulates the electrophysiological activity of the excitable cell without the administration of exogenous agonists or allosteric modulators of the ion channel. In certain embodiments, the subunit (e.g., a GlyR or GluCl subunit) may comprise at least one mutation that results in a constitutively active ion channel upon multimerization of the subunit. In the case of a constitutively active ion channel, exposure to an agonist is no longer necessary and the electrophysiological activity of the excitable cell would be modulated without the administration of exogenous agonists or allosteric modulators of the channel.

As described herein, an excitable cell can be any cell that experiences fluctuations in its membrane potential as a result of ion channels activations. Such cells can include myocytes, neurons, and the like. In certain embodiments, the excitable cell is a peripheral neuron, a skeletal muscle cell or a trabecular meshwork cell of the eye.

As used herein, the term "exogenous" refers to a protein that is not natively expressed in a cell (e.g., an excitable cell). For example, GlyRs are generally expressed primarily in cells within the spinal cord and lower brain. Thus, where even a wild-type GlyR protein (i.e., other than a mutein) is expressed in, for example, peripheral neurons, its expression in such cells is exogenous. Also, exogenous expression can be expression of a protein at significantly higher levels than wild-type expression. Thus, inducement of expression of a protein in a cell expressing the protein at a low level is regarded as "exogenous" if the cell is induced to produce measurably more protein as a result of the induction. It is also noted that GluCl proteins are not expressed in mammals, thus their expression would be considered exogenous.

Certain embodiments of the invention provide a vector as described herein for use in medical therapy.

Certain embodiments of the invention provide a method of treating an excitable cell-related disease or condition in a mammal in need thereof, comprising administering an effective amount of a vector as described herein to the mammal.

Certain embodiments of the invention provide a vector described herein for the prophylactic or therapeutic treatment of an excitable cell-related disease or condition.

Certain embodiments of the invention provide the use of a vector described herein to prepare a medicament for the treatment of an excitable cell-related disease or condition in a mammal in need thereof.

As used herein, the term "an excitable cell-related disease or condition" refers to any disease or condition resulting from, associated with, or related to the electrophysiological activity of an excitable cell based on the net effect of anion (e.g., chloride) channel and cation (e.g., sodium) channel activity. In certain embodiments, the disease or condition may be the result of aberrant electrophysiological activity in an excitable cell (i.e., as compared to the electrophysiological activity present in excitable cell in a mammal not suffering from such a disease or condition). Excitable cell-related diseases or conditions are known in the art, and include for example, pain (e.g., chronic pain, e.g., joint pain or neuropathic pain), inflammation (e.g., joint inflammation), ocular hypertension (e.g., Glaucoma) and spastic hypertonia (spasticity). Accordingly, in certain embodiments, the excitable cell-related disease or condition is pain (e.g., chronic pain, e.g., joint pain or neuropathic pain), inflammation (e.g., joint inflammation), ocular hypertension (e.g., Glaucoma) or spastic hypertonia (spasticity).

In certain embodiments, the methods further comprise administering one or more other therapeutic agents (e.g., pharmaceutical agents) to the mammal. Accordingly, in certain embodiments, the methods further comprise administering to the mammal one or more other therapeutic agents (e.g., pharmaceutical agents) useful for treating ocular hypertension (e.g., Glaucoma). In certain embodiments, the one or more other therapeutic agents is a beta blocker (e.g., Timolol) or a miotic agent (e.g., Pilocarpine) or a carbonic anhydrase inhibitor (e.g., Acetazolamide) or a sympathomimetic (e.g., Dipivefrin) or a prostaglandin analog (e.g., Latanoprost) or a Rho kinase inhibitor. In certain embodiments, the methods further comprise administering to the mammal one or more other therapeutic agents (e.g., pharmaceutical agents) useful for treating pain (e.g., chronic pain, e.g., joint pain or neuropathic pain). In certain embodiments, the methods further comprising administering to the mammal one or more other therapeutic agents (e.g., pharmaceutical agents) useful for treating inflammation (e.g., joint inflammation). In certain embodiments, the one or more other therapeutic agents is a nonsteroidal anti-inflammatory drug (NSAID) (e.g., ibuprofen) or a steroid. In certain embodiments, the methods further comprising administering to the mammal one or more other therapeutic agents (e.g., pharmaceutical agents such as Baclofen, Benzodiazepines, Dantrolene sodium, Imidazolines or Gabapentin) useful for treating spastic hypertonia. In certain embodiments, the one or more other therapeutic agents may be selected from immune system suppressors, enhancers, antibiotics (e.g., microbicides or fungicides), and adrenaline.

As described herein, a vector that may be used in the methods of the invention may comprise an expression cassette, wherein the expression cassette comprises a nucleic acid encoding a subunit of a multimeric ion channel. In certain embodiments, the multimeric ion channel is activated by an endogenous compound. In other embodiments, the multimeric ion channel is constitutively active. Accordingly, in certain embodiments, an agonist (e.g., glycine) or an allosteric modulator of the ion channel is not administered to the mammal. Thus, in such embodiments the one or more other therapeutic agents described above would not be an agonist (e.g., glycine) or allosteric modulator of the ion channel.

As used herein, the term "agonist" refers to a chemical that can bind to a receptor/ion channel and activate the receptor/ion channel to produce a biological response. For example, glycine is a GlyR agonist.

As used herein, the term "allosteric modulator" refers to a chemical that can agonize or antagonize (open or close) the ion channel. Accordingly, this term encompasses both agonists and antagonists. For example, agonists of GlyR include glycine, taurine and beta-alanine, whereas antagonists of GlyR include strychnine. In addition the term encompasses a substance which indirectly influences (modulates) the effects of an agonist or inverse agonist at a target protein, for example a receptor. Allosteric modulators may bind to a site distinct from that of the orthosteric agonist binding site. Usually they induce a conformational change within the protein structure. A positive allosteric modulator (PAM) or allosteric enhancer induces an amplification of the orthosteric agonist's effect, either by enhancing the binding affinity or the functional efficacy of the orthosteric agonist for the target protein. A negative modulator (NAM) reduces the effects of the orthosteric ligand, but is inactive in the absence of the orthosteric ligand. Substances that occupy the allosteric binding site and are functionally neutral are called silent allosteric modulators (SAMs). Classic benzodiazepines are well-known PAMs of the $GABA_A$ receptor.

In certain embodiments, methods of the invention may further comprise modifying the mammal's diet. In certain embodiments, the diet may be modified to either increase or decrease levels of endogenous glycine in the mammal.

Methods for the Treatment of Pain and Inflammation

Certain embodiments of the invention provide a method of treating pain (e.g., chronic pain, e.g., joint pain or neuropathic pain) in a mammal (e.g., a human patient) in need thereof, comprising administering an effective amount of a vector as described herein to the mammal. In certain embodiments, the method may be used to attenuate the sensation of pain.

Certain embodiments of the invention also provide a method of treating inflammation (e.g., joint inflammation) in a mammal (e.g., a human patient) in need thereof, comprising administering an effective amount of a vector as described herein to the mammal.

Certain embodiments of the invention provide the use of a vector as described herein to prepare a medicament for treating pain or inflammation in a mammal.

Certain embodiments of the invention provide a vector as described herein for the therapeutic treatment of pain or inflammation.

It is estimated that up to 100 million Americans suffer from chronic pain. In chronic pain a significant percentage of patients are unsatisfied with current treatment, highlighting the large gap in pharmacological and non-pharmacological interventions for such conditions. The pain can be isolated pain, or the pain can be associated with a particular disease. The pain can be associated with certain conditions such as, but not limited to, chronic post-surgical pain, neuromas such as stump neuroma and Morton's neuroma, joint pain including sacroiliac pain, back pain and pain associated with any known human disease, including but not limited to, diabetes, arthritis, cardiovascular disease, autoimmune disease, respiratory disease (e.g., emphysema), infectious disease (e.g., viral or bacterial infections), neurological disease (e.g., Alzheimer's disease), gastrointestinal disease, liver disease, blood disorders, allergies, endocrine disease, and cancer. The pain can be associated with cancer of the oral cavity (e.g., tongue cancer and mouth cancer), the pharynx, the digestive system (e.g., the esophagus, stomach, small intestine, colon, rectum, anus, liver, gall bladder, and pancreas), the respiratory system (e.g., lung cancer), bones and joints (e.g., bony metastases, osteosarcoma), soft tissue, the skin (e.g., melanoma), breast, the genital system (e.g., ovarian cancer), the urinary system (e.g., bladder cancer, renal cancer), the eye and orbit, the brain and nervous system (e.g., glioma), or the endocrine system (e.g., thyroid). The cancer also can be a lymphoma (e.g., Hodgkin's disease and Non-Hodgkin's lymphoma), multiple myeloma, or leukemia (e.g., acute lymphocytic leukemia, chronic lymphocytic leukemia, acute myeloid leukemia, chronic myeloid leukemia, and the like). Also chronic pain such as, but not limited to, post-stroke pain or that associated with multiple sclerosis, spinal cord injury, migraine, HIV-related neuropathic pain, post-herpetic neuralgia, diabetic neuropathy, pancreatitis, inflammatory bowel syndrome, lower back pain, fibromyalgia, or pain resulting from nerve damage or injury such as post-surgical pain as in post thoracotomy pain or following hernia repair or "stump pain" after amputation, or pain resulting from nerve injury such as lateral femoral cutaneous nerve entrapment (meralgia paresthetica) or other situations whereby pain results from nerve injury due to for example entrapment, ischemia or inflammation.

For the treatment of pain (e.g., chronic pain), a vector as described herein can be delivered at the site of the pain using conventional injection techniques similar to those used for the delivery of local anesthetics. By way of non-limiting examples, intradermal or subcutaneous injections can be used to treat pain arising from the skin in such conditions as chronic post-surgical pain (CPSP) or post-herpetic neuralgia (PHN). Injection can be made directly into nervous tissue such as, by way of a non-limiting example, neuromas to treat conditions such as Morton's neuroma or "stump neuromas" that arise following amputation. Also by way of a non-limiting example direct injections can be made into nerve fibers and nerve trunks or ganglia for the treatment of regional pain such as diabetic neuropathy or pain associated with visceral cancers. The therapy can also be delivered directly into joints to alleviate the pain associated with, by way of a non-limiting examples, osteoarthritis, trauma, aging or inflammation. These joints may include but not limited to the facet joints, sacroiliac joint, knee, hip, shoulder, ankle, wrist, elbow etc.

The ability to treat pain using a vector as described herein can be tested using a range of animals models such as the Monosodium Iodoacetate—Induced Osteoarthritis (MIA-OA) model (Bove S E. et al. (2003) Osteoarthritis and Cartilage 11(11): 821-30; Schuelert N. and McDougall J J. (2009) Neuroscience Letters 465(2): 184-188; Combe R. et al. (2004) Neuroscience Letters 370(2-3): 236-240) or an inflammatory pain model such as the CFA—Complete Freund's Adjuvant inflammatory pain model (Fehrenbacher J C. et al. (2012) Current Protocols in Pharmacology 5.4.1-5.4.7, March 2012). Neuropathic pain models can also be used such as those resulting from nerve damage, for example the Chung spinal nerve ligation model (Chung J M. et al. (2004) Methods Mol Med. 99:35-45), the spared nerve injury model (Richner M. et al. (2011) Journal of Visualized Experiments 18(54): pii 3092) the Bennett chronic constriction nerve injury model (Austin P J. et al. (2012) Journal of Visualized Experiments 13(61): pii 3393) or the lysophosphatidic acid model (Inoue M. et al. (2004) Nat Med. 10(7):712-718; Ogawa K. et al. (2012) Eur J Pain 16(7):994-1004).

As described herein, certain embodiments of the invention provide a method for the treatment of pain in a mammal in need thereof, comprising administering an effective amount of a vector as described herein to a mammal. In such embodiments, the vector may be a viral vector (e.g., an AAV vector) comprising an expression cassette, wherein the expression cassette comprises a promoter and a nucleic acid encoding a subunit of a chloride channel. In certain embodiments, the viral vector is an AAV6 vector. In certain embodiments, the promoter is a human synapsin (hSyn) promoter. In certain embodiments, the nucleic acid encodes a subunit of GlyR. In certain embodiments, the nucleic acid encodes a subunit of a chloride channel, wherein the subunit comprises at least one mutation that results in a constitutively active ion channel upon multimerization of the subunit. In certain embodiments, the subunit is a GlyR subunit comprising at least one mutation that results in a constitutively active GlyR channel upon multimerization of the subunit.

Significant levels of glycine and taurine are also present in the synovial fluid (SF), especially in that of inflamed joints. Previous studies have demonstrated elevated levels of excitatory amino acids (EAA) and other neurotransmitters in SF extracted from patients with active arthritic conditions (Appelgren A. et al. (1991) Scand J Dent Res. 99: 519-521; Larsson J. et al. (1991) Scand J Rheumatol. 20: 326-335; McNearney T. et al. (2000) J Rheumatol. 27: 739-745). Additional studies have reported elevated plasma amino acid (AA) levels in patients with rheumatoid arthritis compared to normal controls (Trang L E. et al. (1985) Scand J Rheumatol. 14: 393-402). The source(s) of increased SF EAA levels is not known but possibilities include local cell production, neurogenic exudation, or passive diffusion from the blood or plasma across synovial membranes. The concentration elevations of SF EAA in symptomatic arthropathies and their reported association with SF RANTES, and MIP1-alpha concentrations suggests that local inflammatory joint processes rather than passive diffusion from plasma determines SF EAA concentrations (McNearney T. et al. (2004) Clin Exp Immunol. 137: 621-627). To assess this, McNearney and Westlund simultaneously drew plasma and synovial fluids from the knees of 14 recently deceased cadavers and 9 patients with active arthritis and measured the levels of EAA and other AA to assess the compartmental SF: Plasma concentration ratios. (McNearney T. and Westlund K. (2013) Int J Clin Exp Pathol. 6(3): 492-497). Their data showed that in non-arthritic samples the mean SF: Plasma concentration ratios of glycine and taurine were −2.11 and −1.57, respectively. However, in a patient suffering from Reiter's syndrome the mean SF: Plasma concentration ratio for glycine was approximately 2-fold higher in the SF than in plasma. In addition to an elevation in glycine, the level of SF glutamate was also significantly elevated in this patient by 7.5-fold.

The sources of elevated SF Glu and Asp concentrations in active arthritis are unknown, but likely candidates include plasma, local production from synoviocytes or osteocytes in the joint capsule or local secretion from nerve fibers. One might expect that SF Glu and Asp would be in full equilibrium with the plasma, based on size, as small physiologic molecules are usually in full equilibrium between plasma and synovial fluid (McCarty D. Arthritis and Allied Conditions. Edited by Koopman W J. Baltimore: Williams and Wilkins, 1997; pp: 81-102). However, the samples from the cadavers with no antemortem arthritis had significantly decreased EAA SF: Plasma concentration ratios compared to nine other AA. The significantly greater compartmental ratio differences of SF Glu and Asp indicate that plasma is not the sole or even major source of SF EAA. Higher SF: Plasma concentration ratios in one cadaver with antemortem arthritis and several patients with active inflammatory arthritic processes also support the hypothesis that SF EAA concentrations reflect local physiologic processes in the joint. The most likely source of these excitatory amino acids may be the stimulated release from the primary afferent nerve terminals supplying the joint, as is thought for substance P release into the joint (Yaksh T L. et al. (1988) Peripheral release of substance P from primary afferents. Proceedings from the Vth World Congress on Pain. Edited by Dubner R, Gebhart G F. Bond M R Amsterdam: Elsevier, pp: 51-54). The SF EAA values derived from normal rat suggest that the low values might be physiologic in the absence of active arthritis and are elevated in inflamed joints (Lawand N B. et al. (2000) Pain 86: 69-74; Lawand N B. et al. (1997) Eur J Pharmacol. 324: 169-177). Previous studies have demonstrated increased Glu immunoreactivity in the median articular nerve supplying inflamed joints of monkeys (Westlund K N. et al. (1992) Brain Res Rev. 17: 15-27). Thus, it is reasonable to assume that glutamate might also be released into the joint by nerve fibers. In a kaolin/carrageenan induced arthritis model in rats, the expected increase in SF Glu was abrogated with pretreatment with intra-articular lidocaine, which decreases neurotransmitter release from peripheral nerves (Lawand N B. et al. (2000)). Local glutamate and aspartate can bind and activate peripheral receptors on local osteocytes, chondrocytes and synoviocytes to enhance or perpetuate local inflammation and pathologies (Skerry T M. and Genever P G. (2001) Trends Pharmacol Sci. 22: 174-181; Lawand N B. et al. (1997) Eur J Pharmacol. 324: 169-177; Flood S. et al. (2007) Arthritis Rheum. 56: 2523-2534; Gu Y. et al. (2002) Calcif Tissue Intl. 70: 194-203; Laketic-Ljubojevic I. et al. (1999) Bone 25: 631-637; McNearney T A. et al. (2010) Am J Physiol Regul Integr Comp Physiol. 298: R584-598; Ramage L. et al. (2008) Osteoarthritis Cartilage 16:1576-1584). Thus it reasonable to expect that hyperpolarization of local afferent nerves innervating an inflamed joint could not only reduce pain but may also reduce inflammation by reducing the release of pro-inflammatory mediators into the joint.

Methods for the Treatment of Ocular Hypertension

Certain embodiments of the invention provide a method of treating ocular hypertension (e.g., Glaucoma) in a mammal in need thereof (e.g., a human patient), comprising administering an effective amount of a vector as described herein to the mammal. In certain embodiments, the administration results in lowered intraocular pressure in the mammal.

Certain embodiments of the invention provide the use of a vector as described herein to prepare a medicament for treating ocular hypertension in a mammal.

Certain embodiments of the invention provide a vector as described herein for the therapeutic treatment of ocular hypertension.

Figure 3:
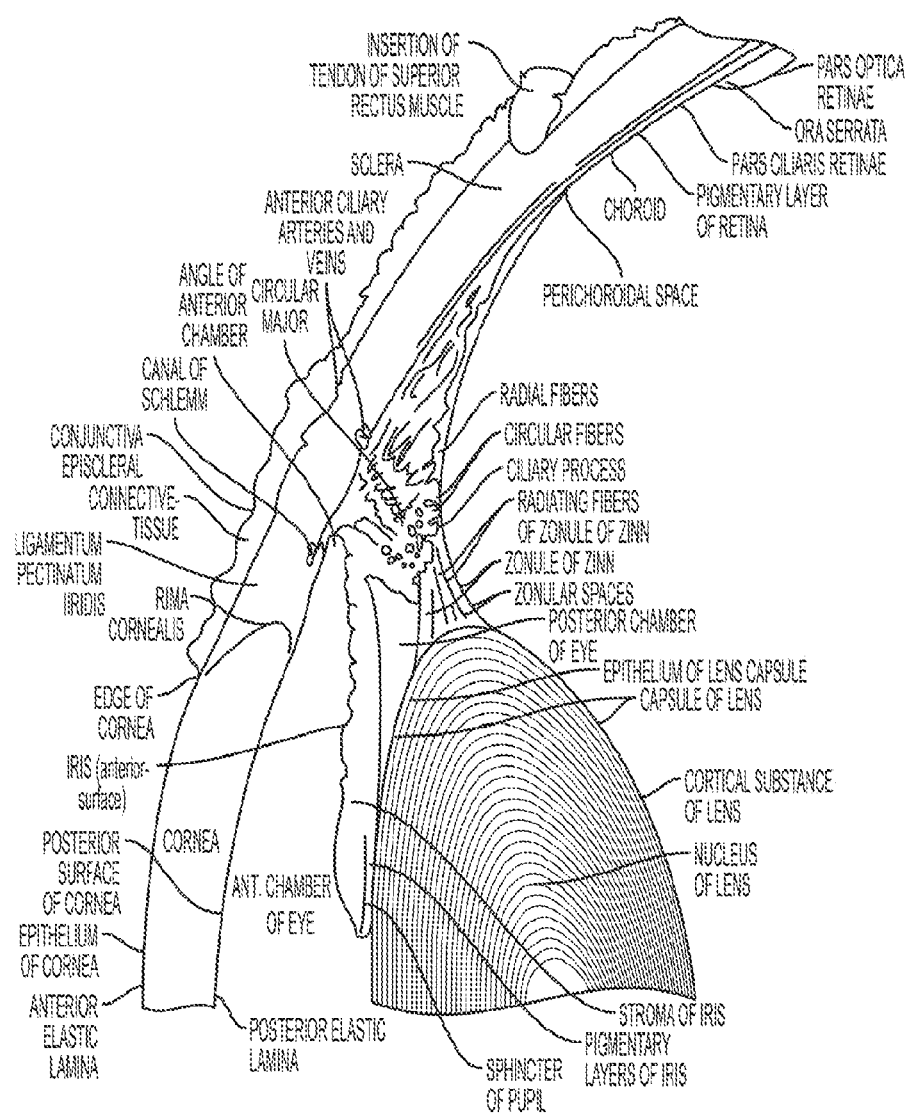
FIG. 3 illustrates certain aspects of the anatomy of the human eye.

Glaucoma is the second-leading cause of blindness in the world, and by 2020, the prevalence is projected to increase to 58.6 million worldwide and 3.4 million the United States. Glaucoma can be roughly divided into two main categories, open-angle and closed-angle (or angle closure) glaucoma. Referring to FIG. 3, an anatomical diagram depicting features of the human eye is shown. In reference to glaucoma, the "angle" refers to the space between the iris and cornea, through which fluid (Aqueous humor (AH)) must flow to drain from the eye via the trabecular meshwork (TM). Closed-angle glaucoma can appear suddenly and is often painful; visual loss can progress quickly, but the discomfort often leads patients to seek medical attention before permanent damage occurs. Open-angle, chronic glaucoma tends to progress at a slower rate and patients may not notice they have lost vision until the disease has progressed significantly. The exact etiology of open-angle glaucoma remains unknown. However, the major risk factor for most glaucoma patients, and the focus of treatment, is increased intraocular pressure (IOP), i.e. ocular hypertension (OHT). A progressive loss of the visual field due to cell loss in the retinal nerve fiber layer is a direct result of OHT. Vision loss can negatively affect a patient's quality of life and mobility, such as the ability to drive, which has a severe negative macroeconomic impact. The present invention relates predominantly to the treatment of OHT in open-angle glaucoma.

IOP is mainly maintained by the aqueous humor, which is produced by the ciliary body of the eye. When the ciliary bodies produce the aqueous humor, it first flows into the posterior chamber (bounded by the lens and the iris). It then flows through the pupil of the iris into the anterior chamber (bounded by the iris and the cornea). From here, it flows through the TM to enter the normal body circulation via Schlemm's canal (SC). In the human eye, the SC transfers an average of approximately 3 µl of aqueous humor per minute. Thus, the intraocular pressure is maintained by a delicate balance between synthesis and drainage of AH. The main mechanism of OHT is a decrease in outflow through the trabecular meshwork or uveoscleral pathways. The primary outflow pathway is via the TM which also makes the greatest contribution to outflow resistance of the aqueous humor, and is the therapeutic focus of the present invention.

The modern goals of glaucoma management are to avoid glaucomatous damage and nerve damage, and preserve visual field and total quality of life for patients, with minimal side effects. Screening for glaucoma is usually performed as part of a standard eye examination, which should include measurements of the IOP via tonometry.

IOP may be lowered with medication, usually eye drops. Several different classes of medications have been used, with several different medications in each class. Often the therapeutic effect of each of these medicines may be limited by local and systemic side effects. If side effects occur, the patient generally must be willing either to tolerate them, or to communicate with the treating physician to improve the drug regimen. Poor compliance with medications and follow-up visits has been cited as a major reason for vision loss in glaucoma patients (Nordstrom B L. et al. (2005) Am J Ophthalmol. 140:598).

Both laser and conventional surgeries have been performed to treat OHT, especially for those with congenital glaucoma. Although they have high success rates, these operations generally represent a temporary solution, with re-treatments required periodically, such as biennially. In most cases, medications are still necessary to control and maintain post-op IOP. However, surgery may lessen the amount of medication needed.

Thus, there remains a need for robust and reliable therapies for the treatment of OHT. For example, treatment methods for relaxing the cells of the TM to lower IOP, by reducing their hydraulic impedance to the outflow of AH.

In the traditional concept, trabecular meshwork is an inert tissue, with no regulatory properties of its own. In this concept, regulation of outflow resistance is determined by the ciliary muscle. However, work done during the last two decades has established that, in addition to being passively distended by the ciliary muscle, the trabecular meshwork has contractile properties of its own, and that the contraction and relaxation of this structure may influence ocular outflow in the sense that relaxation reduces intraocular pressure. Ample evidence supports the theory that trabecular meshwork possesses smooth-muscle-like properties. In addition, trabecular meshwork cells express a large number of transporters, channels and receptors, many of which are known to regulate smooth-muscle contractility. It has been shown that trabecular meshwork can be induced to contract and relax in response to pharmacological agents such as acetylcholine and endothelin (Lepple-Wienhues A. et al. (1991) Exp Eye Res. 53(1): 33-38; Stumpff F. and Wiederholt M. (2000) Ophthalmologica. 214 (1): 33-53). On the cellular level, this is coupled with depolarization of the plasma membrane and a rise in intracellular calcium. This increase in intracellular $Ca^{2+}$ is mediated by release of $Ca^{2+}$ from the endoplasmic reticulum but also an influx of extracellular $Ca^{2+}$ mediated via the opening of L-Type voltage-gated $Ca^{2+}$ channels. This effect can be blocked by the L-type voltage-gated channel blocker nifedipine (Stumpff F. and Wiederholt M. (2000) Ophthalmologica. 214 (1): 33-53). Relaxation of trabecular meshwork, on the other hand, appears to be coupled to a stimulation of the maxi-K channel, inducing hyperpolarization and a closure of L-type calcium channels (Stumpff F. et al. (1999) Invest Ophthalmol Vis Sci. 40(7): 1404-1417; Stumpff F. and Wiederholt M. (2000) Ophthalmologica. 214 (1): 33-53).

Figure 4:
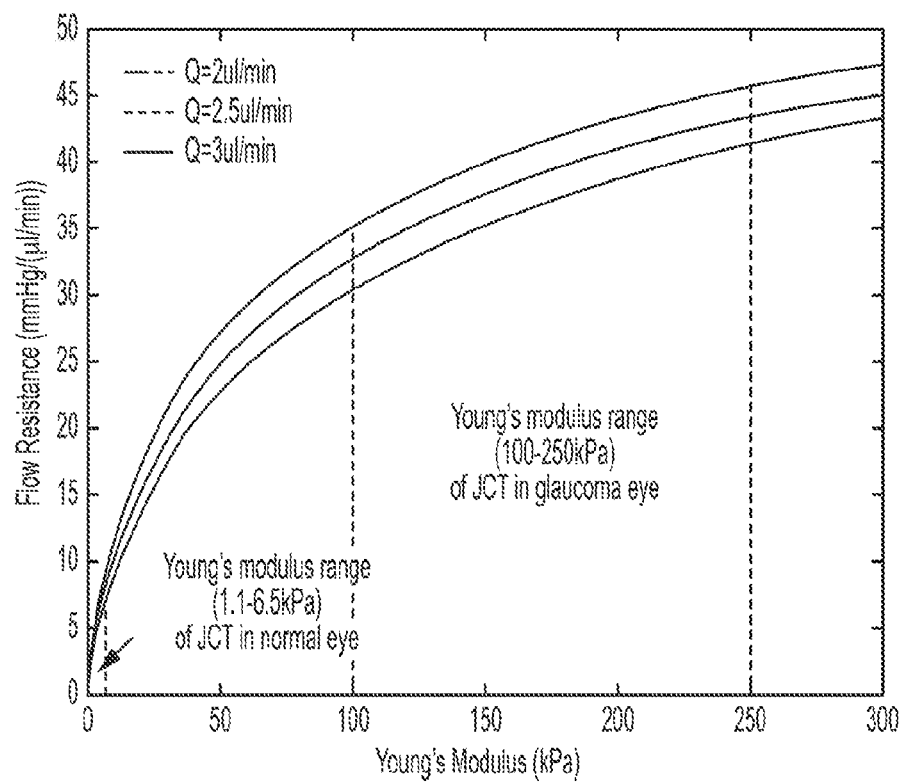
FIG. 4 illustrates a mathematical model of a flexible membrane with one micron holes as it becomes stiffer. Using the relationship for Poiseuille flow through the holes, the flow resistance of an aqueous solution is marked altered as the membrane becomes stiffer. Three curves are plotted with flows from 2 to 3 microliter per minute. This simplified example indicates facility is impacted as the TM becomes stiffer.

Relaxation of the TM will bring about greater compliance of the meshwork as measured, for example using atomic force microscopy (AFM). The Young's Modulus (a measure of compliance) measured in this way has been shown to correlate with flow resistance of the trabecular meshwork. The Young's modulus of the juxtacanalicular region (JCT) region of the trabecular meshwork in a normal eye is 1.1 to 6.5 kPa whereas that in the JCT of glaucomatous eye is in the region of 100 to 250 kPa, as shown in FIG. 4 (US Patent Application Publication US 2013/0184318 A1).

Described herein are mechanisms that bring about TM cell relaxation. These mechanisms decrease the contractility of the TM cell either by reducing the availability of intracellular calcium or by attenuating the ability of the cell to utilize the intracellular calcium necessary to activate contractile elements within the cell.

Given the similarities between the TM and smooth muscle cells, especially the role of the L-type voltage-gated $Ca^{2+}$ channel to provide the intracellular $Ca^{2+}$ needed to sustain a contraction, it appears that in some instances the smooth muscle cell can be used as a model of the pharmacological properties of the TM cell. It is therefore, expected that hyperpolarization of the cell by the influx of and subsequent relaxation of the airway smooth muscle (Yim P D. et al. (2011) The FASEB Journal 25(5): 1706-1717) and as shown in Example 8 (FIGS. 18 and 19) would predict that similar hyperpolarization of the TM cells would result in relaxation of the TM.

The use of constitutively active channels expressed on the surface of the trabecular meshwork cells using the techniques described above has significant advantages over ligand- or light-activated channels (US patent #US20150217133A1). The activity of ligand- and light-activated channels are dependent on the availability and concentration of the ligand or the irradiance level of light. Ligand-activated channels are dependent on the potency and the pharmacokinetic (PK) properties of the ligand. Accessibility of the ligand to the target tissue (particularly an issue in the eye), local free concentrations of the ligand, and residence time of the ligand within the tissue are all key determinants of the pattern of activity for the ligand-gated channels. The opsins are only active when activated by photons of light, thus during periods of low light (e.g., at night) the channels are not active. The dependency on chemical or physical activators is not an issue for the constitutively active channels, and the physiological effects will persist under all conditions and without the need for a patient to take any medications. In the case of OHT and POAG this is a critically important advantage as compliance among these patients is estimated to between 30 and 70%. In the case of the opsins, light is abundant to most patients during the day, but at night it is possible that they will have to use conventional pharmacotherapy to maintain an IOP of less than 21 mmHg. In the case of ligand-gated channels, these are prone to the same PK issues of delivery, metabolism and clearance as well as side effect that complicate and limit the use of conventional pharmacological-based therapies.

Presented herein are approaches that utilize the tissue-specific delivery and cell selective expression of genes that encode exogenous genetic material (i.e., a subunit of an ion channel), such as a subunit of a constitutively active chloride channel, by way of non-limiting example, to bring about relaxation of the contractile elements within the TM cells without the use of either chemical or physical stimuli. Relaxation of the TM will bring about increased permeability of the TM tissue structures resulting in a reduction in hydraulic impedance and thereby reducing high IOP to control OHT.

Delivery of the selected exogenous material to the eye of a mammal (e.g., a human patient) may follow one or more paradigms, such as those described below, which may take advantage of the unique anatomical positioning/access of the human eye relative to other systems and/or structures. As is described in Buie L K. et al. (2010) (Invest Ophthalmol Vis Sci., 51; 1:236-48), the location, morphology, and physiology of the cells of the outflow pathway of the eye lend themselves to efficient gene delivery. Because of the natural flow of aqueous humor, genes delivered into the anterior chamber may preferentially reach the trabecular meshwork. Once the vectors reach the trabecular meshwork, the physiological flow pattern of the fluid between and around the trabecular meshwork cell layers may provide the transfer molecules with a longer contact time and may facilitate their entry into the cells.

Delivery of a vector described herein, comprising the exogenous receptor genetic material to be expressed in cells of the targeted anatomy, may involve injection with a syringe or other device, in one or more configurations, including but not limited to internal topical injection or application (i.e., injection upon a surface of a tissue structure associated with a targeted portion of anatomy, or upon the anatomy itself, generally after surgical access, such as via endoscopic techniques). Each of these injection configurations is explored in further detail below.

Intracameral administration or application to a tissue structure surface may be utilized to deliver genetic material (i.e., a vector described herein). Recombinant vectors are capable of diffusing through tissues and infecting cells following such topical application or exposure. The efficacy of topical application of viral vectors has been increased using vector solutions suspended in gels. In one embodiment, a vector may be suspended in a gel and applied to the surface of tissues, or placed in the same anatomical space as the target tissue. Internal topical application may be achieved using laparoscopic techniques, wherein one or more small incisions may be made through the outer layer(s) of the eye and other pertinent tissue structures to allow insertion of the surgical apparatus (camera, needle, tools, etc.). A needle may be inserted intracamerally (as visualized through the camera or other imaging devices, such as a slit lamp biomicroscope, or operating microscope). In all cases, the vector may be mixed with a gel (e.g. the products sold under the tradenames "Healon" by Abbott, or "Viscoat" by Alcon) and then sprayed onto, painted onto, or injected out upon the surface of the pertinent tissue. For example, dose of approximately 0.1 mL saline containing $1\times10^{11}$ vg of AAV may be used to cover each 1 cm² area. These ranges are illustrative, and doses are tested for each vector pairing them with the targeted TM cells.

In one particular example of topical application, ocular hypertension may be addressed by topical application of vector solution or gel within the anterior chamber of the eye using a needle under microscopic visualization to achieve transfer of optogenetic material to the pertinent cells. The vector may be applied directly and topically either as a bolus into the aqueous humor of the anterior chamber or at multiple sites nearby the TM to cover as much of the available TM surface as possible, the goal being to infect the cells of the TM. Alternately, a plug of virus-laden gel may be placed in the anterior chamber and allowed to elute virus over the course of several hours. The plug should be placed such that it does not substantially occlude the TM, however. In a further alternate embodiment, a virus-eluting trabecular plug may be inserted for similar effect. An ophthalmic balanced salt solution, such as BSS, by Alcon, may be used to prepare the vector injection.

Access to the anterior chamber may be made after instillation of a topical anesthetic, such as proparacaine (sold as Alcaine, by Alcon) and a lid speculum may be inserted, such as the Seibel 3-D Lid Speculum, by Storz, to allow for a needle injection to be made into the anterior chamber. Alternately, in lieu of a needle injection, a paracentesis may be performed at the superior temporal limbus by using a sharp stab blade, such as the MIP Diamond Knife, by ASICO. An amount of aqueous humor may be discharged, and the vector injection may be performed using, for example, a 25 to 30-gauge anterior chamber cannula, such as a blunt-tipped Knolle Anterior Chamber Irrigating Cannula, by Storz, that is introduced into the AC via the paracentesis. Alternately, displaced aqueous humor may be vented intraoperatively via a paracentesis.

The ability of a vector described herein (e.g., encoding a subunit of a wild-type or modified chloride channel as described herein) and its delivery to the trabecular meshwork can be tested using a range of animals models such as measuring the effect of the treatment on the intraocular pressure in normal laboratory animals such as rats, mice or rabbits. Such measurements can be made in either conscious or sedated animals using a tonometer. Alternatively models of ocular hypertension can be used to measure the effect of the therapy. One such model is generated by the administration of 0.5% prednisolone acetate to the eye three times daily for 3 or 4 weeks (Gerometta R. et al. (2008) Investigative Ophthalmology & Visual Science 50(2): 669-73).

As described herein, certain embodiments of the invention provide a method for the treatment of ocular hypertension in a mammal in need thereof, comprising administering an effective amount of a vector as described herein to a mammal. In such embodiments, the vector may be a viral vector (e.g., an AAV) comprising an expression cassette, wherein the expression cassette comprises a promoter and a nucleic acid encoding a subunit of a chloride channel. In certain embodiments, the viral vector is a scAAV2 viral vector. In certain embodiments, the promoter is a matrix Gla protein (MGP) promoter. In certain embodiments, the nucleic acid encodes a subunit of a chloride channel, wherein the subunit comprises at least one mutation that results in a constitutively active ion channel upon multimerization of the subunit. In certain embodiments, the subunit is a GlyR subunit comprising at least one mutation that results in a constitutively active GlyR channel upon multimerization of the subunit.

Methods for the Treatment of Spastic Hypertonia

Certain embodiments of the invention provide a method of treating spastic hypertonia (spasticity) in a mammal in need thereof (e.g., a human patient), comprising administering an effective amount of a vector as described herein to the mammal.

Certain embodiments of the invention provide the use of a vector as described herein to prepare a medicament for treating spastic hypertonia (spasticity) in a mammal.

Certain embodiments of the invention provide a vector as described herein for the therapeutic treatment of spastic hypertonia (spasticity).

Spasticity is a condition in which certain muscles are continuously contracted. This contraction causes stiffness or tightness of the muscles and can interfere with normal movement, speech, and gait. Spasticity is usually caused by damage to the portion of the brain or spinal cord that controls voluntary movement. The damage causes a change in the balance of signals between the nervous system and the muscles. This imbalance leads to increased activity in the muscles. Spasticity negatively affects muscles and joints of the extremities, and is particularly harmful to growing children.

Spasticity affects more than an estimated 12 million people worldwide. About 80 percent of people with cerebral palsy (CP) have varying degrees of spasticity. With an estimated 500,000 people in the United States with some form of CP, this equates to about 400,000 people with some degree of CP-related spasticity. About 80 percent of people with multiple sclerosis (MS) have varying degrees of spasticity. With an estimated 400,000 people in the United States with MS, this equates to about 320,000 people with some degree MS-related spasticity. Other conditions that may cause spasticity include: traumatic brain injury (TBI), spinal cord injury (SCI), brain damage due to a lack of oxygen, stroke, encephalitis, meningitis, adrenoleukodystrophy, amyotrophic lateral sclerosis (Lou Gehrig's disease) and phenylketonuria.

Spasticity may be as mild as the feeling of tightness in muscles or may be severe enough to produce painful, uncontrollable spasms of the extremities; most commonly the legs and arms. Spasticity may also create feelings of pain or tightness in and around joints, and can cause low back pain. Adverse effects of spasticity include: muscle stiffness, causing movements to be less precise and making certain tasks difficult to perform; muscle spasms, causing uncontrollable and often painful muscle contractions; involuntary crossing of the legs; muscle and joint deformities; muscle fatigue; inhibition of longitudinal muscle growth; inhibition of protein synthesis in muscle cells. These can lead to additional complications such as: urinary tract infections, chronic constipation, fever or other systemic illnesses and pressure sores.

There are several types of treatment available that share the common goals of: relieving the signs and symptoms of spasticity; reducing the pain and frequency of muscle contractions; improving gait, hygiene, activities of daily living, and ease of care; reducing caregiver challenges such as dressing, feeding, transport, and bathing; improving voluntary motor functions involving objects such as reaching for, grasping, moving, and releasing; enabling more normal muscle growth in children. These treatment options include physical and occupational therapy; oral medications such as: Baclofen, Benzodiazepines, Dantrolene sodium, Imidazolines and Gabapentin. Surgical options are also available which include intrathecal baclofen (ITB) pumps and selective dorsal rhizotomy (SDR).

Botulinum Toxin (BTA) also known as Botox injections have proven effective when used in tiny amounts, by paralyzing spastic muscles. Injection sites are carefully determined based on the pattern of spasticity. When Botox is injected into the muscle(s), the release of acetylcholine is blocked, resulting in a relaxation of overactive muscles. The injection(s) generally take effect within a few days but last only about 12-16 weeks, until new nerve endings grow back and the affected muscle(s) recover. There are limitations in the number of injections that can be administered.

The options for the treatment of spasticity are thus limited, therefore a less invasive, more efficacious and patient friendly therapy is needed.

For the treatment of spasticity, an effective amount of a vector described herein may be administered to the mammal (e.g., a human patient). For example, vector can be delivered directly into the affected muscle group using multiple needle injections. During the procedure, small electrodes are attached with tape to the patient's skin over the affected muscle area. The electrodes are attached to an electromyography machine (EMG). The EMG is used to confirm needle location before the injection, to make sure the correct muscles are identified. The doctor will then ask the patient to move the muscle group. If the patient is unable to do this, the doctor will perform range-of-motion movements for the patient. This helps him or her get the most benefit from the injection. The vector is injected into the muscle using a small needle, which is attached to the EMG machine. The doctor may inject small amounts of the vector into several locations along the muscle group or within many muscle groups. This helps maximize the benefits of the treatment. In certain embodiments, the vector to be delivered can be tailored as described by Childers et al to cause hyperpolarization of either all or part(s) the targeted skeletal muscle group (Childers M. et al. (2014) Sci Transl Med. 6(220): 220ra210) or all or some of the motor nerves that innervate the targeted muscle group as described by Towne et al. (Towne C. et al. (2010) Gene Therapy 17(1): 141-6). The targeting of either muscular or neuronal cells will be determined based on the type of vector used (e.g., the type of AAV vector subtype), as well as the type of promoter included in the expression cassette.

The ability of a vector described herein to treat spasticity can be tested in a variety of animal models. For example, a vector of the invention may be injected into a selected muscle group and after a period of 4-6 weeks the function of the muscle in response to nerve stimulation can be measured either in the whole animal (Fertuck H C. et al (1775) J Cell Biol. 66, 209-13) or by removing the targeted muscle and its associated motor nerve and measuring the response to electrical nerve stimulation in vitro (Franco J A. (2014) J. Vis. Exp. (91), e51948, doi:10.3791/51948).

In certain embodiments, the vector is designed to target motor nerves to treat spasticity. In such a situation, the vector may be an AAV vector (e.g., AAV6 or AAV2). In certain embodiments, the vector is an AAV6 vector. In certain embodiments, vector comprises an expression cassette, wherein the expression cassette comprises a promoter and a nucleic acid encoding a subunit of a chloride channel. In certain embodiments, the promoter is the human synapsin (hSyn) promoter. In certain embodiments, the nucleic acid encodes a subunit of the GlyR chloride channel. In certain embodiments, the subunit is a GlyR subunit comprising at least one mutation that results in a constitutively active GlyR channel upon multimerization of the subunit.

In certain embodiments, the vector is designed to target skeletal muscle cells to treat spasticity. In such a situation, the vector may be an AAV vector. In certain embodiments, the vector is an AAV8 vector. In certain embodiments, the vector is an AAV9 vector. In certain embodiments, vector comprises an expression cassette, wherein the expression cassette comprises a promoter and a nucleic acid encoding a subunit of a chloride channel. In certain embodiments, the promoter is the human cytomegalovirus ("CMV") promoter. In certain embodiments, the promoter is the chicken beta-actin ("CBA") promoter. In certain embodiments, the promoter is the CAG or muscle-specific desmin promoter. In certain embodiments, the nucleic acid encodes a subunit of the GlyR chloride channel. In certain embodiments, the subunit is a GlyR subunit comprising at least one mutation that results in a constitutively active GlyR channel upon multimerization of the subunit. In certain embodiments, the vector is an AAV8 vector, comprising an expression cassette, wherein the expression cassette comprises a muscle-specific desmin promoter and a nucleic acid encoding a subunit of GlyR, wherein the GlyR subunit comprising at least one mutation that results in a constitutively active GlyR channel upon multimerization of the subunit.

Expression Cassettes

Vectors as described herein may be used in the methods of the invention. Such vectors may comprise an expression cassette, encoding a subunit of a multimeric ion channel.

In certain embodiments, an expression cassette comprises a nucleic acid encoding a subunit of a multimeric ion channel, wherein the subunit is capable of forming (e.g., by multimerizing) an active ion channel. In certain embodiments, the subunit forms an active ion channel by multimerizing with one or more additional subunits. In certain embodiments, the one or more additional subunits are endogenously expressed. In certain embodiments, the one or more additional subunits are recombinantly expressed. In certain embodiments, the multimeric ion channel is homomeric. In certain embodiments, the multimeric ion channel is heteromeric.

As used herein, the term "multimeric" refers to an ion channel comprising multiple subunits, which may be the same (homomeric) or different (heteromeric). Specific types of multimeric ion channels are discussed below, as well as their various subunits and conformations. As used herein, the term "multimerizing" refers to subunits, which may be the same or different and which may be endogenous or recombinantly expressed, associating to form a functional ion channel.

In certain embodiments, the ion channel is a chloride channel/functions as a chloride channel (e.g., a selective chloride channel). Accordingly, in certain embodiments, the nucleic acid encodes a subunit of a multimeric chloride channel.

In certain embodiments, the ion channel is a potassium channel/functions as a potassium channel (e.g., a selective potassium channel). Accordingly, in certain embodiments, the nucleic acid encodes a subunit of a multimeric potassium channel.

Ion Channels and Subunits Thereof

Methods of the invention may utilize vectors as described herein. Such vectors may comprise an expression cassette, encoding a subunit of a multimeric ion channel. For example, these vectors may be used to target expression the multimeric ion channel to a particular cell(s) in a mammal, thereby modulating the electrophysiological activity of the cell(s) (e.g., excitable cell(s)). For example, such modulation may result in physiological effects (e.g., change the conductance of sensory neurons to alleviate pain).

Table 1 below includes a non-limiting list of Cys-loop receptors (i.e., multimeric ion channels), their subunits and their ligands. These ion channels/subunits may be used in the methods described herein. Accordingly, in certain embodiments, the ion channel comprises at least one subunit described in Table 1 below. Thus, in certain embodiments, the expression cassette comprises a nucleic acid encoding a subunit selected from the subunits described in Table 1.

In certain embodiments, the multimeric ion channel is a glycine receptor (GlyR). In certain embodiments, the encoded subunit is selected from the group consisting of an alpha-1 subunit, an alpha-2 subunit, and alpha-3 subunit, an alpha-4 subunit and a beta-subunit of GlyR. In certain embodiments, the GlyR subunit may multimerize with one or more additional subunits, which may be the same or different and may be endogenously or recombinantly expressed. In certain embodiments, the encoded subunit is an alpha-1-subunit of GlyR (GlyRα1). In certain embodiments, the GlyRα1 is human GlyRα1 (hGlyRα1). GlyR subunits are known in the art; accession numbers for various GlyR subunit sequences, as well as specific GlyR subunit sequences are included below.

In certain embodiments, the multimeric ion channel is a γ-Aminobutyric Acid Receptor (GABA$_A$R). In certain embodiments, the multimeric ion channel is a GABA$_{A-\rho}$ Receptor (GABA$_C$). In certain embodiments, the encoded subunit is selected from the group consisting of GABRA1 ($\alpha_1$), GABRA2 ($\alpha_2$), GABRA3 ($\alpha_3$), GABRA4 ($\alpha_4$), GABRA5 ($\alpha_5$), GABRA6 ($\alpha_6$), GABRB1 ($\beta_1$), GABRB1 ($\beta_2$), GABRB1 ($\beta_3$), GABRG1 ($\gamma_1$), GABRG2 ($\gamma_2$), GABRG3 ($\gamma_3$), GABRD ($\delta$), GABRE ($\epsilon$), GABRP ($\pi$), GABRQ ($\theta$), GABRR1 ($\rho_1$), GABRR2 ($\rho_2$) and GABRR3 ($\rho_3$).). GABA$_A$R subunits are known in the art; accession numbers for various human GABA$_A$R subunit sequences include: GABRA1 (NM_000806), GABRA2 (NM_000807), GABRA3 (NM_000808), GABRA4 (NM_000809), GABRA5 (NM_000810), GABRA6 (NM_000811), GABRB1 (NM_000812), GABRB2 (NM_021911), GABRB3 (NM_000814), GABRG1 (NM_173536), GABRG2 (NM_198904), GABRG3 (NM_033223), GABRD (NM_000815), GABRE (NM_004961), GABRP (NM_014211), GABRQ (NM_018558), GABRR1 (NM_002042), GABRR2 (NM_002043) and GABRR3 (NM_001105580).

In certain embodiments, the multimeric ion channel is a glutamate-gated chloride channel (GluCl). In certain embodiments, the encoded subunit is selected from the group consisting of $\alpha_1$, $\alpha_{2A}$, $\alpha_{2B}$, GBR2A ($\alpha_{3A}$), GBR2B ($\alpha_{3B}$) and β. As discussed above, GluCl proteins are not expressed in mammals and may cause an immune response in tissues that are not immune-privileged. Therefore, in certain methods of the invention, a vector comprising an expression cassette, wherein the expression cassette comprises a nucleic acid encoding a subunit of GluCl may be targeted to immune privileged cells, including, but not limited to, the central nervous system (including the brain and the spinal cord) and the eye. GluCl subunits are known in the art; accession numbers for various GluCl subunit sequences include: GluCl alpha (AY195802.1) and GluCl beta (AY195803.1).

In certain embodiments, the subunit comprises at least one mutation (i.e., a mutein subunit; e.g., as compared to a corresponding wildtype subunit). In certain embodiments, the encoded subunit has about 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity to a corresponding wildtype subunit.

"Wild-type" or "naturally occurring" or "native" refers to the normal gene, protein or organism found in nature without any known mutation. Accordingly, a "wildtype subunit" refers to a normal subunit found in nature without any known mutation. A corresponding subunit would refer to a subunit of the same type and species, e.g., a mutant hGlyRα1 being compared to a wildtype hGlyRα1.

In certain embodiments, the subunit comprises at least one mutation that results in enhanced agonist sensitivity of the ion channel (e.g., as compared to a corresponding wildtype ion channel).

In certain embodiments, the ion channel may be activated by an endogenous agonist/ligand.

In certain embodiments, the encoded subunit comprises at least one mutation that results in a constitutively active ion channel upon multimerization of the subunit. Such constitutively active ion channels are discussed below in further detail.

TABLE 1

| Receptor/Channel | Subunits | Ligands |
|---|---|---|
| Glycine Receptor (GlyR) | $\alpha_{1-4}$, β<br>GLRA1 ($\alpha_1$)<br>GLRA2 ($\alpha_2$)<br>GLRA3 ($\alpha_3$)<br>GLRA4 ($\alpha_4$)<br>β | β-Alanine<br>D-Alanine<br>D-Serine<br>Glycine<br>Hypotaurine<br>L-Alanine<br>L-Proline<br>L-Serine<br>Milacemide<br>Quisqualamine<br>Sarcosine<br>Taurine |
| γ-Aminobutyric Acid Receptor (GABA$_A$R) GABA$_{A-\rho}$ Receptor (GABA$_C$) | $\alpha_{1-6}$, $\beta_{1-3}$, $\gamma_{1-3}$, δ, ε, π, θ, $\rho_{1-3}$<br>GABRA1 ($\alpha_1$)<br>GABRA2 ($\alpha_2$)<br>GABRA3 ($\alpha_3$)<br>GABRA4 ($\alpha_4$)<br>GABRA5 ($\alpha_5$)<br>GABRA6 ($\alpha_6$)<br>GABRB1 ($\beta_1$)<br>GABRB1 ($\beta_2$)<br>GABRB1 ($\beta_3$)<br>GABRG1 ($\gamma_1$)<br>GABRG2 ($\gamma_2$)<br>GABRG3 ($\gamma_3$)<br>GABRD (δ)<br>GABRE (ε)<br>GABRP (π)<br>GABRQ (θ) | γ-Aminobutyric Acid |

TABLE 1-continued

| Receptor/Channel | Subunits | Ligands |
|---|---|---|
| | GABRR1 ($\rho_1$) | |
| | GABRR2 ($\rho_2$) | |
| | GABRR3 ($\rho_3$) | |
| Glutamate-gated chloride Channel (GluCl) | $\alpha_{1-3}$, $\beta$ | Glutamic Acid |
| | $\alpha_1$ | |
| | $\alpha_{2A}$ | |
| | $\alpha_{2B}$ | |
| | GBR2A ($\alpha_{3A}$) | |
| | GBR2B ($\alpha_{3B}$) | |
| | $\beta$ | |

Table 1. Members of the Cys-loop ligand-gated ion channels and their respective subunits and their amino acid ligands. The channels listed are the chloride-selective members of the Cys-loop ligand-gated ion channels. The adult form of the GlyR is the heteromeric $\alpha_1\beta$ receptor, which is believed to have a stoichiometry of three $\alpha_1$ subunits and two $\beta$-subunits four $\alpha_1$-subunits and one $\beta$-subunit. Five subunits can combine in different ways to form or $GABA_A$ channels. The minimal requirement to produce a GABA-gated ion channel is the inclusion of both $\alpha$- and $\beta$-subunits, but the most common type in the brain is a pentamer comprising two $\alpha$'s, two $\beta$'s, and a $\gamma$ ($\alpha_1\beta_2\gamma_2$). The GluCl channels are pentameric structures composed of $\alpha$- and $\beta$-subunits. The ratios of the $\alpha$- and $\beta$-subunits are not fixed but are usually comprised of 2 or 3 $\alpha$-subunits with the complementary 3 or 2 $\beta$-subunits, respectively. In the case of the GlyR and GluCl the $\alpha$-subunits are able to form functional homo-pentameric receptors in mammalian cell lines.

Glycine Receptor (GlyR)

GlyR is a member of the nicotinicoid superfamily of ligand-gated ionotropic receptors that mediate fast neurotransmission in the central nervous system (CNS). In the case of the GlyR, binding of glycine ($EC_{50}$ of about 100 µM) or other agonists leads to transient gating of this anion-selective channel. In adults, the GlyR is believed to typically have a stoichiometry of 2 α subunits and 3 β subunits (Rajendra S. et al. (1997). Pharmacol Ther. 73(2): 121-46). Heterologous expression of just the human al subunit, however, is sufficient to reconstitute an active glycine-gated channel with pharmacological properties essentially identical to those of native channels (Sontheimer H. et al. (1989) Neuron 2(5): 1491-1497; Jensen A A. and Kristiansen U. (2004) Biochemical Pharmacology 67(9): 1789-1799). Accordingly, for use in the inventive method, the GlyR protein can be a wild-type subunit of GlyR (e.g., alpha1, alpha2, alpha3, alpha4, or beta). In certain embodiments, the GlyR subunit may be a mammalian GlyR subunit. In certain embodiments, the GlyR subunit may comprise one or more mutations as compared to a corresponding wildtype GlyR subunit (i.e., the nucleic acid may encode a mutein of a GlyR subunit). The GlyR proteins are well characterized (Rajendra S. et al. (1997). Pharmacol Ther. 73(2): 121-46) and the sequences encoding many subunits from mammalian species are indexed in genetic databases or are otherwise available. For example, sequences relating to the alpha1 subunit of GlyR can be found at NCBI Accession Nos. NM_000171 (human), NM_020492 (mouse) and NM_013133 (rat). Sequences relating to the alpha2 subunit of GlyR can be found at NCBI Accession Nos. NM_002063 (human), CR450343 (cDNA) (human)), NM_183427 (mouse), and NM_012568 (rat). Sequences relating to the alpha3 subunit of GlyR can be found at NCBI Accession Nos. NM_006529 (human), NM_001042543 (human), BC036086 (human), NM_080438 (mouse), AY230204 (mouse), AF362764 (mouse), and NM_053724 (rat). Sequences relating to the alpha4 subunit of GlyR can be found at NCBI Accession Nos. NM_010297 (mouse), and BC110630 (mouse). Sequences relating to the beta subunit of GlyR can be found at NCBI Accession Nos. NM_000824 (human), NM_010298 (mouse), and NM_053296 (rat).

In addition to wild-type GlyR subunits, mutant forms of GlyR subunit with altered activity (muteins) also are known, and can be used in the context of the present invention. In this regard, the nucleic acid may encode a GlyR subunit comprising one or more mutations as compared to a corresponding wildtype GlyR subunit (i.e., a mutein GlyR subunit). For example, certain muteins of GlyR proteins result in altered ion-channel properties, such as resulting in a cationic ion channel (e.g., Δ250 A251E: Keramidas A. et al. (2002) J. Gen. Physiol. 119, 393-410). Other muteins are known that lack sites for zinc potentiation or zinc inhibition (Hirzel K. et al. (2006) Neuron 52: 679-690) affinity for allosteric modulators (e.g., anesthetic potentiation (Hemmings H C. et al. (2005) Trends Pharmacol. Sci. 26, 503-10), or affinity for ligands (Rajendra S. et al., (1995) Neuron 14, 169-175; Schrnieden V. et al. (1993) Science 262, 256-258). Mutation of GlyR subunits also can selectively alter ion permeation (e.g., anionic- or cationic-selective channels), and redesign a receptor subunit's ligand binding pockets to recognize unique pharmacologic agents. For example, to alter the sensitivity and selectivity of a GlyR protein for a particular ligand, point mutations can be made in the GlyRa1 subunit that are expected to shift the dose response curve to the left or right (i.e., less or more specific to glycine).

Mutant forms of subunits (e.g., GlyR) can be generated using any suitable method known in the art. Such methods include, for example, site-directed mutagenesis, random mutagenesis by PCR, linker-scanning mutagenesis of DNA, and chemical mutagenesis (see, e.g., Ausubel et al., eds., Short Protocols in Molecular Biology, $5^{th}$ Ed., John Wiley & Sons, Inc. (2002)).

Once expressed in a target cell from a vector described herein, a GlyR subunit may multimerize to form a channel on the surface of the cell (e.g., an excitable cell). These channels may be activated by peripherally circulating glycine (endogenous glycine). The blood concentrations of glycine have been reported to be approximately 230-330 µM. Specifically, 242.0+/−44.0 µM in normal adult male and 258.0+/−64.0 µM in normal adult female (Geigy Scientific Tables, 8th Rev edition, pp. 93. Edited by C. Lentner, West Cadwell, N.J.: Medical education Div., Ciba-Geigy Corp. Basel, Switzerland c1981-1992); 329.9+/−105.6 µM in normal adults of both sexes (Psychogios N. et al. (2011) PLoS One 6(2):e16957); 212.4+/−57.4 µM in normal adult males (Grant S L. et al. (2006) J Chromatogr B Analyt Technol Biomed Life Sci. 844(2):278-82); 230.0 µM (178.0-282.0 µM) in normal adults of both sexes (Cynober L A. (2002) Nutrition 18(9):761-6); 325.4+/−126.8 µM in normal adults of both sexes (Psychogios N. et al. (2011) PLoS One 6(2):e16957).

It can be envisioned that if neuronal afferents were transfected with the alpha-subunit of the glycine receptor, the physiology of the neuronal cells could be altered by virtue of changes in the membrane potential due to the influx of Cl⁻ via the glycine receptor activated by endogenous glycine, based on 1) the above levels of glycine that have been reported in human blood; 2) the observation that in arthritic joints the level of glycine is approximately 2-fold that in the blood (McNearney T. and Westlund K. (2013) Int J Clin Exp Pathol. 6(3): 492-497); and 3) the observation that the glycine-sensitivity of GlyR formed by expression of only α-subunit ($ED_{50}$=85 to 100 µM) (Sontheimer H. et al. (1989) Neuron 2(5): 1491-1497; Jensen A A. and Kristiansen U. (2004) Biochemical Pharmacology 67(9): 1789-1799).

Constitutively Active Ion Channels

As discussed above, in certain embodiments, the multimeric ion channel may be a constitutively active ion channel (e.g., a constitutively active GlyR or GluCl). Thus, constitutively active ion channels may be used in methods of the invention (e.g., to modulate the activity of excitable cells and to treat excitable cell-related diseases or conditions, such as chronic pain, ocular hypertension or spasticity).

Accordingly, in certain embodiments of the invention, an expression cassette comprises a nucleic acid encoding a subunit of a multimeric ion channel (e.g., a monomeric or heteromeric ion channel), wherein the subunit comprises at least one mutation (i.e., a mutein subunit) that results in a constitutively active ion channel upon multimerization of the subunit. In certain embodiments, the constitutively active ion channel functions as a chloride channel. In certain embodiments, the constitutively active ion channel functions as a potassium channel.

As used herein, the term "constitutively active ion channel" refers to an ion channel that is continuously activated and does not need to be exposed to an agonist (e.g., chemical or biological) or a physical activator (e.g., pressure, heat or light) or the elecrophysiological state of the cell for it to be activated. Assays to measure the activity of an ion channel are known in the art. In certain embodiments, an assay described in the Examples may be used to determine if an ion channel is constitutively activated. Thus, in such embodiments that utilize a constitutively active ion channel, an agonist or allosteric modulator would not be administered to the mammal.

By way of non-limiting example certain mutations of the *Caenorhabditis elegans* glutamate-gated chloride channel (GluCl) have been shown to be constitutively active or leaky. These mutations, some of which are listed in Table 2 and their activity described in FIG. 1, when expressed in the cell membrane lead to a basal conductance carried by chloride ions.

TABLE 2

| Mutations of the Leucine 9' residue in the M2 domain of the of the α subunit in the GluCl channel | Amino acid substituted for leucine | Spontaneous activity |
| --- | --- | --- |
| None (WT) | None | 0 |
| L9'I | Isoleucine | + non-significant |
| L9'F | Phenylalanine | 0 |
| L9'V | Valine | + non-significant |
| L9'A | Alanine | ++ significant |
| L9'G | Glycine | ++ significant |
| L9'S | Serine | 0 |
| L9'T | Threonine | + non-significant |

Table 2. Substitution of the Leucine 9' residue in the M2 domain of the of the α-subunit in the GluCl channel to amino acids with the smallest side-chains (alanine or glycine) generated constitutively open channels having the largest background conductance which was significantly different from WT receptors. The three L9' mutants with a-branched side-chains (isoleucine, valine or threonine) did have a greater background conductance than WT receptors on average, but the increase was not statistically significant for the number of cells sampled.

In embodiments wherein constitutively active chloride channels are to be utilized in a method of the invention to modulate the electrical activity of an excitable cell, by way of a non-limiting example, modified glutamate-gated chloride (GluCl) channels can be used. GluCl chloride currents are gated by the traditional neurotransmitter glutamate and the semi-synthetic anti-helminthic drug ivermectin (IVM). A 3.3 A-resolution crystal structure of a modified homomeric GluCl channel reveals the binding site locations for each of these agonists (FIG. 2A, 2B). Glutamate binds at the classical neurotransmitter binding site located in the extracellular domain at the interface of two subunits. Ivermectin binds at a separate, unconventional site, inserting at the upper periphery of the transmembrane helices also at the interface of two adjacent subunits. Structural coordinates of the channel represent an open-pore conformation with the side-chains of pore-lining residues clearly defined (FIG. 2C, 2D). One pore-lining residue, leucine 9' (L9'), resides in the middle of the M2 transmembrane domain. L9' is highly conserved among subunits of the Cys-loop receptor family and has been proposed to serve as a hydrophobic channel gate (FIG. 2E, 2F) (Unwin N. (1993) J Mol Biol. 229:1101-1124; Miyazawa A. et al. (2003) Nature 423:949-955; Beckstein O. and Sansom M S. (2006) Phys Biol. 3:147-159).

The highly conserved leucine 9' residue in the M2 domain of the α-subunit in the GluCl channel was mutated to each of seven other residues, L9'I, F, V, A, G, S, T (whereby the L9' leucine residue was substituted with isoleucine, phenylalanine, valine, alanine, glycine, serine or threonine, respectively) (see Table 2). Transfected HEK293 cells were voltage clamped in whole-cell configuration with no capacitive compensation. The voltage was ramped continuously from −60 mV to +60 mV over 50 ms in the absence of ligand. An example of a WT current response is shown in FIG. 1A. The background conductance was measured from the slope of the resistive current ramp and normalized by the mean membrane capacitance of each receptor, which could be calculated from the capacitive current offset. GluCl WT and WT-XFP receptors showed minimal background conductance that was not different from a mock-transfected control (FIG. 1B). The two L9' mutations with the smallest side-chains, L9'A and L9'G, had the largest background conductance which was significantly different from WT receptors. (Frazier S J. (2012) Optimization of the GluCl/IVM Neuronal Silencing Tool via Protein Engineering. PhD Thesis, California Institute of Technology).

The example of the conversion of the wild-type GluCl channel to a channel with spontaneous channel activity or constitutively open channel or Cl⁻ pore by amino acid substitutions at the L9' as described above is meant as an exemplary embodiment. Similar modifications can be designed and tested to convert any channel in the Cys-loop receptor family, and in particular the glycine receptor (GlyR) chloride channel, the $GABA_A$ and $GABA_C$ receptors, but more generally any ion channel from any biological organism. Specific examples of mutations to some of the conserved amino acids of the α,β,γ and ρ-subunits of the $GABA_A$ and $GABA_C$ receptors shown to result in spontaneous opening of the chloride channel, resulting in a constitutively active channel, are described in Table 3.

TABLE 3

| Receptor | Subunit | Mutation | Ref |
| --- | --- | --- | --- |
| $GABA_A$ | β | L259S | Thompson et al., 1999 |
| $GABA_C$ | ρ | T314A | Pan et al., 1997 |
| $GABA_C$ | ρ | L317A | Pan et al., 1997 |
| $GABA_C$ | ρ | L301A | Chang and Weiss. 1998 |
| $GABA_C$ | ρ | L301G | Chang and Weiss, 1998 |
| $GABA_C$ | ρ | L301S | Chang and Weiss, 1998 |
| $GABA_C$ | ρ | L301T | Chang and Weiss, 1998 |
| $GABA_C$ | ρ | L301V | Chang and Weiss, 1998 |
| $GABA_C$ | ρ | L301Y | Chang and Weiss, 1998 |
| $GABA_A$ | α | L263S | Chang and Weiss, 1999 |
| $GABA_A$ | β | L259S | Chang and Weiss, 1999 |
| $GABA_A$ | γ | L274S | Chang and Weiss, 1999 |

Table 3. Mutations to leucine and tyrosine residues within the channel pore that have been documented to result in increased spontaneous activity of the $GABA_A$ and $GABA_C$ receptor resulting in constitutively active chloride channels. (Chang Y. and Weiss DS. (1999) Biophys J. 77:2542-2551; Thompson S A. et al. (1999) Br J Pharmacol. 127:1349-1358; Chang Y. and Weiss D S. (1998) Mol Pharmacol. 53:511-523; Pan Z H. et al. (1997) Proc Natl Acad Sci USA 94:6490-6495).

Accordingly, in certain embodiments, the constitutively active ion channel is a constitutively active GluCl ion channel. In certain embodiments, the subunit is an α-subunit, wherein the α-subunit can multimerize to form a constitutively active GluCl ion channel. In certain embodiments, the subunit comprises at least one mutation in the subunit's M2 domain as described in Table 2. In certain embodiments, the at least one mutation is L9'A or L9'G as described in Table 2.

In certain embodiments, the constitutively active ion channel is a constitutively active GlyR. In certain embodiments, the subunit is an α-subunit (e.g., alpha-1), wherein the α-subunit can multimerize to form a constitutively active GlyR ion channel. In certain embodiments, the subunit comprises at least one mutation in the subunit's M2 domain as described in Table 2. In certain embodiments, the at least one mutation is L9'A or L9'G as described in Table 2.

In certain embodiments, the constitutively active ion channel is a constitutively active $GABA_A$ receptor. In certain embodiments, the constitutively active ion channel is a constitutively active $GABA_C$ receptor. In certain embodiments the subunit is an α-, β- or γ-subunit, and wherein the α-, β- or γ-subunit can multimerize to form a constitutively active $GABA_A$ receptor. In certain embodiments, the subunit is a ρ-subunit, and wherein the ρ-subunit can multimerize to form a constitutively active $GABA_C$ receptor. In certain embodiments, the subunit comprises at least one mutation as described in Table 3. Thus, in certain embodiments, the encoded subunit is a $GABA_A$ α-subunit with at least one mutation at L263 (e.g., L263S), a $GABA_A$ β-subunit with at least one mutation at L259 (e.g., L259S), a $GABA_A$γ-subunit with at least one mutation at L274 (e.g., L274S) or a $GABA_C$ ρ-subunit with at least one mutation at T314 (e.g., T314A), L317 (e.g., L317A) or L301 (e.g., L301A, L301G, L301S, L301T, L301V, L301Y). Additionally, corresponding mutations may also be made in subunits from other types of ion channels; such corresponding amino acids may be identified by one skilled in the art using sequence alignment programs.

Promoters

In certain embodiments, an expression cassette described herein may further comprise a promoter. In certain embodiments, the promoter is operably linked to the nucleic acid. The promoter may be selected to drive expression of the ion channel subunit within a targeted set of cells. This may confer specificity to a targeted tissue. Thus, in certain embodiments, the promoter is a tissue specific promoter.

For example, if the targeted cell type is neuronal, as would be the case for the treatment of pain (sensory neurons) or spasticity (motor neurons), the selected promoter could be the pan-neuronal human synapsin-1 promoter (Syn1, or hSyn) (Iyer S M. et al. (2014) Nature Biotechnology 32(3): 274-278). Alternatively, a ubiquitous promoter may be utilized, such as the human cytomegalovirus ("CMV") promoter or the chicken beta-actin ("CBA") promoter, each of which is not neural specific, and each of which has been utilized safely in gene therapy trials for neurodegenerative disease.

When targeting skeletal muscle cells for the treatment of spasticity, the human cytomegalovirus ("CMV") promoter, the chicken beta-actin ("CBA") promoter or a muscle-specific desmin promoter could be used, for example (Childers M. et al. (2014) Sci Transl Med. 6(220): 220ra210; Falk D J. et al. (2015) Molecular Therapy—Methods & Clinical Development 2: 15007).

When targeting the trabecular meshwork (TM) for the treatment of ocular hypertension, targeted gene expression via AAV-mediated gene transfer into the TM cells of the outflow pathway has previously been demonstrated using promoter fragments from the matrix Gla protein (MGP) gene (Gonzalez P. et al. (2004) Invest Ophthalmol Vis Sci. 45:1389-1395). Selective targeting has also been achieved using the 5' promoter region of the chitinase 3-like 1 (Ch3L1) gene, with expression specifically directed to the outermost anterior and posterior regions of the TM (Liton P B. et al. (2005) Invest Ophthalmol Vis Sci. 46:183-190). Further, numerous gene profiling studies of the trabecular meshwork have been published, providing additional alternative configurations for trabecular meshwork cell-selective promoters (Gonzalez P. et al., (2000) Invest Ophthalmol Vis Sci. 41:3678-3693; Wirtz, et al. (2002) Invest Ophthalmol Vis Sci. 43:3698-3704; Tomarev, et al. (2003) Invest Ophthalmol Vis Sci. 44:2588-2596; Liton, et al. (2006) Mol Vis. 12:774-790; Fan, et al. (2008) Invest Ophthalmol Vis Sci. 49:1886-1897; Fuchshofer, et al. (2009) Exp Eye Res. 88:1020-1032; Paylakhi, et al. (2012) Mol Vis. 18:241-254; Liu, et al. (2013) Invest Ophthalmol Vis Sci. 54:6382-6389).

Accordingly, in certain embodiments, the promoter may be any promoter as described herein. In certain embodiments, the promoter is a regulatable promoter. In certain embodiments, the promoter is a constitutive promoter.

In certain embodiments, the promoter is selected from the group consisting of human synapsin-1 promoter (Syn1, or hSyn), human cytomegalovirus ("CMV") promoter, chicken beta-actin ("CBA") promoter, muscle-specific desmin promoter, matrix Gla protein (MGP) promoter or a fragment thereof and the 5' promoter region of the chitinase 3-like 1 (Ch3L1) gene.

In certain embodiments, the promoter is a selective promoter designed to limit the expression of the ion channel/subunit to a particular cell type. Thus, in certain embodiments, the promoter is a selective promoter designed to limit the expression of the ion channel/subunit (e.g., constitutively active ion channel) to the cells of the trabecular meshwork and/or other cells associated with the drainage of aqueous humor. In certain embodiments, the promoter is a selective promoter designed to limit the expression of the ion channel/subunit (e.g., constitutively active ion channel) to neuronal cells (e.g., human synapsin promoter (hSyn)). In certain embodiments, the promoter is a selective promoter designed to limit the expression of the ion channel/subunit (e.g., constitutively active ion channel) to muscle cells (e.g., desmin promoter).

In certain embodiments, the expression cassette further comprises a marker gene (e.g., a gene encoding a fluorescent protein, such as GFP or YFP).

In certain embodiments, the expression cassette further comprises an expression control sequence (e.g., an enhancer) operably linked to the nucleic acid sequence. Expression control sequences and techniques for operably linking sequences together are well known in the art.

Cells

Certain embodiments of the invention provide a cell comprising an expression cassette described herein. In certain embodiments, the cell is a mammalian cell, such as a cell located in the eye (e.g., a trabecular meshwork cell), a cell located in the peripheral nervous system (e.g., a nociceptive afferent neuronal cell) or a muscle cell. In certain embodiments, the expression cassette is contained in a vector. In certain embodiments, the vector is an adenoviral, lentiviral, adeno-associated viral (AAV), poliovirus, HSV, or murine Maloney-based viral vector. In certain embodiments, the vector is an AAV6 viral vector.

Vectors

Any suitable method can be employed to cause or induce exogenous expression of the ion channel subunit (e.g., a subunit of a chloride channel, such as GlyR or GluCl) in a mammal (e.g., a mammalian cell, such as an excitable cell). For example, an agent can be administered to the mammal that activates transcription of a gene encoding the subunit from the genome of the excitable cell. However, typically, exogenous expression of the ion channel subunit is caused or induced by gene transfer technology.

Accordingly, certain embodiments of the invention provide a vector comprising an expression cassette described herein. Additionally, certain embodiments provide contacting/introducing a vector described herein into an excitable cell (e.g., a mammalian excitable cell). Certain embodiments also comprise administering a vector described herein to a mammal (e.g., for expression in an excitable cell).

Any suitable vector may be used for introducing an expression cassette described herein into a mammalian cell (e.g., an excitable cell). Examples of suitable vectors include plasmids, liposomes, molecular conjugates (e.g., transferrin), and viruses.

In certain embodiments, the vector is a viral vector. Viral expression systems have the dual advantages of fast and versatile implementation combined with high infective/copy number for robust expression levels in targeted anatomy. Viral expression techniques, such as those comprising delivery of DNA encoding a desired promoter-protein sequence packaged within a recombinant viral vector, have been utilized with success in mammals to effectively transfect a targeted anatomy. They deliver genetic material to the nuclei of targeted cells, thereby inducing such cells to produce the desired protein, for example a subunit of an ion channel, such as GluCl, GlyR or other chloride channel proteins. In the case of an ion channel, these proteins are then transported to the cell membrane.

Suitable viral vectors include, for example, retroviral vectors, herpes virus based vectors and parvovirus based vectors (e.g., adeno-associated virus (AAV) based vectors, AAV-adenoviral chimeric vectors, and adenovirus-based vectors). In certain embodiments, the vector is an adenoviral, lentiviral, adeno-associated viral (AAV), self-complementary AAV (scAAV), poliovirus, HSV, or murine Maloney-based viral vector. In certain embodiments, the vector is an AAV vector. In certain embodiments, the vector is an AAV vector with known tropism for a specific type of targeted excitable cell. In certain embodiments, the AAV vector is selected from the group consisting of AAV1, AAV2, AAV3, AAV5, AAV6, AAV8, AAV9 and rAAV2/6. In certain embodiments, the vector is an AAV6 viral vector.

As described herein, a vector of the invention may comprise an expression cassette, wherein the expression cassette comprises a nucleic acid encoding a subunit of a multimeric ion channel (e.g., a subunit of GlyR or GluCl). In certain embodiments, the expression cassette may further comprise a selective promoter, which drives the expression of the protein only in a desired cell population. Following inoculation of a site on the skin, muscle, joint, eye, or other peripheral site, viral vectors (e.g., AAV) infect one or more cells (e.g., excitable cells), which facilitates expression of the encoded protein (e.g., a subunit of GlyR or GluCl) within the infected cell. However, because such vectors are typically replication-defective, they do not replicate within the cell to spread to other areas. Thus, if an AAV vector with selective tropism was employed to deliver the nucleic acid encoding the subunit, a site of inoculation could be selected to target treatment to a pre-selected area of the mammal.

By way of a non-limiting example, in the case of a GlyR chloride channel configuration, typically a viral vector will package what may be referred to as a "GlyR chloride channel expression cassette", which will contain the DNA encoding a subunit of a GlyR chloride channel and a promoter that will be selected to drive expression of the GlyR chloride channel protein. In the case of adeno-associated virus (AAV), the gene of interest (in this example a GlyR chloride channel subunit) can be in a single stranded configuration with only one active chloride channel expression cassette.

In the case of GluCl or GlyR chloride channel configurations and packaging the expression cassette within an AAV vector, several configurations may be used. AAVs are defective parvoviruses that contain a 4.7 kb single-stranded (ss) DNA flanked by inverted terminal repeats. They require a helper adenovirus for infection, and their genome encodes the AAV proteins needed for replicating and packaging. On entering the cell, the viral ss DNA is converted into a transcriptionally active double-stranded DNA by host enzymes. A recombinant AAV vector replaces the DNA encoding both of its viral proteins by a transgene expression cassette and therefore does not contain any open viral reading frames. This replacement allows transgene insert sizes of approximately 4.5 kb (4500 base pairs (bp)) (Buie L K. et al. (2010) Invest Ophthalmol Vis Sci. 51; 1:236-48). Based on the following gene coding sequence sizes, examples of expression cassettes comprising nucleic acids encoding GluCl and GlyR subunits that could be packaged into an AAV viral vector are shown below: the alpha and beta subunits of the GluCl (channels described below) are approximately 1400 bp; the GlyR alpha subunit is ~1200 bp; the gene coding sequence size of the human synapsin (hSyn)) promoter is approximately 500 bp; and that of the commonly used expression reporter, monomeric yellow fluorescent protein (mYFP), is 720 bp.

Examples of Expression Cassettes Comprising GluCl
1. hSyn promoter+GluCl-α subunit (~2 Kb)
2. hSyn promoter+GluCl-β subunit (~2 Kb)
3. hSyn promoter+GluCl-α subunit+mYFP (~2.7 Kb)
4. hSyn promoter+GluCl-β subunit+mYFP (~2.7 Kb)
5. hSyn promoter+GluCl-α subunit+hSyn promoter+GluCl-β subunit (~4 Kb)

And possibly:
6. hSyn promoter+GluCl-α subunit+hSyn promoter+GluCl-β subunit+mYFP (~4.7 Kb)

Examples of Expression Cassettes Comprising GlyR
1. hSyn promoter+GlyR-α subunit (~1.7 Kb)
2. hSyn promoter+GlyR-α subunit+mYFP (~2.4 Kb)

In a self-complementary AAV (scAAV) structure, two copies of the expression cassette complimentary in sequence with one another and connected by a hairpin loop are encapsulated within the viral envelope. The scAAVs are thought to be more stable and show higher expression levels especially in some cells, for example trabecular meshwork cells. The scAAV expression cassette's size is reduced from the original 4.5 to 2.2 kb (Buie L K. et al. (2010) Invest Ophthalmol Vis Sci. 51; 1:236-48). Given the size limitation of the scAAV, GluCl expression cassette configurations 1 or 2 (above) and possibly 3 or 4 (above) can be packaged into a scAAV viral vector. However, either of the GlyR expression cassette configurations 1 or 2 (above) can be packaged into a scAAV viral vector.

In the above descriptions of the expression cassettes above, the GluCl and the GlyR receptors were used as non-limiting examples. Similar expression cassettes can be designed and utilized for the transfection of $GABA_A$ and $GABA_C$ receptors. Additionally, expression of a gene product may be targeted by different serotypes of the virus (conferred by the viral capsid or coat proteins); different serotypes show different tissue tropism. For example a virus (e.g., AAV) virus could be designed to target a specific cell type (e.g., a sensory neuron, such as a nociceptive neuron).

Viruses have been utilized to target many tissue structures and systems both in the central nervous system and in the periphery. For example, gene transfer to nociceptors is a promising strategy for the management of chronic pain, allowing expression of a transgene at restricted sites in the nervous system, and thereby selectively targeting pain-related pathways without eliciting off-target effects.

Gene transfer to nociceptive neurons has been achieved through both viral and non-viral methods. Plasmid DNA driving expression of proteins have been delivered to sensory neurons via liposomes (Meuli-Simmen C. et al. (1999) Hum Gene Ther. 10:2689-700), electroporation (Lin C R. et al. (2002) Neurosci Lett. 317:1-4) and delivery through hypertonic diluent (Milligan E D. et al. (2006) Pain 126: 294-308) through peripheral or direct injections to the central nervous system. The major drawback of these methods is that they result in transient protein expression persisting no longer than two weeks. Alternatively, viruses can be used to drive longer transgene expression. The efficacy of viral-mediated gene delivery depends primarily on the type of delivery method and the type of virus being used. Adenovirus, herpes-simplex virus (HSV), lentivirus and adeno-associated virus (AAV) have been reported to deliver transgenes to nociceptive pathways through a number of delivery routes including subcutaneous (Wilson S P. et al. (1999) Proc Natl Acad Sci USA 96:3211-6; Goss, J R. et al. (2010) Molecular Therapy 19(3): 500-506; U.S. Pat. No. 8,957,036), intramuscular (Ghadge G D. et al. (1995) Gene Ther. 2:132-7), intraneural (Palmer J A. et al. (2000) J Virol. 74:5604-18), intrathecal (Storek B. et al. (2006) Mol Pain 2:4; Storek B. et al, (2008) Proc Natl Acad Sci USA 105:1055-60, intraspinal (Pezet S. et al. (2006) Mol Ther. 13:1101-9; Meunier A. et al. (2008) J Neurosci Methods 167:148-59, direct dorsal root ganglia injections (Xu Y. et al. (2003) Hum Gene Ther. 14:897-906) and also topical applications of the virus in the case of HSV (Antunes Bras J M. et al. (1998) J Neurochem. 70:1299-303; Zhang G. et al. (2008) Anesthesiology 108:305-13. While these studies have resulted in transgene expression at favorable sites and with concomitant reduction in pain-related behavior, the transduction profile has not often been characterized. This is common in studies that utilize secreted transgenes that act in the extracellular environment, such as enkephalin, endomorphins and interleukins, where only a few transduced cells are required to deliver the transgene to the affected cellular neighborhood and modulate pain perception (Mata M. et al. (2008). Curr Gene Ther. 8:42-8).

In 2009, Towne et al. assessed recombinant AAV (rAAV) serotype 6 as a gene transfer tool to target cellular mechanisms involved in the generation and development of chronic pain in mice. rAAVs are powerful gene transfer vectors due to their broad tissue tropism, efficient and stable transduction (>years), low immunogenicity and ability to infect post-mitotic cells in vivo (Mandel R J. et al. (2006) Mol Ther. 13:463-83). The serotype 6 vector (rAAV2/6) was chosen from the observation of sensory fiber transduction following intravenous delivery in previous experiments in mice (Towne C. et al. (2008) Mol Ther. 16:1018-25) and the high tropism for neurons following direct injections into the central nervous system (Azeredo da Silveira S. et al. (2009) Hum Mol Genet. 18:872-87). Towne et al. delivered rAAV2/6 through various routes of administration and precisely mapped and compared the transduction profiles obtained within the dorsal root ganglia (DRG) and spinal cord (Towne C. et al. (2009) Molecular Pain 5(1): 52). The capacity of recombinant AAV serotype 6 (rAAV2/6) to deliver genes to DRG neurons was assessed. In addition the transduction of nociceptors through five different routes of administration was characterized in mice. Direct injection of rAAV2/6 expressing green fluorescent protein (eGFP) into the sciatic nerve resulted in transduction of up to 30% eGFP-positive cells of L4 DRG neurons in a dose-dependent manner. More than 90% of transduced cells were small and medium sized neurons (<700 $\mu m^2$), predominantly colocalized with markers of nociceptive neurons, and had eGFP-positive central terminal fibers in the superficial lamina of the spinal cord dorsal horn. The efficiency and profile of transduction was independent of mouse genetic background. Intrathecal administration of rAAV2/6 gave the highest level of transduction (approximately 60%) and had a similar size profile and colocalization with nociceptive neurons. Intrathecal administration also transduced DRG neurons at cervical and thoracic levels and resulted in comparable levels of transduction in a mouse model for neuropathic pain. Subcutaneous and intramuscular delivery resulted in low levels of transduction in the L4 DRG. Likewise, delivery via tail vein injection resulted in relatively few eGFP-positive cells within the DRG, however, this transduction was observed at all vertebral levels and corresponded to large non-nociceptive cell types. From these data they concluded that rAAV2/6 is an efficient vector to deliver transgenes to nociceptive neurons in mice. Furthermore, the characterization of the transduction profile may facilitate gene transfer studies to dissect mechanisms behind neuropathic pain.

These studies were later supported by Iyer et al. in 2014, who again used AAV6 as a delivery vector to selectively transfect afferent nociceptor nerves in mice with either excitatory or inhibitory opsins to generate or inhibit pain sensation, respectively in response to light (Iyer S M. et al. (2014) Nature Biotechnology 32(3): 274-278). These studies show that specific neuronal populations can be selectively targeted using specific AAV serotypes. In this case pain sensing neurons were selectively targeted using AAV6. These studies also demonstrate that AAV6 can be taken up by nociceptive afferent nerves following subcutaneous and intramuscular delivery. This strongly suggests that local injections into the site of the pain as in the case of intradermal or intra-articular injections for chronic joint pain is a viable route of delivery of an AAV-vectored gene therapy to specifically and selectively transfect the nociceptive nerves that locally innervate the painful area or joint without affecting other neuronal-mediated sensations from the same limb (such as touch) or motor activity in that limb.

The overall result of this approach would be akin to a very-long-lasting (could have a duration of many years) anesthetic effect of a local anesthetic delivered via an intradermal, subcutaneous or intra-articular route. Today it is common practice to inject local anesthetics into the skin or intra-articularly for example in the sacroiliac joint—also known as a sacroiliac joint block (Rupert M. et al. (2009) Pain Physician 12(2): 399-418).

In another embodiment, a gene product (e.g., an ion channel subunit) may be targeted to structures within the eye. Lenti- and adeno-associated (AAV) viral vectors have been utilized successfully to introduce genes into the mouse, rat and primate eye (Borrás T. et al. (2002) Invest Ophthalmol Vis Sci. 43(8): 2513-2518). Additionally, these have been well tolerated and highly expressed over relatively long periods of time with no reported adverse effects, providing the opportunity for long-term treatment paradigms.

Viruses have been utilized to target many tissue structures and systems, including but not limited to ciliary epithelium, ciliary muscle retinal ganglion cells as well as trabecular meshwork cells. To date, at least six delivery systems have been tested for ability to deliver genes to the relevant tissues or cells. These include adenoviruses (Ads), adeno-associated viruses (AAVs), herpes simplex viruses (HSVs), lentiviruses (LVs; feline immunodeficiency virus [FIV] and human immunodeficiency virus [HIV]), liposomes (LPs), and naked DNA. Of these, AAV may be a preferred vector due to its safety profile. However, literature reports suggest that self-complementary AAV may be more effective at infecting TM cells than traditional single-stranded DNA containing AAV. Accordingly, in certain embodiments, wherein genetic material is to be expressed in the trabecular meshwork for the treatment of ocular hypertension, the viral vector may be a self-complementary AAV2 (scAAV2). This vector has shown to be effective in targeting and effecting-long term expression of green fluorescent protein (GFP) in trabecular meshwork cells in the eyes of mice and primates (Buie L K. et al. (2010) Invest Ophthalmol Vis Sci. 51; 1:236-48).

As discussed herein, a vector of the invention (e.g., comprising an expression cassette comprising a nucleic acid encoding a GlyR or GluCl subunit) may be used for the treatment of spasticity. In certain embodiments, expression of the subunit may be targeted to either the muscle or motor neurons or both as required to bring about the desired effect. In the case of where genetic material is to be expressed in motor neurons for the treatment of spastic hypertonia (spasticity) for example, the vector may be an AAV6 vector injected into the muscle or at the neuromuscular junction of the muscle that is to be relaxed. This vector has shown to be effective in targeting and effecting-long term expression of green fluorescent protein (GFP) in the motor neuron cells in non-human primates (Towne C. et al. (2010) Gene Therapy 17(1): 141-6). In the case of where the subunit is to be expressed in skeletal muscle for the treatment of spastic hypertonia (spasticity) for example, the vector may be one of AAV types 1, 3, or 5 (Chao H. (2000) Molecular Therapy 2(6): 619-23) or AAV8 (Childers M. et al. (2014). Sci Transl Med. 6(220): 220ra210) or AAV9 (Falk D J. et al. (2015) Molecular Therapy—Methods & Clinical Development 2: 15007). These vectors have been shown to be effective in targeting and effecting-long term expression of canine factor IX in the skeletal muscle cells in NOD/SCIOD mice. The vector would be injected directly into the muscle that is to be treated.

Vector Preparation and Administration

After the vector described herein has been created, the vector may be purified. Vector purification to enhance the concentration of the vector in a composition can be accomplished by any suitable method, such as by density gradient purification, by chromatography techniques, or limiting dilution purification. The specific purification techniques are known to those versed in the art and will vary depending on the vector type (e.g., type of virus, such as type of AAV).

In certain embodiment of the invention, the vector is a viral vector, such as an AAV vector. Generally, a viral vector is most useful when enough of the virus can be delivered to a cell population to ensure that the cells are confronted with a predefined number of viruses. Thus, the present invention provides a stock, preferably a homogeneous stock, comprising the viral vector (e.g., AAV vector). The preparation and analysis of viral stocks (e.g., AAV stocks) is well known in the art. Viral stocks vary considerably in titer, depending largely on viral genotype and the protocol and cell lines used to prepare them. In certain embodiments, such a stock has a viral titer of at least about $10^5$ plaque-forming units (pfu), such as at least about $10^6$ pfu or even more specifically at least about $10^7$ pfu. In still more specific embodiments, the titer can be at least about $10^8$ pfu, or at least about $10^9$ pfu. In certain embodiments, the stock is a high titer stock of at least about $10^{10}$ pfu or at least about $10^{11}$ pfu.

The invention additionally provides a composition comprising a vector described herein (e.g., an AAV vector) and a carrier. The carrier of the composition can be any suitable carrier for the vector. The carrier typically will be liquid, but also can be solid, or a combination of liquid and solid components. The carrier desirably is a pharmaceutically acceptable (e.g., a physiologically or pharmacologically acceptable) carrier (e.g., excipient or diluent). Pharmaceutically acceptable carriers are well known and are readily available. The choice of carrier will be determined, at least in part, by the particular vector and the particular method used to administer the composition. The composition can further comprise any other suitable components, especially for enhancing the stability of the composition and/or its end-use. Accordingly, there is a wide variety of suitable formulations of the composition of the invention. The following formulations and methods are merely exemplary and are in no way limiting.

As discussed above, the vectors described herein may be formulated as pharmaceutical compositions and administered to a mammalian host, such as a human patient in a variety of forms adapted to the chosen route of administration, i.e., orally or parenterally, by intravenous, intramuscular, topical or subcutaneous routes.

The vectors may be administered via intradermal, subcutaneous, intraneural, intramuscular or intracameral infusion or injection. Formulations suitable for local (regional) injection or parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Solutions of the vector can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms. The formulations can be presented in unit-dose or multi-dose sealed containers, such as ampules and vials, and can be stored in a freeze-dried (lyophilized) condition requiring only the addition of a sterile liquid excipient, for example, water, for injections, immediately prior to use. Extemporaneous injection solutions and suspensions can be prepared from sterile powders, granules, and tablets of the kind previously described.

The pharmaceutical dosage forms suitable for injection or infusion can include sterile aqueous solutions or dispersions or sterile powders comprising the vector which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the vector in the required amount in the appropriate solvent with various of the other ingredients enumerated above, as required, followed by sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

The present vectors may also be administered topically in combination with a pharmaceutically acceptable vehicle such as an inert diluent. For topical administration, the present vectors may be applied in pure form, i.e., when they are liquids. However, it will generally be desirable to administer them to the skin as compositions or formulations, in combination with a dermatologically acceptable carrier, which may be a liquid.

Useful liquid carriers include water, alcohols or glycols or water-alcohol/glycol blends, in which the present vectors can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the present vectors to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of a vector described herein can be determined by comparing their in vitro activity, and in vivo activity in animal models. Methods for the extrapolation of effective dosages in mice, and other animals, to humans are known to the art; for example, see Nathwani A C. et al. (2011) Mol Ther. 19:876-885; Nathwani A C. et al. (2014) N Engl J Med. 371(21): 1994-2004.

The amount of the vector, required for use in treatment will vary with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as application of a plurality of drops onto the eye.

As discussed herein, a vector may be administered in combination with other therapeutic agents or biologically-active agents, for example, other agents that are useful for treating an excitable cell-related disease or condition, such as pain, inflammation, ocular hypertension or spastic hypertonia. Additionally, immune system suppressors, enhancers, antibiotics, or adrenaline may be administered in combination with a vector described herein. Accordingly, in one embodiment the invention also provides a composition comprising a vector as described herein, at least one other therapeutic agent or biologically active agent, and a pharmaceutically acceptable diluent or carrier. For example, therapeutic factors useful in the treatment of a particular indication can be present. Factors that control inflammation, such as ibuprofen or steroids, can be part of the composition to reduce swelling and inflammation associated with in vivo administration of the vector and physiological distress. Immune system suppressors can be administered with the composition method to reduce any immune response to the vector itself or associated with a disorder. Alternatively, immune enhancers can be included in the composition to upregulate the body's natural defenses against disease. Antibiotics, i.e., microbicides and fungicides, can be present to reduce the risk of infection associated with gene transfer procedures and other disorders. Additionally pharmacologically active agents such as adrenaline can be added to the formulation to induce vasoconstriction and reduce clearance of the AAV from the injection site as used for local anesthetics. The invention also provides a kit comprising a vector as described herein, at least one other therapeutic agent or biologically active agent, packaging material, and instructions for administering a vector as described herein and the other therapeutic/biologically active agent or agents to an animal to treat an excitable cell-related disease or condition.

Certain Embodiments of the Invention

Embodiment 1

A vector comprising an expression cassette, wherein the expression cassette comprises a promoter operably linked to a nucleic acid encoding a subunit of a multimeric ion channel (e.g., chloride channel), for the in vivo modulation of a mammalian cell's electrophysiological activity.

Embodiment 2

A method for the in vivo modulation of a mammalian cell's electrophysiological activity comprising contacting the cell with a vector comprising an expression cassette comprising a promoter operably linked to a nucleic acid encoding a subunit of a multimeric ion channel (e.g., chloride channel).

Embodiment 3

A vector comprising an expression cassette, wherein the expression cassette comprises a promoter operably linked to a nucleic acid encoding a subunit of a multimeric ion channel, for the prophylactic or therapeutic treatment of an excitable cell-related disease or condition.

Embodiment 4

A method of treating an excitable cell-related disease or condition in a mammal in need thereof, comprising administering to the mammal an effective amount of a vector comprising an expression cassette, wherein the expression cassette comprises a promoter operably linked to a nucleic acid encoding a subunit of a multimeric ion channel.

Embodiment 5

The vector or method of any one of embodiments 1-4, wherein the subunit is capable of forming a multimeric ion channel by multimerizing with one or more additional subunits.

Embodiment 6

The vector or method of any one of embodiments 1-5, wherein treatment is in the absence of the administration of an agonist or allosteric modulator; wherein an agonist or allosteric modulator of the multimeric ion channel is not administered to the mammal; and/or wherein the mammalian cell is not contacted with an exogenous agonist or an exogenous allosteric modulator.

Embodiment 7

The vector or method of embodiment 6, wherein the agonist is glycine.

Embodiment 8

The vector or method of any one of embodiments 1-7, wherein the multimeric ion channel is activated by an endogenous agonist.

Embodiment 9

The vector or method of any one of embodiments 1-8, wherein the nucleic acid encodes a subunit of a chloride channel.

Embodiment 10

The vector or method of embodiment 9, wherein the nucleic acid encodes a subunit of a glycine receptor (GlyR), a γ-aminobutyric acid receptor ($GABA_AR$) or a glutamate-gated chloride channel (GluCl).

Embodiment 11

The vector or method of embodiment 10, wherein the nucleic acid encodes a subunit of a GlyR.

Embodiment 12

The vector or method of embodiment 11, wherein the encoded GlyR subunit is selected from the group consisting of an alpha-1 subunit, an alpha-2 subunit, and alpha-3 subunit, an alpha-4 subunit and a beta-subunit.

Embodiment 13

The vector or method of embodiment 12, wherein the encoded GlyR subunit is an alpha-1-subunit of GlyR (GlyRa1).

Embodiment 14

The vector or method of embodiment 13, wherein the encoded GlyR subunit is human GlyRa1 (hGlyRa1).

Embodiment 15

The vector or method of embodiment 10, wherein the nucleic acid encodes a subunit of a $GABA_AR$.

Embodiment 16

The vector or method of embodiment 15, wherein the nucleic acid encodes a subunit of a $GABA_{A-\rho}$ receptor.

Embodiment 17

The vector or method of embodiment 15, wherein the encoded $GABA_AR$ subunit is selected from the group consisting of GABRA1 ($\alpha_1$), GABRA2 ($\alpha_2$), GABRA3 ($\alpha_3$), GABRA4 ($\alpha_4$), GABRA5 ($\alpha_5$), GABRA6 ($\alpha_6$), GABRB1 ($\beta_1$), GABRB1 ($\beta_2$), GABRB1 ($\beta_3$), GABRG1 ($\gamma_1$), GABRG2 ($\gamma_2$), GABRG3 ($\gamma_3$), GABRD ($\delta$), GABRE ($\epsilon$), GABRP ($\pi$), GABRQ ($\theta$), GABRR1 ($\rho_1$), GABRR2 ($\rho_2$) and GABRR3 ($\rho_3$).

Embodiment 18

The vector or method of embodiment 10, wherein the nucleic acid encodes a subunit of a GluCl.

Embodiment 19

The vector or method of embodiment 18, wherein the encoded GluCl subunit is selected from the group consisting of $\alpha_1$, $\alpha_{2A}$, $\alpha_{2B}$, GBR2A ($\alpha_{3A}$), GBR2B ($\alpha_{3B}$) and β.

Embodiment 20

The vector or method of any one of embodiments 1-19, wherein the encoded subunit comprises at least one mutation as compared to a corresponding wildtype subunit.

Embodiment 21

The vector or method of embodiment 20, wherein a multimeric ion channel comprising the mutant subunit is constitutively active.

Embodiment 22

The vector or method of embodiment 20, wherein a multimeric ion channel comprising the mutant subunit has enhanced agonist sensitivity as compared to a corresponding wildtype multimeric ion channel.

Embodiment 23

The vector or method of any one of embodiments 20-22, wherein the encoded subunit comprises an M2 transmembrane domain and the at least one mutation is in the M2 transmembrane domain, as compared to a corresponding wildtype subunit.

Embodiment 24

The vector or method of embodiment 23, wherein the at least one mutation is at the leucine 9'residue, as compared to a corresponding wildtype subunit.

Embodiment 25

The vector or method of embodiment 24, wherein the at least one mutation is L9'A or L9'G as compared to a wildtype subunit.

Embodiment 26

The vector or method of any one of embodiments 20-22, wherein the encoded subunit is a $GABA_A$ α-subunit, wherein the at least one mutation is at L263; a GABA$_A$ β-subunit, wherein the at least one mutation is at L259; a GABA$_A$ γ-subunit, wherein the at least one mutation is at L274; or a GABA$_C$ ρ-subunit, wherein the at least one mutation is at T314, L317 or L301, as compared to a corresponding wildtype subunit.

Embodiment 27

The vector or method of any one of embodiments 20-26, wherein the encoded subunit has between about 80% sequence identity to about 99% sequence identity to a corresponding wildtype subunit.

Embodiment 28

The vector or method of embodiment 27, wherein the encoded subunit has at least 90% sequence identity to a corresponding wildtype subunit.

Embodiment 29

The vector or method of embodiment 28, wherein the encoded subunit has at least 95% sequence identity to a corresponding wildtype subunit.

Embodiment 30

The vector or method of embodiment 29, wherein the encoded subunit has about 99% sequence identity to a corresponding wildtype subunit.

Embodiment 31

The vector or method of any one of embodiments 1-30, wherein the promoter is a regulatable promoter.

Embodiment 32

The vector or method of any one of embodiments 1-30, wherein the promoter is a constitutive promoter.

Embodiment 33

The vector or method of any one of embodiments 1-30, wherein the promoter is a tissue specific promoter.

Embodiment 34

The vector or method of any one of embodiments 1-30, wherein the promoter is selected from the group consisting of a human synapsin-1 promoter (Syn1, or hSyn), a human cytomegalovirus ("CMV") promoter, a chicken beta-actin ("CBA") promoter, a muscle-specific desmin promoter, a matrix Gla protein (MGP) promoter or a fragment thereof and a 5' promoter region of a chitinase 3-like 1 (Ch3L1) gene.

Embodiment 35

The vector or method of any one of embodiments 1-34, wherein the vector is a viral vector.

Embodiment 36

The vector or method of embodiment 35, wherein the viral vector is an adenoviral, lentiviral, adeno-associated viral (AAV), self-complementary AAV (scAAV), poliovirus, HSV, or murine Maloney-based viral vector.

Embodiment 37

The vector or method of embodiment 36, wherein the viral vector is an AAV vector.

Embodiment 38

The vector or method of embodiment 37, wherein the AAV vector is selected from the group consisting of AAV1, AAV2, AAV3, AAV5, AAV6, AAV8, AAV9 and rAAV2/6.

Embodiment 39

The vector or method of embodiment 38, wherein the vector is an AAV6 vector.

Embodiment 40

The vector or method of embodiment 36, wherein the vector is a scAAV vector.

Embodiment 41

The vector or method of embodiment 40, wherein the scAAV vector is a scAAV2 vector.

Embodiment 42

The vector or method of any one of embodiments 3-41, wherein the excitable cell-related disease or condition is pain, inflammation, ocular hypertension or spastic hypertonia.

Embodiment 43

The vector or method of embodiment 42, wherein the excitable cell-related disease is pain.

Embodiment 44

The vector or method of embodiment 43, wherein the pain is chronic pain.

Embodiment 45

The vector or method of embodiment 43 or 44, wherein the pain is joint pain or neuropathic pain.

Embodiment 46

The vector or method of embodiment 42, wherein the excitable cell-related disease or condition is inflammation.

Embodiment 47

The vector or method of embodiment 46, wherein the inflammation is joint inflammation.

Embodiment 48

The vector or method of any one of embodiments 42-47, wherein the vector is an AAV6 vector, the promoter is a human synapsin (hSyn) promoter, and the nucleic acid encodes a GlyR subunit.

Embodiment 49

The vector or method of embodiment 48, wherein the GlyR subunit comprises at least one mutation that results in a constitutively active GlyR upon multimerization of the subunit.

Embodiment 50

The vector or method of embodiment 42, wherein the excitable cell-related disease or condition is ocular hypertension.

Embodiment 51

The vector or method of embodiment 50, wherein the excitable cell-related disease or condition is Glaucoma.

Embodiment 52

The vector or method of embodiment 50 or 51, wherein the vector is a scAAV2 vector, the promoter is a matrix Gla protein (MGP) promoter, and the nucleic acid encodes a GlyR subunit.

Embodiment 53

The vector or method of embodiment 52, wherein the GlyR subunit comprises at least one mutation that results in a constitutively active GlyR upon multimerization of the subunit.

Embodiment 54

The vector or method of embodiment 42, wherein the excitable cell-related disease or condition is spastic hypertonia.

Embodiment 55

The vector or method of embodiment 54, wherein the vector is an AAV2 or an AAV6 vector, the promoter is a human synapsin (hSyn) promoter, and the nucleic acid encodes a GlyR subunit.

Embodiment 56

The vector or method of embodiment 55, wherein the GlyR subunit comprises at least one mutation that results in a constitutively active GlyR upon multimerization of the subunit.

Embodiment 57

The vector or method of embodiment 54, wherein the vector is an AAV8 or an AAV9 vector, the promoter is a human cytomegalovirus ("CMV") promoter, a chicken beta-actin ("CBA") promoter or a CAG or muscle-specific desmin promoter, and the nucleic acid encodes a GlyR subunit.

Embodiment 58

The vector or method of embodiment 57, wherein the GlyR subunit comprises at least one mutation that results in a constitutively active GlyR upon multimerization of the subunit.

Embodiment 59

The vector or method of embodiment 57 or 58, wherein the vector is AAV8 and the promoter is a muscle-specific desmin promoter.

Embodiment 60

The method of any one of embodiments 4-59, further comprising administering to the mammal one or more other therapeutic agents.

Embodiment 61

The method of embodiment 60, wherein the one or more other therapeutic agents is an agent useful for treating pain, inflammation, ocular hypertension and/or spastic hypertonia.

Embodiment 62

The method of embodiment 60, wherein the one or more other therapeutic agents is not an agonist or an allosteric modulator of the multimeric ion channel.

Embodiment 63

The method of embodiment 62, wherein the one or more other therapeutic agents is not glycine.

Embodiment 64

A pharmaceutical composition for the prophylactic or therapeutic treatment of an excitable cell-related disease or condition, comprising a vector comprising an expression cassette, wherein the expression cassette comprises a promoter operably linked to a nucleic acid encoding a subunit of a multimeric ion channel, and a pharmaceutically acceptable carrier.

Embodiment 65

A combination of a) a vector comprising an expression cassette, wherein the expression cassette comprises a promoter operably linked to a nucleic acid encoding a subunit of a multimeric ion channel; and b) one or more other therapeutic agents; for the prophylactic or therapeutic treatment of an excitable cell-related disease or disorder.

Embodiment 66

The combination of embodiment 65, wherein the one or more other therapeutic agents is an agent useful for treating pain, inflammation, ocular hypertension and/or spastic hypertonia.

Embodiment 67

The combination of embodiment 65, wherein the one or more additional therapeutic agents is not an agonist or allosteric modulator of the multimeric ion channel.

Embodiment 68

The combination of embodiment 67, wherein the one or more additional therapeutic agents is not glycine.

Embodiment 69

A kit comprising a vector comprising an expression cassette, wherein the expression cassette comprises a promoter operably linked to a nucleic acid encoding a subunit of a multimeric ion channel; packaging material, and instructions for administering the vector to a mammal in need thereof to treat an excitable cell-related disease or condition.

Embodiment 70

The kit of embodiment 69, further comprising one or more other therapeutic agents.

Embodiment 71

The use of a vector comprising an expression cassette, wherein the expression cassette comprises a promoter operably linked to a nucleic acid encoding a subunit of a multimeric ion channel, to prepare a medicament for the treatment of an excitable cell-related disease or condition in a mammal in need thereof.

Embodiment 72

A vector comprising an expression cassette, wherein the expression cassette comprises a promoter operably linked to a nucleic acid encoding a subunit of a multimeric chloride channel for use in medical therapy.

Embodiment 73

A method of treating pain, inflammation, ocular hypertension or spastic hypertonia in a mammal in need thereof, comprising administering to the mammal an effective amount of a vector comprising an expression cassette, wherein the expression cassette comprises a promoter operably linked to a nucleic acid encoding a subunit of a GlyR (e.g., GlyRa1, e.g., hGlyRa1)).

Embodiment 74

A method of treating pain, inflammation, ocular hypertension or spastic hypertonia in a mammal in need thereof, comprising administering to the mammal an effective amount of a vector comprising an expression cassette, wherein the expression cassette comprises a promoter operably linked to a nucleic acid encoding a subunit of a GluCl (e.g., an alpha subunit of GluCl).

Embodiment 75

The method of embodiment 73 or 74, wherein an agonist or allosteric modulator is not administered to the mammal.

Embodiment 76

The method of any one of embodiments 73-75, wherein the encoded subunit comprises at least one mutation.

Embodiment 77

A nucleic acid comprising a sequence encoding an α-subunit of a glycine receptor (GlyR), wherein the α-subunit comprises at least one mutation that results in a constitutively active GlyR upon multimerization of the subunit.

Embodiment 78

The nucleic acid of embodiment 77, wherein the encoded α-subunit of GlyR is selected from the group consisting of an alpha-1 subunit, an alpha-2 subunit, and alpha-3 subunit and an alpha-4 subunit.

Embodiment 79

The nucleic acid of embodiment 77, wherein the encoded α-subunit of GlyR is a human α-subunit of GlyR.

Embodiment 80

The nucleic acid of embodiment 79, wherein the encoded α-subunit of GlyR is an alpha-1-subunit of GlyR (GlyRa1).

Embodiment 81

The nucleic acid of embodiment 79, wherein the encoded α-subunit of GlyR is human GlyRa1 (hGlyRa1).

Embodiment 82

The nucleic acid of any one of embodiments 77-81, wherein the encoded α-subunit of GlyR comprises an M2 transmembrane domain and the at least one mutation is in the M2 transmembrane domain (as compared to a corresponding wildtype α-subunit of GlyR).

Embodiment 83

The nucleic acid of embodiment 82, wherein the at least one mutation is at the leucine 9'residue (as compared to a corresponding wildtype α-subunit of GlyR).

Embodiment 84

The nucleic acid of embodiment 82, wherein, the at least one mutation is described in Table 2.

Embodiment 85

The nucleic acid of embodiment 82, wherein the at least one mutation is L9'A or L9'G (as compared to a corresponding wildtype α-subunit of GlyR).

Embodiment 86

The nucleic acid of embodiment 82, wherein the at least one mutation is L9'A.

Embodiment 87

The nucleic acid of embodiment 82, wherein the nucleic acid comprises a sequence having at least 80% sequence identity to SEQ ID NO:2.

Embodiment 88

The nucleic acid of embodiment 87, wherein the nucleic acid comprises a sequence having at least 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:2.

Embodiment 89

The nucleic acid of embodiment 87, wherein the nucleic acid comprises SEQ ID NO:2.

Embodiment 90

The nucleic acid of embodiment 87, wherein the nucleic acid consists of SEQ ID NO:2.

Embodiment 91

A polypeptide encoded by a nucleic acid described herein.

Embodiment 92

An expression cassette comprising a promoter operably linked to a nucleic acid described herein.

Embodiment 93

The expression cassette of embodiment 92, wherein the promoter is a regulatable promoter.

Embodiment 94

The expression cassette of embodiment 92, wherein the promoter is a constitutive promoter.

Embodiment 95

The expression cassette of embodiment 92, wherein the promoter is a tissue specific promoter.

Embodiment 96

The expression cassette of embodiment 92, wherein the promoter is selected from the group consisting of a human synapsin-1 promoter (Syn1, or hSyn), a human cytomegalovirus ("CMV") promoter, a chicken beta-actin ("CBA") promoter, a muscle-specific desmin promoter, a matrix Gla protein (MGP) promoter or a fragment thereof and a 5' promoter region of a chitinase 3-like 1 (Ch3L1) gene.

Embodiment 97

The expression cassette of embodiment 92, wherein the promoter is a human synapsin-1 promoter (hSyn).

Embodiment 98

A vector comprising an expression cassette described herein (e.g., as described in any one of embodiments 92-97).

Embodiment 99

The vector of embodiment 98, wherein the vector is a viral vector.

Embodiment 100

The vector of embodiment 99, wherein the viral vector is an adenoviral, lentiviral, adeno-associated viral (AAV), self-complementary AAV (scAAV), poliovirus, HSV, or murine Maloney-based viral vector.

Embodiment 101

The vector of embodiment 100, wherein viral vector is an AAV vector.

Embodiment 102

The vector of embodiment 101, wherein the AAV vector is selected from the group consisting of AAV1, AAV2, AAV3, AAV5, AAV6, AAV8, AAV9 and rAAV2/6.

Embodiment 103

The vector of embodiment 102, wherein the vector is an AAV6 vector.

Embodiment 104

A pharmaceutical composition comprising a vector described herein (e.g., as described in any one of embodiments 98-103) and a pharmaceutically acceptable carrier.

Embodiment 105

A viral stock comprising a vector as described herein.

Vectors of the invention (e.g., as described in any one of embodiments 98-103) may be used in the methods of the invention described herein.

DNA and protein sequences are shown below for the human GlyRa1 subunit. Both wildtype and the L9'A mutant sequences are shown for each. Additionally, the sequences for the M2 domain are also included.

Nucleic Acid Sequences

```
Human GlyRa1 Wild-Type
                                          (SEQ ID NO: 1)
ATGTACAGCTTCAATACTCTTCGACTCTACCTTTGGGAGACCATTGTAT

TCTTCAGCCTTGCTGCTTCTAAGGAGGCTGAAGCTGCTCGCTCCGCACC

CAAGCCTATGTCACCCTCGGATTTCCTGGATAAGCTAATGGGGAGAACC

TCCGGATATGATGCCAGGATCAGGCCCAATTTTAAAGGTCCCCCAGTGA

ACGTGAGCTGCAACATTTTCATCAACAGCTTTGGTTCCATTGCTGAGAC

AACCATGGACTATAGGGTCAACATCTTCCTGCGGCAGCAATGGAACGAC

CCCCGCCTGGCCTATAATGAATACCCTGACGACTCTCTGGACCTGGACC

CATCCATGCTGGACTCCATCTGGAAACCTGACCTGTTCTTTGCCAACGA

GAAGGGGGCCCACTTCCATGAGATCACCACAGACAACAAATTGCTAAGG

ATCTCCCGGAATGGGAATGTCCTCTACAGCATCAGAATCACCCTGACAC

TGGCCTGCCCCATGGACTTGAAGAATTTCCCCATGGATGTCCAGACATG

TATCATGCAACTGGAAAGCTTTGGATATACGATGAATGACCTCATCTTT

GAGTGGCAGGAACAGGGAGCCGTGCAGGTAGCAGATGGACTAACTCTGC

CCCAGTTTATCTTGAAGGAAGAGAAGGACTTGAGATACTGCACCAAGCA

CTACAACACAGGTAAATTCACCTGCATTGAGGCCCGGTTCCACCTGGAG

CGGCAGATGGGTTACTACCTGATTCAGATGTATATTCCCAGCCTGCTCA

TTGTCATCCTCTCATGGATCTCCTTCTGGATCAACATGGATGCTGCACC

TGCTCGTGTGGGCCTAGGCATCACCACTGTGCTCACCATGACCACCCAG

AGCTCCGGCTCTCGAGCATCTCTGCCCAAGGTGTCCTATGTGAAAGCCA
```

-continued

TTGACATTTGGATGGCAGTTTGCCTGCTCTTTGTGTTCTCAGCCCTATT

AGAATATGCTGCCGTTAACTTTGTGTCTCGGCAACATAAGGAGCTGCTC

CGATTCAGGAGGAAGCGGAGACATCACAAGAGCCCCATGTTGAATCTAT

TCCAGGAGGATGAAGCTGGAGAAGGCCGCTTTAACTTCTCTGCCTATGG

GATGGGCCCAGCCTGTCTACAGGCCAAGGATGGCATCTCAGTCAAGGGC

GCCAACAACAGTAACACCACCAACCCCCCTCCTGCACCATCTAAGTCCC

CAGAGGAGATGCGAAAACTCTTCATCCAGAGGGCCAAGAAGATCGACAA

AATATCCCGCATTGGCTTCCCCATGGCCTTCCTCATTTTCAACATGTTC

TACTGGATCATCTACAAGATTGTCCGTAGAGAGGACGTCCACAACCAGT

GA

*The codon for the L9' residue is shown in bold.

Human GlyRal L9'A mutein
(SEQ ID NO: 2)

ATGTACAGCTTCAATACTCTTCGACTCTACCTTTGGGAGACCATTGTAT

TCTTCAGCCTTGCTGCTTCTAAGGAGGCTGAAGCTGCTCGCTCCGCACC

CAAGCCTATGTCACCCTCGGATTTCCTGGATAAGCTAATGGGGAGAACC

TCCGGATATGATGCCAGGATCAGGCCCAATTTTAAAGGTCCCCCAGTGA

ACGTGAGCTGCAACATTTTCATCAACAGCTTTGGTTCCATTGCTGAGAC

AACCATGGACTATAGGGTCAACATCTTCCTGCGGCAGCAATGGAACGAC

CCCCGCCTGGCCTATAATGAATACCCTGACGACTCTCTGGACCTGGACC

CATCCATGCTGGACTCCATCTGGAAACCTGACCTGTTCTTTGCCAACGA

GAAGGGGGCCCACTTCCATGAGATCACCACAGACAACAAATTGCTAAGG

ATCTCCCGGAATGGGAATGTCCTCTACAGCATCAGAATCACCCTGACAC

TGGCCTGCCCCATGGACTTGAAGAATTTCCCCATGGATGTCCAGACATG

TATCATGCAACTGGAAAGCTTTGGATATACGATGAATGACCTCATCTTT

GAGTGGCAGGAACAGGGAGCCGTGCAGGTAGCAGATGGACTAACTCTGC

CCCAGTTTATCTTGAAGGAAGAGAAGGACTTGAGATACTGCACCAAGCA

CTACAACACAGGTAAATTCACCTGCATTGAGGCCCGGTTCCACCTGGAG

CGGCAGATGGGTTACTACCTGATTCAGATGTATATTCCCAGCCTGCTCA

TTGTCATCCTCTCATGGATCTCCTTCTGGATCAACATGGATGCTGCACC

TGCTCGTGTGGGCCTAGGCATCACCACTGTGGCCACCATGACCACCCAG

AGCTCCGGCTCTCGAGCATCTCTGCCCAAGGTGTCCTATGTGAAAGCCA

TTGACATTTGGATGGCAGTTTGCCTGCTCTTTGTGTTCTCAGCCCTATT

AGAATATGCTGCCGTTAACTTTGTGTCTCGGCAACATAAGGAGCTGCTC

CGATTCAGGAGGAAGCGGAGACATCACAAGAGCCCCATGTTGAATCTAT

TCCAGGAGGATGAAGCTGGAGAAGGCCGCTTTAACTTCTCTGCCTATGG

GATGGGCCCAGCCTGTCTACAGGCCAAGGATGGCATCTCAGTCAAGGGC

GCCAACAACAGTAACACCACCAACCCCCCTCCTGCACCATCTAAGTCCC

CAGAGGAGATGCGAAAACTCTTCATCCAGAGGGCCAAGAAGATCGACAA

AATATCCCGCATTGGCTTCCCCATGGCCTTCCTCATTTTCAACATGTTC

TACTGGATCATCTACAAGATTGTCCGTAGAGAGGACGTCCACAACCAGT

GA

*The codon for the L9'A residue is shown in bold.

Protein Translation

Human GlyRal Wild-Type
(SEQ ID NO: 3)

MYSFNTLRLYLWETIVFFSLAASKEAEAARSAPKPMSPSDFLDKLMGRTSGYDARIRPNFKGPP

VNVSCNIFINSFGSIAETTMDYRVNIFLRQQWNDPRLAYNEYPDDSLDLDPSMLDSIWKPDLFF

ANEKGAHFHEITTDNKLLRISRNGNVLYSIRITLTLACPMDLKNFPMDVQTCIMQLESFGYTMN

DLIFEWQEQGAVQVADGLTLPQFILKEEKDLRYCTKHYNTGKFTCIEARFHLERQMGYYLIQMY

IPSLLIVILSWISFWINMDAA<u>PARVGLGITTVLTMTTQSSGS</u>RASLPKVSYVKAIDIWMAVCLL

FVFSALLEYAAVNFVSRQHKELLRFRRKRRHHKSPMLNLFQEDEAGEGRFNFSAYGMGPACLQA

KDGISVKGANNSNTTNPPPAPSKSPEEMRKLFIQRAKKIDKISRIGFPMAFLIFNMFYWIIYKI

VRREDVHNQ

*The M2 region is underlined and the L'9 residue is shown in bold.

M2 Region of the wild-type human GlyRal
(SEQ ID NO: 4)
```
 P  A R V G L G I T T V L T M T T Q S S G S
-2'      0    2'      6'  9'    13'   16'
```
*The L'9 residue is shown in bold and underline.

Human GlyRal L9'A mutein
(SEQ ID NO: 5)

MYSFNTLRLYLWETIVFFSLAASKEAEAARSAPKPMSPSDFLDKLMGRTSGYDARIRPNFKGPP

VNVSCNIFINSFGSIAETTMDYRVNIFLRQQWNDPRLAYNEYPDDSLDLDPSMLDSIWKPDLFF

ANEKGAHFHEITTDNKLLRISRNGNVLYSIRITLTLACPMDLKNFPMDVQTCIMQLESFGYTMN

DLIFEWQEQGAVQVADGLTLPQFILKEEKDLRYCTKHYNTGKFTCIEARFHLERQMGYYLIQMY

-continued

```
IPSLLIVILSWISFWINMDAAPARVGLGITTVATMTTQSSGSRASLPKVSYVKAIDIWMAVCLL

FVFSALLEYAAVNFVSRQHKELLRFRRKRRHHKSPMLNLFQEDEAGEGRFNFSAYGMGPACLQA

KDGISVKGANNSNTTNPPPAPSKSPEEMRKLFIQRAKKIDKISRIGFPMAFLIFNMFYWIIYKI

VRREDVHNQ
```

*The M2 region is underlined and the L'9A residue is shown in bold.

M2 Region of the L9'A mutant human GlyRa1

(SEQ ID NO: 6)
```
  P  A R V G L I T T V A T M T T Q S S G S
 -2'   0   2'        6'  9'      13'   16'
```
*The L'9A residue is shown in bold and underline.

Certain Definitions

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucl. Acids Res., 19:508; Ohtsuka et al. (1985) JBC, 260:2605; Rossolini et al. (1994) Mol. Cell. Probes, 8:91. A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence or segment," or "polynucleotide" may also be used interchangeably with gene, cDNA, DNA and RNA encoded by a gene.

By "portion" or "fragment," as it relates to a nucleic acid molecule, sequence or segment of the invention, when it is linked to other sequences for expression, is meant a sequence having at least 80 nucleotides, more preferably at least 150 nucleotides, and still more preferably at least 400 nucleotides. If not employed for expressing, a "portion" or "fragment" means at least 9, preferably 12, more preferably 15, even more preferably at least 20, consecutive nucleotides, e.g., probes and primers (oligonucleotides), corresponding to the nucleotide sequence of the nucleic acid molecules of the invention.

The terms "protein," "peptide" and "polypeptide" are used interchangeably herein.

The invention encompasses isolated or substantially purified nucleic acid or protein compositions. In the context of the present invention, an "isolated" or "purified" DNA molecule or an "isolated" or "purified" polypeptide is a DNA molecule or polypeptide that exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein.

"Naturally occurring" or "wildtype" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

"Recombinant DNA molecule" is a combination of DNA sequences that are joined together using recombinant DNA technology and procedures used to join together DNA sequences as described, for example, in Sambrook and Russell, Molecular Cloning: A Laboratory Manual, Cold Spring Harbor, N.Y.: Cold Spring Harbor Laboratory Press ($3^{rd}$ edition, 2001).

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

"Wild-type" refers to the normal gene, or organism found in nature without any known mutation.

"Genome" refers to the complete genetic material of an organism.

A "vector" is defined to include, inter alia, any viral vector, plasmid, cosmid, phage or binary vector in double or single stranded linear or circular form which may or may not be self transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will comprise the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, inducible promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner et al. (1995) Mol. Biotech. 3:225).

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

The "initiation site" is the position surrounding the first nucleotide that is part of the transcribed sequence, which is also defined as position+1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation in a cell of an endogenous gene, transgene, as well as the transcription and stable accumulation of sense (mRNA) or functional RNA. In the case of antisense constructs, expression may refer to the transcription of the antisense DNA only. Expression may also refer to the production of protein.

"Transcription stop fragment" refers to nucleotide sequences that contain one or more regulatory signals, such as polyadenylation signal sequences, capable of terminating transcription. Examples of transcription stop fragments are known to the art.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule.

The terms "trans-acting sequence" and "trans-acting element" refer to DNA or RNA sequences whose function does not require them to be on the same molecule.

The following terms are used to describe the sequence relationships between two or more sequences (e.g., nucleic acids, polynucleotides or polypeptides): (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA, gene sequence or peptide sequence, or the complete cDNA, gene sequence or peptide sequence.

(b) As used herein, "comparison window" makes reference to a contiguous and specified segment of a sequence, wherein the sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) CABIOS, 4:11; the local homology algorithm of Smith et al. (1981) Adv. Appl. Math. 2:482; the homology alignment algorithm of Needleman and Wunsch, (1970) JMB, 48:443; the search-for-similarity-method of Pearson and Lipman, (1988) Proc. Natl. Acad. Sci. USA, 85:2444; the algorithm of Karlin and Altschul, (1990) Proc. Natl. Acad. Sci. USA, 87:2264, modified as in Karlin and Altschul, (1993) Proc. Natl. Acad. Sci. USA, 90:5873.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) Gene 73:237; Higgins et al. (1989) CABIOS 5:151; Corpet et al. (1988) Nucl. Acids Res. 16:10881; Huang et al. (1992) CABIOS 8:155; and Pearson et al. (1994) Meth. Mol. Biol. 24:307. The ALIGN program is based on the algorithm of Myers and Miller, supra. The BLAST programs of Altschul et al. (1990) JMB, 215:403; Nucl. Acids Res., 25:3389 (1990), are based on the algorithm of Karlin and Altschul supra.

Software for performing BLAST analyses is publicly available through the National Center for Biotechnology Information (available on the world wide web at ncbi.nlm-.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the world wide web at ncbi.nlm.nih.gov. Alignment may also be performed manually by visual inspection.

For purposes of the present invention, comparison of sequences for determination of percent sequence identity to another sequence may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of sequences means that a polynucleotide comprises a sequence that has at least 70%, 71%, 72%, 73%, 74%, 75%, 76%, 77%, 78%, or 79%, at least 80%, 81%, 82%, 83%, 84%, 85%, 86%, 87%, 88%, or 89%, at least 90%, 91%, 92%, 93%, or 94%, and at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to the reference sequence over a specified comparison window. Optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point ($T_m$) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl (1984) Anal. Biochem. 138:267; $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), it is preferred to increase the SSC concentration so that a higher temperature can be used. An extensive guide to the hybridization of nucleic acids is found in Tijssen, Laboratory Techniques in Biochemistry and Molecular Biology Hybridization with Nucleic Acid Probes, part I chapter 2 "Overview of principles of hybridization and the strategy of nucleic acid probe assays" Elsevier, New York (1993). Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may results form, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel (1985) Proc. Natl. Acad. Sci. USA 82:488; Kunkel et al. (1987) Meth. Enzymol. 154:367; U.S. Pat. No. 4,873,192; Walker and Gaastra (1983) Techniques in Mol. Biol. (MacMillan Publishing Co., and the references cited therein. Guidance as to appropriate amino acid substitutions that do not affect biological activity of the protein of interest may be found in the model of Dayhoff et al., Atlas of Protein Sequence and Structure (Natl. Biomed. Res. Found. 1978). Conservative substitutions, such as exchanging one amino acid with another having similar properties, are preferred.

Thus, the genes and nucleotide sequences of the invention include both the naturally occurring sequences as well as mutant forms. Likewise, the polypeptides of the invention encompass naturally occurring proteins as well as variations and modified forms thereof. Such variants will continue to possess the desired activity. In certain embodiments, the deletions, insertions, and substitutions of the polypeptide sequence encompassed herein may not produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," "transduced" and "recombinant" refer to a host cell or organism into which a heterologous nucleic acid molecule has been introduced. The nucleic acid molecule can be stably integrated into the genome generally known in the art and are disclosed in Sambrook and Russell, supra. See also Innis et al., PCR Protocols, Academic Press (1995); and Gelfand, PCR Strategies, Academic Press (1995); and Innis and Gelfand, PCR Methods Manual, Academic Press (1999). Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

The term "therapeutically effective amount," in reference to treating a disease state/condition, refers to an amount of vector either alone or as contained in a pharmaceutical composition that is capable of having any detectable, positive effect on any symptom, aspect, or characteristics of a disease state/condition when administered as a single dose or in multiple doses. Such effect need not be absolute to be beneficial.

The terms "treat" and "treatment" refer to both therapeutic treatment and prophylactic or preventative measures, wherein the object is to prevent or decrease an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The methods of the invention may be applied to mammals (e.g., excitable cells of mammals), as well as other chordate phyla (e.g., avians, reptiles, amphibians, bony and cartilaginous fish, etc.), including humans, common laboratory mammals (e.g., mice, rats, guinea pigs, dogs, pigs, monkeys, apes, etc.) and veterinary animals such as cats, dogs, pigs, horses, cattle, sheep, and the like.

EXAMPLES

Certain embodiments of the invention will now be illustrated by the following non-limiting Examples.

Example 1

Purpose

The purpose of the study was to determine whether expression of the hGlyRa1 alone in the absence of β-subunits (monomeric expression) in HEK-293 cells could form a functional channel that was responsive to the natural agonists glycine and/or taurine.

Materials

Plasmid vector pFB-CMV-hGlyRa1-P2A-mEYFP (GenScript) containing the complete coding sequence for fluorescently tagged Human Glycine Receptor subunit alpha 1, and monomeric enhanced yellow fluorescent protein (mEYFP) isoform a was used in this study. The synthetic gene pFB-CMV-hGlyRa1-P2A-mEYFP was assembled from synthetic oligonucleotides and/or PCR products. The fragment was inserted into pcDNA3.1(+). The plasmid DNA was purified from transformed bacteria and concentration determined by UV spectroscopy. The final construct was verified by sequencing.

Gene name: pFB-CMV-hGlyRa1-P2A-mEYFP
Gene size: 1374 bp
Vector backbone: pcDNA3.1(+)
Cloning sites: BamHI/AscI Cells Human embryonic kidney (HEK) 293 cells were purchased from ATCC (#CRL-1573). Cells were cultured in Dulbecco's modified Eagle's medium (DMEM; Gibco #11965) supplemented with 10% FBS (Gibco #26140), 100 units/ml penicillin, 100 µg/ml streptomycin (Gibco #15140), and 1 mM sodium pyruvate (Gibco #11360), and maintained at 37° C. and 5% $CO_2$ in a humidified incubator. Cells were passaged when confluent at a subcultivation ratio of 1:5 or 1:10 every 3 to 4 days.

Description of Methods
Cell Culture

For FlexStation assays, HEK-293 cells were plated at 20,000 cells/well, with a plating volume of 100 µl/well, in a black-sided/clear-bottomed 96-well imaging plate (BD Falcon #353219). For transfection, 16 µl total DNA in 750 µl Opti-MEM (Gibco 31985-070) was mixed with 30 µl ExpressFect in 750 µl Opti-MEM, pre-incubated for 20 minutes, and then added at 15 µl/well to cells containing 100 µl fresh culture media. Cells were transfected 24 hours after plating and assayed 48 hours after transfection. Transfection mixes were removed from cultures following a 4-6 hour incubation period at 37° C./5% $CO_2$ and replaced with fresh glycine-free, culture medium (Gibco 12360-038), supplemented with L-glutamine (Gibco 25030-081).

Membrane Potential Measurements

A fluorescence-based assay employing the FLIPR Membrane Potential Assay Kit, BLUE formulation, (Molecular Devices, #R8042) was used to detect voltage changes across the cell membrane. Dye loading buffer was prepared according to package literature. Specifically, the contents of one vial of BLUE reagent was dissolved with 5 ml of 1×Assay Buffer, followed by a wash of the vial with another 5 ml of 1× Assay Buffer, to yield a total volume of 10 ml of dye loading buffer. Unused portions of dye loading buffer were stored at −20° C. and used within 5 days. For the functional assay, culture medium was removed from the cells and replaced with 50 µl glycine-free MEM. Cells were then loaded with 50 µl of Blue dye loading buffer and incubated for 40 min at 37° C./5% $CO_2$. The signal was detected using the FlexStation 3 multimode benchtop microplate reader operated by SoftMax Pro Data Acquisition & Analysis Software (Molecular Devices). Excitation and emission wavelengths were set at 530 nm and 565 nm, respectively, with an emission cut-off of 550 nm. Plate reads were performed at 30° C. with a 'Low PMT' setting. Run times, of which the first 20 s measured basal fluorescence, were 300 s for glycine-induced signals. Other FlexStation parameters included a pipette height of 130 an initial well volume of 100 µl, a transfer volume of 50 µl (therefore, drug concentrations were prepared 3×), and a transfer rate setting of 2, corresponding to ~31 µl/sec.

A concentration/response curve to glycine and taurine were generated in the hGlyRa1-transfected cells. Glycine and taurine concentrations used were 1, 3, 10, 30, 100, 300, 1000 µM. A dose response curve to glycine was also generated in the presence of 100 µM taurine. Glycine and taurine were dissolved in DMSO as a 10 mM stock and stored as 0.3 mM aliquots at −20° C. Glycine and taurine concentrations for the FlexStation assay were prepared using 1×HBSS with 20 mM HEPES at pH 7.4, containing 0.1% DMSO.

Experimental Treatments

Cells were transfected with the following plasmid: human Glycine Receptor subunit alpha 1, isoform a (hGlyRa1) (pFB-CMV-hGlyRa1-P2A-mEYFP). The following agonists were used to stimulate the GlyR alpha subunit: Glycine (Sigma #G2879) or Taurine (Sigma #T0625).

Description of Calculations or Operations Performed on the Data

Raw FlexStation signals were exported as '.txt' files from SoftMax Pro 5 and analyzed offline using Microsoft Excel 2008 and Origin 7.0.

Statistics

Pooled data are shown as means SEM.

Results

Figure 6:
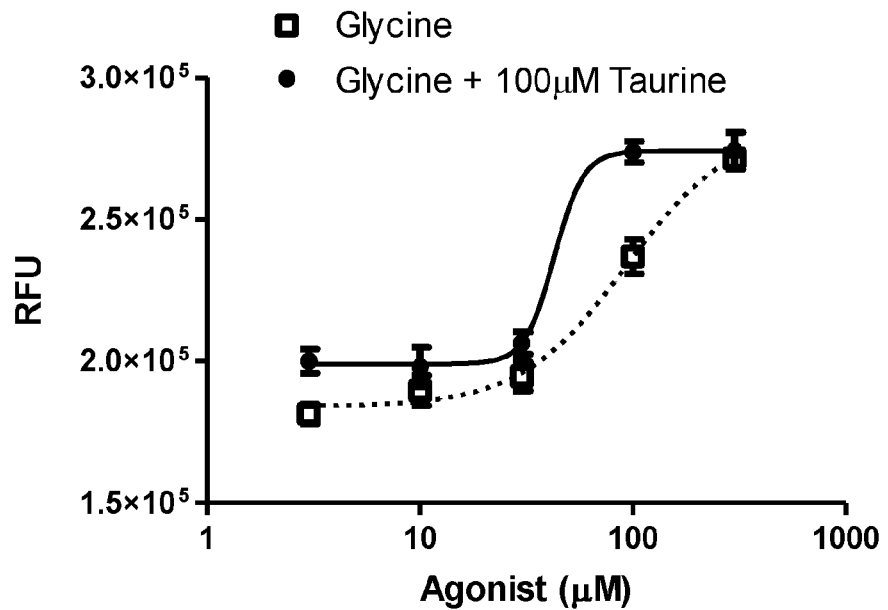
FIG. 6 shows a dose-response curve to glycine on the membrane potential of HEK-293 cells expressing the GlyR α-subunit (hGlyRa1). Data gathered at 4.5 minutes post the addition of Glycine f Taurine show that glycine had a dose-dependent effect on the membrane potential of HEK-293 cells the GlyR α-Subunit (hGlyRa1). Taurine had no effect on the membrane potential of these cells. Fitted curves show that the response to Glycine had an $EC_{50}$ concentration of 92 µM which was not significantly affected by the presence of 100 µM Taurine ($EC_{50}$=43 µM).
Figure 7:
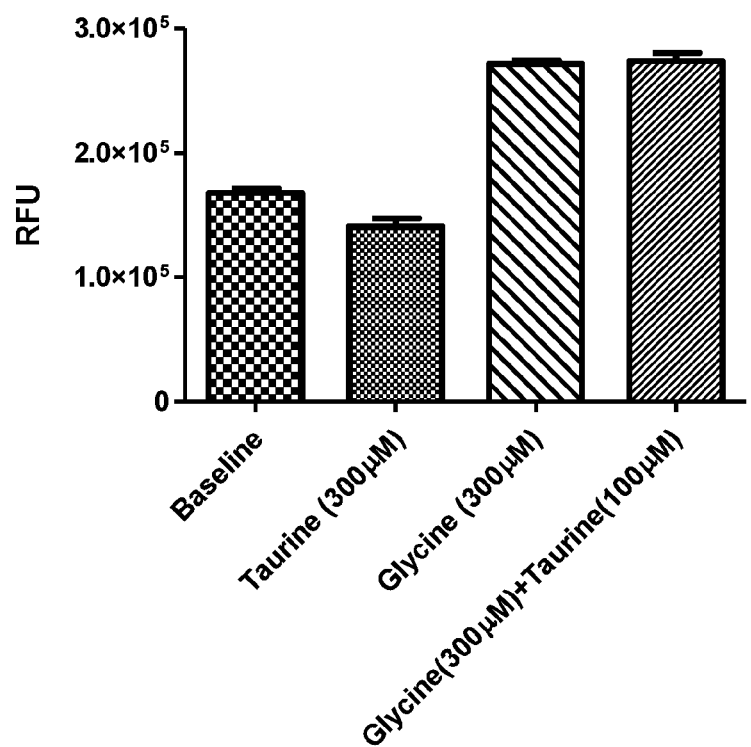
FIG. 7 shows the effect of glycine±taurine on membrane potential of HEK-293 expressing the GlyR α-subunit (hGlyRa1). In HEK-293 cells expressing the GlyR α-Subunit (hGlyRa1), the baseline membrane potential (see, the first 20 seconds prior to the addition of glycine in FIGS. 5A-5B) (Baseline) was not significantly altered by the addition of Taurine (300 µM) but was altered by the addition of Glycine (300 µM) when measured at 4.5 min post-treatment. The 4.5 min post-treatment response to Glycine (300 µM) was not affected by the presence of Taurine (100 µM).

In cells expressing the GlyR α-subunit (hGlyRa1) there was no unstimulated change in membrane potential (FIGS. 5A-5B, FIG. 7), nor did they respond with any change in membrane potential to increasing concentrations of taurine (1 µM to 1 mM) (FIG. 6, FIG. 7). In these cells, the addition of increasing concentrations of glycine (1 µM to 1 mM) resulted in a dose-dependent change in membrane potential (FIGS. 5A-5B) with an $EC_{50}$ of 92 µM and an $EC_{100}$ of approximately 300 µM (FIG. 6). The response to glycine was not significantly affected ($EC_{50}$=43 µM) by the presence of taurine (100 µM). These data are in good agreement with those previously reported by Sontheimer H. et al. ((1989) Neuron 2(5): 1491-1497) ($EC_{50}$=100 µM) and Jensen A A.

and Kristiansen U. ((2004) Biochemical Pharmacology 67(9): 1789-1799) ($EC_{50}$=82 µM) using a similar assay.

These data also show that these monomeric channels can be activated by normal endogenous levels of glycine present in human plasma (242-258 µM) (Geigy Scientific Tables, 8th Rev edition, pp. 93. Edited by C. Lentner, West Cadwell N.J.: Medical Education Div., Ciba-Geigy Corp. Basel, Switzerland c1981-1992).

When expressed in neuronal cells, these changes in membrane potential measured in HEK-293 cells are anticipated to result in a hyperpolarization due to influx of ions via the $Cl^-$-selective channel formed by the monomeric expression of the GlyR α-subunit and subsequent exposure of the receptor to the endogenous agonist glycine. Taurine has been reported to be a partial agonist of the αβ-multimeric GlyR but had no direct effect, or affected the glycine response, on the monomeric channel in these studies. Taurine is present in human plasma at a concentration of 141-162 µM (Geigy Scientific Tables, 8th Rev edition, pp. 93. Edited by C. Lentner, West Cadwell, N.J.: Medical Education Div., Ciba-Geigy Corp. Basel, Switzerland c1981-1992).

Conclusions

Monomeric expression of the glycine receptor α-subunit (hGlyRa1) in HEK-293 cells forms a functional chloride channel that is responsive to glycine at concentrations present in normal human plasma.

Example 2

Purpose

To measure the glycine levels present in normal male rat plasma and ascertain that the rat was a suitable species in which to assess the analgesic efficacy of GlyRa1 when delivered via a viral vector to nociceptive neurons and subsequently activated by endogenous glycine.

Methods

Blood was collected from 6 adult male Sprague Dawley rats onto K2EDTA. The samples were centrifuged and the plasma separated and frozen for storage and transportation.

Once thawed and the plasma proteins precipitated, the concentrations of glycine in rat plasma samples were measured with LC/MS/MS system (AB Sciex API-4000Qtrap mass spectrometer and Shimazu 20A HPLC with a Thermo Silica 100×2.1 mm HPLC column). Positive ESI ionization with MRM scans (m/z, 76/48) were used. The calibration range of this method was 10 to 5000 ng/mL.

Results

The plasma glycine levels in male rat plasma ranged from 13.8 to 23.0 µg/mL (184-307 µM) with an average of 240.9±45.2 µM (mean±SD).

Conclusions

The levels of glycine present in rat plasma is similar to the 242.0±44.0 µM reported in normal adult human male and 258.0±64.0 µM in normal adult human female (Geigy Scientific Tables, 8th Rev edition, pp. 93. Edited by C. Lentner, West Cadwell, N.J.: Medical Education Div., Ciba-Geigy Corp. Basel, Switzerland c1981-1992). The glycine levels in rat plasma are within a suitable range to activate monomeric GlyRa1 channels that have an $EC_{50}$ of 92 µM and an $EC_{100}$ of approximately 300 µM (FIG. 6) when expressed in peripheral tissues.

Based on the similarity of glycine levels in rat and human plasma the rat is a suitable species in which to assess the analgesic efficacy of GlyRa1 when delivered via a viral vector to nociceptive neurons and subsequently activated by endogenous glycine.

Example 3

Purpose

To assess the effectiveness of GTX-01 to attenuate the heperalgesia/allodynia response in a rat model of chronic neuropathic pain.

Materials

Viral Vector

Treatments comprised of a gene therapy DNA sequence, delivered using an AAV. The gene therapy comprised of the following components:

Adeno-associated virus (serotype 6)—AAV6

Human synapsin promoter—hSyn

DNA encoding the alpha-1-subunit of the GlyR receptor—GlyRa1

Green fluorescent protein—GFP

The vectors were designed, cloned and synthesized by Goleini, Inc. and packaged into AAV6 by Virovec, Inc. (Hayward, Calif.) using a BAC-to-AAV technology that utilizes the baculovirus expression system to produce AAV vectors in insect cells under serum-free condition.

Active treatment: (GTX-01) AAV6-hSyn-GlyRa1. The virus was supplied and administered as an aqueous solution containing 9.41e13 viral particles/mL.

Control treatment: (CONTROL) AAV6-hSyn-GFP. The virus was supplied and administered as an aqueous solution containing 2.22e13 viral particles/mL Animals Nine male Sprague-Dawley rats (Envigo, Hayward, Calif.) weighing between 182 g and 227 g underwent surgery as described below to establish the SNI model of neuropathic pain. All animals were individually identified by tail markings which were re-marked at regular intervals. Throughout the study animals were allowed access to food and water ad libitum.

Methods

Spared Nerve Injury (SNI) Model—Surgery

Under isoflurane anesthesia the skin on the lateral surface of the thigh was incised and a section made directly through the biceps femoris muscle exposing the sciatic nerve and its three terminal branches: the sural, common peroneal and tibial nerves. The SNI procedure comprised an axotomy and ligation of the tibial and common peroneal nerves leaving the sural nerve intact. The common peroneal and the tibial nerves were tight-ligated with 5.0 silk and sectioned distal to the ligation, removing 2±4 mm of the distal nerve stump. Great care was taken to avoid any contact with or stretching of the intact sural nerve. Muscle and skin were closed in two layers (Decosterd I. and Woolf C. (2000) Pain 87(2):149-158). In the current study this was considered as Day 0.

Testing for Mechanical Hypersensitivity

Testing was performed during the day portion of the circadian cycle only (06:00-18:00 h). Rats were placed in an inverted plastic cage on an elevated wire mesh platform which allowed full access to the paws. Behavioral accommodation was allowed for approximately 15 min, until cage exploration and major grooming activities ceased. The area tested was the lateral region of the plantar left hind paw, in the sural nerve distribution, avoiding the less sensitive tori (footpads). The paw was touched with 1 of a series of 8 von Frey filaments with logarithmically incremental stiffness (0.41, 0.70, 1.20, 2.00, 3.63, 5.50, 8.50, and 15.10 g) (Stoelting). The von Frey filament was presented perpendicular to the plantar surface with sufficient force to cause slight buckling against the paw, and held for approximately 6-8 s. Stimuli were presented at intervals of several seconds, allowing for apparent resolution of any behavioral responses to previous stimuli. A positive response was noted if the paw was sharply withdrawn. Flinching immediately upon removal of the hair was also considered a positive response. Ambulation was considered an ambiguous response, and in such cases the stimulus was repeated. Based on observations on normal, un-operated rats, the cut-off of a 15.10 g filament (~10% of the body weight of the smaller rats) was selected as the upper limit for testing, since stiffer filaments tended to raise the entire limb rather than to buckle, substantially changing the nature of the stimulus (Chaplan S. et al. (1994) J Neurosci Methods 53(1): 55-63).

One day prior to the surgery (Day −1) animals were tested for their baseline response to mechanical stimulation (mechanical sensitivity). At 10 days post-surgery all animals were re-tested for their mechanical sensitivity.

On day 10 post-surgery animals were treatment with either Control vector or GTX-01. Under general anesthesia (isoflurane) either GTX-01 or Control vector were administered at a dose of 1.88e12 and 4.44e11 vector genomes, respectively, in a volume of 20 µL (2×10 µL injections) injected sub-cutaneous into the lateral area of the left hind paw pad.

On days 14, 21, 29, 36, 44 and 51 post-treatment (days 24, 31, 39, 46, 54 and 61 post-surgery) animals were re-evaluated for their mechanical sensitivity. For all of these measurements the operator was blinded as to the identity of the animals.

Experimental Treatments (2)

Groups of animals were dosed with one of the following treatments:
- GTX-01: 4 animals received 2×10 µL/paw of an AAV6 virus preparation at an estimated concentration 9.41e13 viral particles/mL. The virus carried DNA that encoded for pFB-hSyn-GlyRa1
- CONTROL: 5 animals received 2×10 µL/paw of an AAV6 virus preparation at an estimated concentration 2.22e13 viral particles/mL. The virus carried DNA that encoded for hSyn-GFP.

Description of Calculations or Operations Performed on the Data

The 50% withdrawal threshold was determined using the up-down method of Dixon (Dixon, WJ. (1980) Ann. Rev. Pharmacol. Toxicol. 20:441-462; Chaplan S. et al. (1994) J Neurosci Methods 53(1):55-63). In this paradigm, testing was initiated with the 2.0 g filament, in the middle of the series. Stimuli were always presented in a consecutive fashion, whether ascending or descending. In the absence of a paw withdrawal response to the initially selected filament, a stronger stimulus was presented; in the event of paw withdrawal, the next weaker stimulus was chosen. According to Dixon, optimal threshold calculation by this method requires 6 responses in the immediate vicinity of the 50% threshold. Since the threshold is not known, strings of similar responses may be generated as the threshold is approached from either direction. Accordingly, although all responses were noted, counting of the critical 6 data points did not begin until the response threshold was first crossed, at which time the 2 responses straddling the threshold were retrospectively designated as the first 2 responses of the series of 6. Four additional responses to the continued presentation of stimuli that were varied sequentially up or down, based on the rat's response, constituted the remainder of the series. Thus, the number of actual responses collected using this paradigm can vary from a minimum of 4 (in the case of paw withdrawal sequentially to the 4 filament in the descending range 2.0-0.4 g: threshold lies below the range of actual stimuli) to a maximum of 9 (in the case of the first withdrawal occurring on the fifth ascending stimulus presentation at 15.1 g, followed by elicitation of 4 additional responses, assuming that withdrawals continue to occur at or below 15.1 g). In cases where continuous positive or negative responses were observed to the exhaustion of the stimulus set, values of 15.00 g and 0.25 g were assigned respectively. The resulting pattern of positive and negative responses was tabulated using the convention, X=withdrawal; 0=no withdrawal, and the 50% response threshold was interpolated using an algorithm based on Chaplan's version of Dixon's up-down method (Chaplan S. et al. (1994) J Neurosci Methods 53(1):55-63; Dixon W J. (1980) Ann. Rev. Pharmacol. Toxicol. 20:441-462).

The difference in the response to mechanical stimulation between control and GTX-01-treated groups at days 14, 21, 29, 36, 44 and 51 post-treatment was analyzed for statistical significance using an unpaired Student's t-test.

Results

Figure 8:
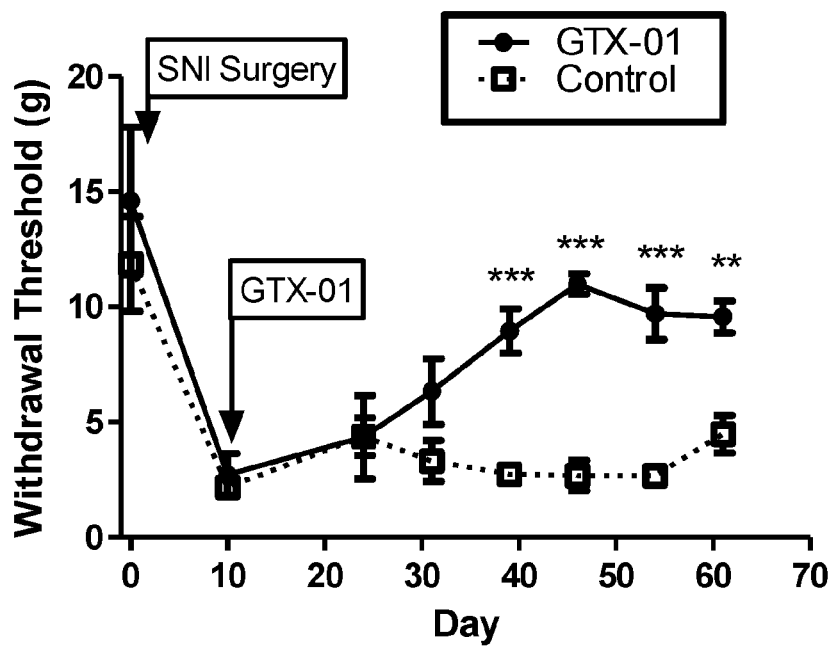
FIG. 8 shows a time-course of the analgesic effects of GTX-01 in the SNI model of neuropathic pain in the rat. Baseline evaluations were measured at Day −1 and surgery to sever the peroneal and tibial nerves was done on Day 0. All rats are hypersensitive to mechanical stimulation (allodynia) at day 10 post-surgery. GTX-01 or a control vector was administered on Day 10. A time-dependent reversal of allodynia consistent with viral delivery of gene therapy in peripheral nerves was observed. Data points represent the mean of 4 animals "GTX-01" and 5 animals "Control"±SEM.  $P<0.01$, * $P<0.001$.

The GTX-01 group showed significant analgesia as measured by increased withdrawal thresholds at day 29 ($P<0.001$), day 36 ($P<0.001$), day 44 ($P<0.001$) and day 51 ($P<0.01$) post-treatment. The data for both groups, Controls (n=5) and GTX-01 (n=4) is shown in Table 4 and FIG. 8.

TABLE 4

| Day (post-treatment) | Control | GTX-01 |
|---|---|---|
| 0 (−10) | 11.9 ± 4.6 | 14.6 ± 6.4 |
| 10 (0) | 2.2 ± 0.8 | 2.7 ± 1.8 |
| 24 (14) | 2.2 ± 1.8 | 4.4 ± 3.6 |
| 31 (21) | 4.4 ± 2.0 | 6.3 ± 2.8 |
| 39 (29) | 3.3 ± 0.5 | 9.0 ± 1.9*** |
| 46 (36) | 2.7 ± 1.5 | 11.0 ± 0.9*** |
| 54 (44) | 2.7 ± 0.8 | 9.7 ± 2.2*** |
| 61 (51) | 2.7 ± 1.8 | 9.6 ± 1.4** |

Table 4. Mechanical threshold (g) of rats that underwent an axotomy and ligation of the tibial and common peroneal nerves leaving the sural nerve intact (spared nerve injury) at day 0 and treated with either a control virus (Control) or GTX-01 on day 10. Mechanical threshold (g) data are presented as mean ± standard deviation (SD) of 5 animals (Control) and 4 animals GTX-01. Control and GTX-01 groups were analyzed for statistical significance using an unpaired Student's t-Test. Significant differences are denoted by P < 0.01 or *P < 0.001.

Taking the baseline data on day −1 to represent normal or 100% analgesia and that on day 10 is given to represent 0% analgesia then the average analgesic effect of GTX-01 at days 29, 36, 44 and 51 post-administration of GTX-01 was 52%, 70%, 59% and 58%, respectively.

Figure 9:
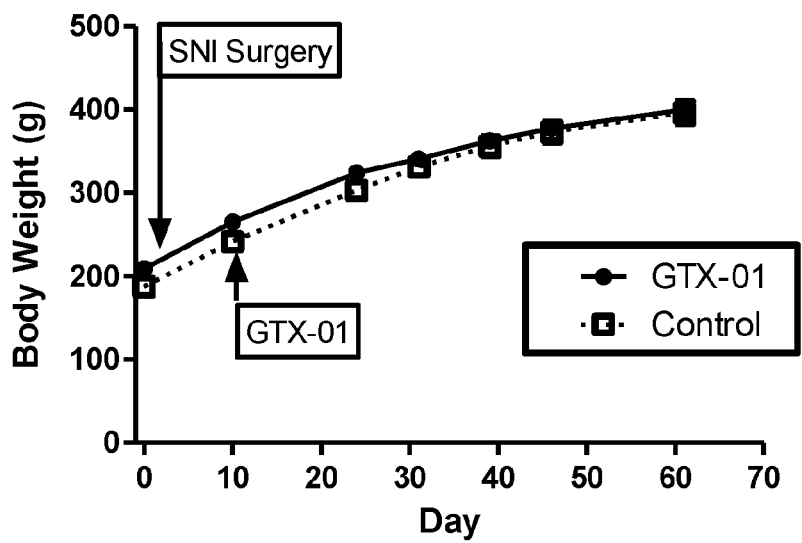
FIG. 9 shows the body weight of SNI rats treated with either GTX-01 or Control vector. Body weights were measured and recorded throughout the study. No differences were seen in the body weights of animals treated with GTX-01 vs. Control vector.

Body weights were measured and recorded throughout the study. No differences were seen in the body weights of animals treated with GTX-01 vs. Control vector (FIG. 9).

Conclusions

A single administration of GTX-01 without the administration of any other agent produced a significant and long-lasting analgesic effect in the SNI model of chronic neuropathic pain in the rat. This is differentiated from, and is in contrast to the data reported by Goss J R. et al. (2010) Molecular Therapy 19(3): 500-506 and U.S. Pat. No. 8,957, 036 where they describe analgesia following the viral delivery of GlyRa1 and its subsequent expression only when the receptor agonist (glycine) is administered to the animal either in the form of an injection into the site of pain such as "plantar surface of the formalin injected foot" or systemically via the jugular vein to treat a model of interstitial cystitis.

Example 4

Purpose

The purpose of the study was to determine whether expression of the L9'A mutated GluCl α-subunit alone in the absence of β-subunits (monomeric expression) in HEK-293 cells could form a constitutively active chloride channel (designated GluCl*).

Materials

Plasmid vector GluCLoptbetmFYPY182F (Life Technologies) containing the complete optimized coding sequence for fluorescently tagged *Caenorhabditis elegans* GluCl α-subunit, was used in this study. Enhanced yellow fluorescent protein (YFP) insertions are located within the intracellular M3-M4 loop. The synthetic gene GluCLoptbetmFYPY182F was assembled from synthetic oligonucleotides and/or PCR products. The fragment was inserted into pcDNA3.1(+). The plasmid DNA was purified from transformed bacteria and concentration determined by UV spectroscopy. The final construct was verified by sequencing.

Designation: *E. coli* K12 (dam+dcm+tonA rec-)Gene name: GluCLoptbetmFYPY182F

Gene size: 2043 bp

Vector backbone: pcDNA3.1(+)

Cloning sites: HindIII/XhoI

Site-Directed Mutagenesis

Leucine 9" mutations were made using the QuikChange II XL site-directed mutagenesis kit (Agilent Technologies #200522) with PfuTurbo DNA polymerase (Agilent Technologies #600250) using the following forward and reverse primers: 5'-CC CTG GGC GTG ACC ACC CTG xxx AC-3' (SEQ. ID NO: 7) and 5'-GC GGA CTG AGC GGT CAT GGT xxx CA-3'(SEQ. ID NO: 8), where 'xxx' delineates the mutated Leu9' codon. For GluCl*, Leu9' was mutated to Ala. All mutations were confirmed by DNA sequencing.

Cells

Human embryonic kidney (HEK) 293 cells were purchased from ATCC (#CRL-1573). Cells were cultured in Dulbecco's modified Eagle's medium (DMEM; Gibco #11965) supplemented with 10% FBS (Gibco #26140), 100 units/ml penicillin, 100 μg/ml streptomycin (Gibco #15140), and 1 mM sodium pyruvate (Gibco #11360), and maintained at 37° C. and 5% $CO_2$ in a humidified incubator. Cells were passaged when confluent at a subcultivation ratio of 1:5 or 1:10 every 3 to 4 days.

Description of Methods

Cell Culture

For FlexStation assays, HEK-293 cells were plated at 20,000 cells/well, with a plating volume of 100 μl/well, in a black-sided/clear-bottomed 96-well imaging plate (BD Falcon #353219). For transfection, 16 μg total DNA in 750 μl DMEM was mixed with 30 μl ExpressFect in 750 μl DMEM, pre-incubated for 20 minutes, and then added at 15 μl/well to cells containing 100 μl fresh culture media. Cells were transfected 24 hours after plating and assayed 48 hours after transfection. Transfection mixes were removed from cultures following a 4-6 hour incubation period at 37° C./5% $CO_2$ and replaced with fresh culture medium.

Membrane Potential Measurements

A fluorescence-based assay employing the FLIPR Membrane Potential Assay Kit, BLUE formulation, (Molecular Devices, #R8042) was used to detect voltage changes across the cell membrane. Dye loading buffer was prepared according to package literature. Specifically, the contents of one vial of BLUE reagent was dissolved with 5 ml of 1× Assay Buffer, followed by a wash of the vial with another 5 ml of 1× Assay Buffer, to yield a total volume of 10 ml of dye loading buffer. Unused portions of dye loading buffer were stored at −20° C. and used within 5 days. For the functional assay, culture medium was removed from the cells and replaced with 50 DMEM. Cells were then loaded with 50 μl of Blue dye loading buffer and incubated for 40 min at 37° C./5% $CO_2$. The signal was detected using the FlexStation 3 multimode benchtop microplate reader operated by SoftMax Pro Data Acquisition & Analysis Software (Molecular Devices). Excitation and emission wavelengths were set at 530 nm and 565 nm, respectively, with an emission cut-off of 550 nm. Plate reads were performed at 30° C. with a 'Low PMT' setting. Run times, of which the first 20 s measured basal fluorescence, were 300 s for ivermectin-induced signals. Other FlexStation parameters included a pipette height of 230 μl, an initial well volume of 100 μl, a transfer volume of 50 μl (therefore, drug concentrations were prepared 3×), and a transfer rate setting of 2, corresponding to ~31 μl/sec.

A concentration/response curve to ivermectin was generated in both the GluCl* and wild type-transfected cells. Ivermectin concentrations used were 1, 3, 10, 30, 100, 300, 1000 nM. Ivermectin was dissolved in DMSO as a 10 mM stock and stored as 0.3 mM aliquots at −20° C. Ivermectin concentrations for the FlexStation assay were prepared using 1×HBSS with 20 mM HEPES at pH 7.4, containing 0.1% DMSO.

Experimental Treatments

Cells were transfected with one of the following plasmids:
pFB-CMV-GluCloptalpha-mEYFP-L9'L (Wild type) (GluCLoptbetmFYPY182F)
pFB-CMV-GluCloptalpha-mEYFP-L9'A (GluCl*)

The following agonists were used to stimulate the transfected cells

Ivermectin (Sigma #18898)

Description of Calculations or Operations Performed on the Data

Raw FlexStation signals were exported as '.txt' files from SoftMax Pro 5 and analyzed offline using Microsoft Excel 2008 and Origin 7.0.

Statistics

Pooled data are shown as means±SEM.

Results

Figure 10:
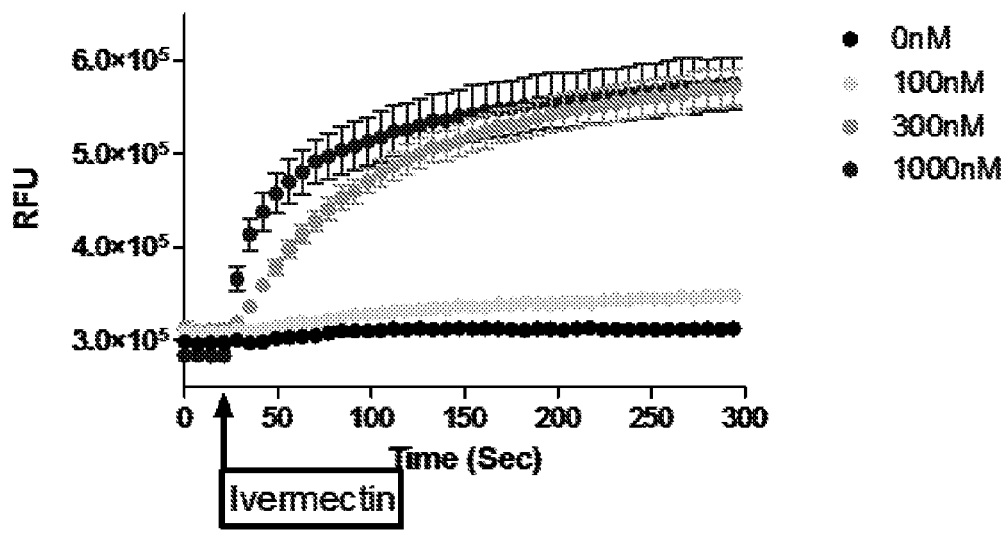
FIG. 10 shows that ivermectin exhibits a dose-dependent effect on the membrane potential of HEK-293 cells expressing the wild-type α-subunit of the GluCl glutamate receptor alone. This demonstrates that a monomeric chloride-selective channel can be formed by the α-subunit of the GluCl glutamate receptor.
Figure 11:
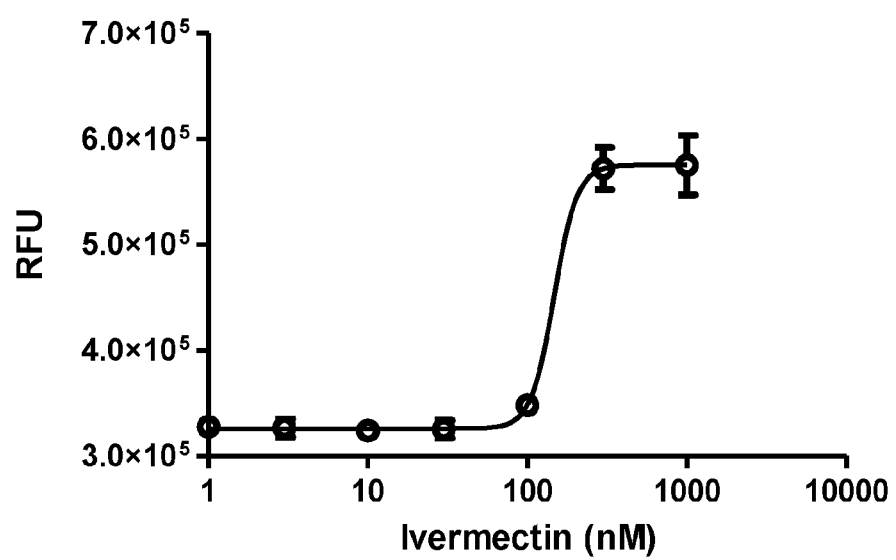
FIG. 11 illustrates that data gathered at 4.5 minutes post the addition of ivermectin (as shown in FIG. 10) showed that ivermectin had a dose-dependent effect on the membrane potential of HEK-293 cells expressing the monomeric wild-type α-subunit of the GluCl glutamate receptor. Fitting a curve to the data shows that the response to Ivermectin had an $EC_{50}$ concentration of 147 nM.

In cells expressing the wild-type GluCl α-subunit there was no unstimulated change in membrane potential (FIG. 10). The addition of increasing concentrations of ivermectin resulted in a dose-dependent change in membrane potential (FIG. 10) with an $EC_{50}$ of 147 nM (FIG. 11).

Figure 12:
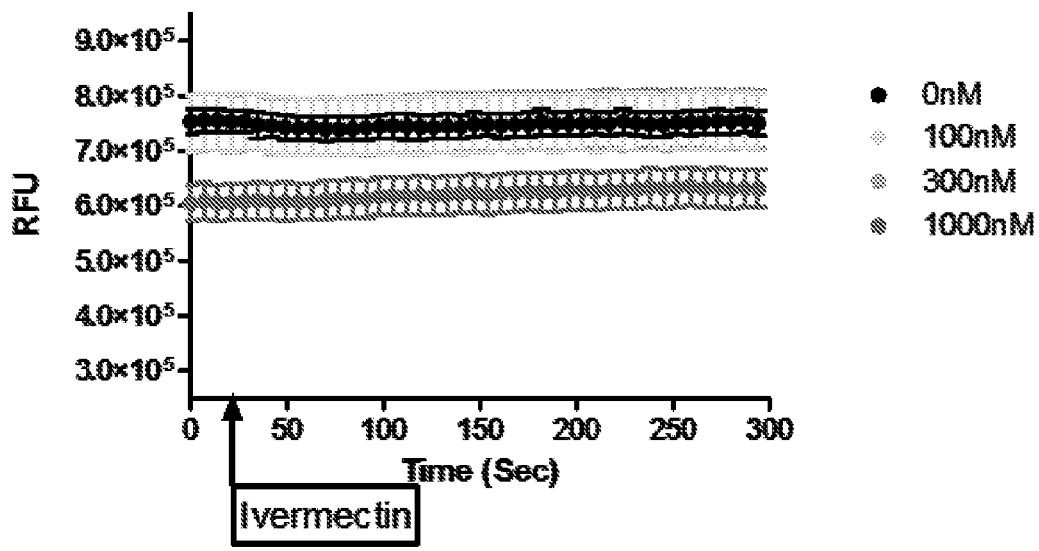
FIG. 12 shows that in HEK-293 cells expressing the L9'A mutation of the of the GluCl glutamate receptor α-subunit alone the baseline membrane potential (first 20 seconds prior to the addition of ivermectin) was maximally changed and was equal to that seen in cells expressing wild-type α-subunit of the GluCl glutamate receptor when stimulated by a maximally effective concentration of ivermectin. In cells expressing the L9'A mutation of the GluCl glutamate receptor α-subunit, ivermectin did not augment the change in membrane potential beyond that measured at baseline.

In cells expressing the L9'A mutated GluCl α-subunit (GluCl*) the baseline membrane potential was maximally altered (FIG. 12). The response was similar in magnitude to that seen in the wild-type GluCl α-subunit in response to 1 μM ivermectin (FIG. 10). Addition of increasing doses of ivermectin to the cells expressing GluCl* did not augment the change in membrane potential (FIG. 12).

When expressed in neuronal cells, these changes in membrane potential measured in HEK-293 cells are anticipated to result in a hyperpolarization due to influx of Cl− ions via the Cl−-selective channel formed by the monomeric expression of the GluCl α-subunit and subsequent application of the receptor agonist ivermectin. The monomeric expression of the L9'A mutation of the GluCl α-subunit in neuronal cells is expected to form a constitutively active CF which is anticipated to result in a permanent hyperpolarization of neuronal tissue without the addition of an agonist.

Conclusions

Monomeric expression of the L9'A mutation of the *Caenorhabditis elegans* GluCl glutamate receptor α-subunit in HEK-293 cells forms a functional and constitutively active chloride channel.

Example 5

Purpose

The purpose of this study was to assess the effectiveness of GTX-01* to attenuate the heperalgesia/allodynia response in a rat model of chronic neuropathic pain.

Materials

Treatments comprised of a gene therapy DNA sequence, delivered using an AAV. The gene therapy comprised of the following components:

Adeno-associated virus (serotype 6)—AAV6
Human synapsin promoter—hSyn
DNA encoding GluCl*—the alpha-subunit of the GluCl receptor with an L9'A mutation to generate a constitutively open channel. pFB-hSyn-GluCloptalpha-mEYFP-L9'A
Enhanced yellow fluorescent protein—EYFP The vectors were designed, cloned and synthesized by Goleini, Inc. and packaged into AAV6 by Virovec, Inc. (Hayward, Calif.) using a proprietary BAC-to-AAV technology that utilizes the baculovirus expression system to produce AAV vectors in insect cells under serum-free condition.

Active Treatment: GTX-01*

AAV6-hSyn-GluCloptalpha-mEYFP-L9'A. The virus was supplied and administered as an aqueous solution containing 9.79e13 viral particles/mL.

Control Treatment: CONTROL

AAV6-hSyn-EYFP The virus was supplied and administered as an aqueous solution containing 2.22e13 viral particles/mL.

At the end of the study the animals received Gabapentin (100 mg/kg: IP) (Sigma Aldrich, G154).

Animals

Two groups of 6 male Sprague-Dawley rats (Envigo, Hayward, Calif.) weighing between 200 and 250 g (6-7 weeks of age) were selected from an initial population of 21 animals that underwent surgery as described below to establish the SNI model of neuropathic pain. Animals were selected based on their mechanical sensitivity at 10 days post-surgery. The 12 animals selected had similar hypersensitivity to mechanical stimulation. The 12 selected animals were ranked according to their mechanical sensitivity and allocated alternatively to "treatment" and "control" groups to create 2 "balanced" groups of animals with similar hypersensitivity to mechanical stimulation. All animals were individually identified by rail markings which were re-marked at regular intervals. Throughout the study animals were allowed access to food and water ad libitum.

Methodology

Studies were conducted in accordance with protocols approved by AfaSci's Institutional Animal Care and Use Committee (IACUC).

Description of Methods

Spared Nerve Injury (SNI) Model—Surgery:

Under isoflurane anesthesia the skin on the lateral surface of the thigh was incised and a section made directly through the biceps femoris muscle exposing the sciatic nerve and its three terminal branches: the sural, common peroneal and tibial nerves. The SNI procedure comprised an axotomy and ligation of the tibial and common peroneal nerves leaving the sural nerve intact. The common peroneal and the tibial nerves were tight-ligated with 5.0 silk and sectioned distal to the ligation, removing 2±4 mm of the distal nerve stump. Great care was taken to avoid any contact with or stretching of the intact sural nerve. Muscle and skin were closed in two layers (Decosterd I. and Woolf C. (2000) Pain 87(2):149-158). In the current study this was considered as Day 0.

Testing for Mechanical Hypersensitivity:

Testing was performed during the day portion of the circadian cycle only (06:00-18:00 h). Rats were placed in an inverted plastic cage on an elevated wire mesh platform which allowed full access to the paws. Behavioral accommodation was allowed for approximately 15 min, until cage exploration and major grooming activities ceased. The area tested was the lateral region of the plantar left hind paw, in the sural nerve distribution, avoiding the less sensitive tori (footpads). The paw was touched with 1 of a series of 8 von Frey filaments with logarithmically incremental stiffness (0.41, 0.70, 1.20, 2.00, 3.63, 5.50, 8.50, and 15.10 g) (Stoelting). The von Frey filament was presented perpendicular to the plantar surface with sufficient force to cause slight buckling against the paw, and held for approximately 6-8 s. Stimuli were presented at intervals of several seconds, allowing for apparent resolution of any behavioral responses to previous stimuli. A positive response was noted if the paw was sharply withdrawn. Flinching immediately upon removal of the hair was also considered a positive response. Ambulation was considered an ambiguous response, and in such cases the stimulus was repeated. Based on observations on normal, un-operated rats, the cut-off of a 15.10 g filament (~10% of the body weight of the smaller rats) was selected as the upper limit for testing, since stiffer filaments tended to raise the entire limb rather than to buckle, substantially changing the nature of the stimulus (Chaplan S. et al. (1994) J Neurosci Methods 53(1): 55-63).

One day prior to the surgery (Day −1) animals were tested for their baseline response to mechanical stimulation (mechanical sensitivity). At 10 days post-surgery all animals were re-tested for their mechanical sensitivity.

On day 10 post-surgery the twelve animals with the greatest mechanical hypersensitivity were selected for treatment with either Control vector or GTX-01*. Under general anesthesia (isoflurane) either GTX-01* or Control vector were administered at a dose of 1.96e12 and 4.44e11 vector genomes, respectively, in a volume of 20 μL (2×10 μL injections) injected sub-cutaneous into the lateral area of the left hind paw pad.

At days 13, 22 and 35 post-treatment (days 23, 32 and 45 post-surgery) animals were re-evaluated for their mechanical sensitivity. For all of these measurements the operator was blinded as to the identity of the animals.

At day 22 post-treatment (day 32 post-surgery) one animal from each of the control and GTX-01*-treated groups were euthanized and tissues harvested and processed as described below.

At day 36 post-treatment (day 46 post-surgery) the animals were dosed with gabapentin (100 mg/kg: IP). At 1 hour and 2 hours post-gabapentin administration the animals were evaluated for their sensitivity to mechanical stimulation.

Tissue Harvest:

On day 22 post-treatment and at the end of the experiment on day 36 post-treatment animals were euthanized by the administration of isoflurane followed by a thoracotomy. The left side dorsal root ganglia (L4, L5 and L6), the left sural nerve and the left hind paws were harvested and fixed in 4% paraformaldehyde at 4° C. for 14 days, and then transferred to 20% sucrose for at least 24 hours. The tissues were subsequently cryo-sectioned and stained for histologic evaluation using confocal microscopy. Primary antibodies against the YFP were used to identify expression of the pFB-hSyn-GluCloptalpha-mEYFP-L9'A gene.

Experimental Treatments

Groups of animals were dosed with one of the following treatments:

GTX01*—6 animals received 2×10 4/paw of an AAV virus preparation at an estimated concentration 9.79e13 viral particles/mL. The virus carried DNA that encoded for pFB-hSyn-GluCloptalpha-mEYFP-L9'A CONTROL—6 animals received 2×10 µL/paw of an AAV6 virus preparation at an estimated concentration 2.22e13 viral particles/mL. The virus carried DNA that encoded for hSyn-EYFP Exclusion Parameters:

No animals were excluded from the study. No animals died during the study.

Description of Calculations or Operations Performed on the Data

The 50% withdrawal threshold was determined using the up-down method of Dixon (Chaplan S. et al. (1994) J Neurosci Methods 53(1):55-63; Dixon W J. (1980) Ann. Rev. Pharmacol. Toxicol. 20:441-462). In this paradigm, testing was initiated with the 2.0 g filament, in the middle of the series. Stimuli were always presented in a consecutive fashion, whether ascending or descending. In the absence of a paw withdrawal response to the initially selected filament, a stronger stimulus was presented; in the event of paw withdrawal, the next weaker stimulus was chosen. According to Dixon, optimal threshold calculation by this method requires 6 responses in the immediate vicinity of the 50% threshold. Since the threshold is not known, strings of similar responses may be generated as the threshold is approached from either direction. Accordingly, although all responses were noted, counting of the critical 6 data points did not begin until the response threshold was first crossed, at which time the 2 responses straddling the threshold were retrospectively designated as the first 2 responses of the series of 6. Four additional responses to the continued presentation of stimuli that were varied sequentially up or down, based on the rat's response, constituted the remainder of the series. Thus, the number of actual responses collected using this paradigm can vary from a minimum of 4 (in the case of paw withdrawal sequentially to the 4 filament in the descending range 2.0-0.4 g: threshold lies below the range of actual stimuli) to a maximum of 9 (in the case of the first withdrawal occurring on the fifth ascending stimulus presentation at 15.1 g, followed by elicitation of 4 additional responses, assuming that withdrawals continue to occur at or below 15.1 g). In cases where continuous positive or negative responses were observed to the exhaustion of the stimulus set, values of 15.00 g and 0.25 g were assigned respectively. The resulting pattern of positive and negative responses was tabulated using the convention, X=withdrawal; 0=no withdrawal, and the 50% response threshold was interpolated using an algorithm based on Chaplan's version of Dixon's up-down method (Chaplan S. et al. (1994) J Neurosci Methods 53(1):55-63; Dixon W J. (1980) Ann. Rev. Pharmacol. Toxicol. 20:441-462).

The difference in the response to mechanical stimulation between control and GTX-01*-treated groups at days 13, 22 and 35 post-treatment was analyzed for statistical significance using an unpaired Student's t-test. The response to gabapentin was analyzed for statistical significance by comparing the 1 hour and 2 hour post-gabapentin dosing with the pre-treatment values using an unpaired Student's t-test.

Results

At day −1 the baseline withdrawal threshold for the animals selected for the study had an average value of 6.24±0.09 g (Control group) and 6.27±0.09 g (GTX-01* group). At day 10 post-surgery the withdrawal threshold in the animals chosen for control vector and GTX-01* treatment was 1.40±0.18 g and 1.51±0.14 g, respectively. At day 13 post-administration of either the control vector or GTX-01* the withdrawal thresholds were 1.58±0.28 g and 3.07±0.68 g ($P<0.001$). By day 22 post-treatment the withdrawal threshold for the control group was largely unchanged at 1.69±0.17 g whereas the GTX-01* withdrawal threshold for the GTX-01* group had further increased to 5.18±0.74 g ($P<0.001$). At the final time-point tested (35 days post-treatment) there was a small loss in the hypersensitivity to mechanical stimulation in the control group (2.53±0.40 g) whereas the GTX-01* group maintained the level of sensitivity to mechanical stimulation at close to normal levels (5.21±0.43 g) ($P<0.001$) (FIG. 13).

If the baseline data on day −1 represents normal or 100% analgesia and that on day 10 is given to represent 0% analgesia then the analgesic effect of GTX-01* at days 13, 22 and 35 post-treatment represents 33%, 77% and 77% of normal, respectively.

On day 46 post-surgery, gabapentin (100 mg/kg: IP) decreased the mechanical hypersensitivity in the animals that had previously been administered the "Control vector". The withdrawal threshold in those animals at pre-dose, 1 hour and 2 hours post dose was 2.46±0.49 g, 3.44±0.36 g ($P<0.01$) and 4.15±0.19 g ($P<0.001$), respectively (FIG. 14). Gabapentin had no effect on the near-normal response to mechanical stimulation in those animals previously treated with GTX-01* (FIG. 14).

Immunohistochemical evaluation of the DRG from the GTX-01*-treated animal harvested at day 22 post-treatment showed individual cell bodies that stained positive for EYFP (a product of the pFB-hSyn-GluCloptalpha-mEYFP-L9'A gene delivered by GTX-01*) (FIG. 15). Similarly, nerve endings situated beneath the dermis layer of the paw from the same animal stained positive for EYFP (FIG. 15). These data show that the virus was taken up by the nerve endings at the injected site, transported to the cell body in the DRG and that the gene product was successfully expressed in the nerve endings.

Conclusions

A single administration of GTX-01* produced a significant and long-lasting analgesic effect in the SNI model of chronic neuropathic pain in the rat.

Example 6

Purpose

The objective of this study was to determine whether monomeric expression of the Human Glycine Receptor subunit alpha 1, isoform a (hGlyRa1) in HEK-293 cells had an effect on cell viability.

Methods

Human embryonic kidney (HEK) 293 cells were purchased from ATCC (#CRL-1573). Cells were cultured in Dulbecco's modified Eagle's medium (DMEM; Gibco #11965) supplemented with 10% FBS (Gibco #26140), 100 units/ml penicillin, 100 µg/ml streptomycin (Gibco #15140), and 1 mM sodium pyruvate (Gibco #11360), and maintained at 37° C. and 5% $CO_2$ in a humidified incubator. Cells were passaged when confluent at a subcultivation ratio of 1:5 or 1:10 every 3 to 4 days. The cells were then plated at 20,000 cells/well, with a plating volume of 100 µl/well, in a clear 96-well culture plate. After 24 hours in culture the cells were either mock-transfected or were transfected with the hGlyRa1 (pFB-CMV-hGlyRa1-P2A-mEYFP-WT). For transfection, 16 μg total DNA in 750 μl Opti-MEM (Gibco 31985-070) was mixed with 30 μl ExpressFect in 750 μl Opti-MEM, pre-incubated for 20 minutes, and then added at 15 μl/well to cells containing 100 μl fresh culture media. Transfection mixes were removed from cultures following a 4-6 hour incubation period at 37° C./5% $CO_2$ and replaced with either fresh DMEM (containing 400 μM glycine) or fresh glycine-free, culture medium (Gibco 12360-038), supplemented with L-glutamine (Gibco 25030-081). Half of the untransfected, mock transfected and the transfected cells were cultured in DMEM (containing 400 μM glycine) while the other half were cultured in glycine-free media. After 72 hours, cell viability was measured using trypan blue dye exclusion as a marker of cell viability. Under a binocular microscope, the unstained (viable) and stained (non-viable) cells were counted separately. Five separate wells were evaluated for each condition.

Results

Untransfected cells in absence and presence of glycine had an average cell viability of 94.6% and 95.6% respectively. Mock-transfected cells had an average cell viability of 93.8% in the absence of glycine and 92.8% in the presence of glycine. Monomeric expression of hGlyRa1 did not affect cell viability either in the absence of glycine (92.0% of cells were viable) or in the presence of glycine which activates the monomeric chloride channel formed by the alpha subunits (94.0% of cells were viable) (FIG. 16).

Conclusion

Monomeric expression of the alpha subunit of the glycine receptor channel (hGlyRa1) and subsequent exposure to glycine for 72 hours in HEK-293 cells had no effect on cell viability.

Example 7

Purpose

The objective of this study was to determine whether monomeric expression of the L9'A mutation of the GluCl α-subunit in HEK-293 cells had any effect on cell viability.

Methods

Human embryonic kidney (HEK) 293 cells were purchased from ATCC (#CRL-1573). Cells were cultured in Dulbecco's modified Eagle's medium (DMEM; Gibco #11965) supplemented with 10% FBS (Gibco #26140), 100 units/ml penicillin, 100 μg/ml streptomycin (Gibco #15140), and 1 mM sodium pyruvate (Gibco #11360), and maintained at 37° C. and 5% $CO_2$ in a humidified incubator. Cells were passaged when confluent at a subcultivation ratio of 1:5 or 1:10 every 3 to 4 days. The cells were then plated at 20,000 cells/well, with a plating volume of 100 μl/well, in clear 96-well culture plates. After 24 hours in culture the cells were either mock-transfected or transfected with the α-subunit of either GluCl (pFB-CMV-GluCloptalpha-mEYFP-WT) or GluCl* (pFB-CMV-GluCloptalpha-mEYFP-L9'A). For transfection, 16 μg total DNA in 750 μl Opti-MEM (Gibco 31985-070) was mixed with 30 μl ExpressFect in 750 μl Opti-MEM, pre-incubated for 20 minutes, and then added at 15 μl/well to cells containing 100 μl fresh culture media. Transfection mixes were removed from cultures following a 4-6 hour incubation period at 37° C./5% $CO_2$ and replaced with fresh culture medium. After 48 hours, cell viability was measured using trypan blue dye exclusion as a marker of cell viability. Under a binocular microscope, the unstained (viable) and stained (non-viable) cells were counted separately. Five separate wells were evaluated for each condition (un-transfected, mock-transfected, GluCl and GluCl*).

Results

Untransfected and mock-transfected cells had an average cell viability of 94.8% and 92.8%, respectively. Monomeric expression of GluCl wild-type α-subunit did not affect cell viability (91.8% of cells were viable). Monomeric expression of the L9'A mutation of the GluCl alpha subunit which forms a constitutively active Cl⁻ channel (GluCl*) had no significant effect on cell viability (94.0% of cells were viable) (FIG. 17).

Conclusion

Monomeric expression of the L9'A mutation of the GluCl α-subunit in HEK-293 cells had no effect on cell viability.

Example 8

Purpose

To evaluate the effect of the GluCl receptor alpha subunit L9'A mutant and the glycine receptor alpha-1 subunit mutant (L9'A) on in free intracellular $Ca^{++}$ upon the addition of the muscarinic receptor agonist carbachol in human smooth muscle cells.

Methods

Human airway smooth muscle (HASM) cells were derived from tracheas obtained from the National Disease Research Interchange (Philadelphia, Pa., USA) and from the International Institute for the Advancement of Medicine (Edison, N.J., USA). The cells were cultured in Ham's F-12 medium supplemented with 10% FBS, 100 U mL⁻¹ penicillin, 0.1 mg mL⁻¹ streptomycin and 2.5 mg mL⁻¹ amphotericin B, and this medium was replaced every 72 h. HASM cells in subculture during passages 1-5 were used, because these cells retain the expression of native contractile protein. The HASM cells were derived from healthy normal donors.

GluCl Receptor

Cells were derived from the trachea of two individual donors (HSAM-N030116K/1 and N082715/3). They were grown to ~80% confluence then transfected with pFB-CMV-GluCloptalpha-mEYFP-L9'A (GluCl receptor alpha L9'A mutant) or no transfection for 72 hr. Cells were serum starved for 24 hr and loaded with Fluo 8 calcium sensing dye for 1 hr prior to stimulation with carbachol (10 μM). Separate wells were stimulated with formoterol (1 μM, 10 min) prior to stimulation with carbachol (10 μM). All incubations and stimulations in this study were done in tissue culture medium containing glycine.

Gly Receptor

Cells were derived from the trachea of two individual donors (HASM-N070112/3 and N082112/3) were grown to ~80% confluence then transfected with pFB-CMV-hGlyRa1-P2A-mEYFP-WT (wild-type GlyR alpha-1 subunit), pFB-CMV-hGlyRa1-P2A-mEYFP-L9'A (GlyR alpha-1 subunit L9'A), or no transfection for 72 hr. Cells were serum starved for 24 hr and loaded with Fluo 8 calcium sensing dye for 1 hr prior to stimulation with histamine. Cells transfected with pFB-CMV-hGlyRa1-P2A-mEYFP-WT were pre-incubated for 1 hr with glycine (100 μM or 1 mM) prior to stimulation with histamine (1 μM). No glycine was added to cells transfected with pFB-CMV-hGlyRa1-P2A-mEYFP-L9'A. All incubations and stimulations in this study were done in glycine-free Kreb's buffer. All data from both studies is expressed as relative fluorescent units.

Results

Results for the GluCl receptor are shown in FIG. 18A-B. Specifically, there was an increase in free intracellular $Ca^{++}$ upon the addition of the muscarinic receptor agonist carbachol. In cells N030116K/1 the response was very rapid and more gradual in cells from the second donor N082715/3. Formoterol (beta-adrenoceptor agonist and a known smooth muscle relaxant) antagonized the carbachol-induced increase in intracellular $Ca^{++}$. Cells transfected with the constitutively active GluCl alpha subunit L9'A mutation (pFB-CMV-GluCloptalpha-mEYFP-L9'A) also showed a reduction in the intracellular $Ca^{++}$ induced by carbachol. This was observed in cells from both donors. This observation is consistent with the observations of Frazier (2012) that this mutation generates a constitutively active chloride channel that leads to hyperpolarization of the cell, which in turn will attenuate the opening of voltage-dependent $Ca^{++}$ (L-type) channels thus decreasing the levels of intracellular $Ca^{++}$.

Results for the GlyR are shown in FIG. 19A-B. Specifically, there was an increase in free intracellular $Ca^{++}$ upon the addition of histamine. In cells N082112/3 the response was very rapid and more gradual in cells from donor N070112/3. In cells transfected with pFB-CMV-hGlyRa1-P2A-mEYFP-WT (wild-type GlyR alpha-1 subunit) in the presence of glycine (100 μm or 1 mM) the histamine-induced increase in intracellular Ca was antagonized. In cells from both donors transfected with pFB-CMV-hGlyRa1-P2A-mEYFP-L9'A (GlyR alpha-1 subunit L9'A) an equivalent antagonism of the histamine response was seen in the absence of glycine.

Conclusions

The observations for the GluCl alpha subunit L9'A mutant are consistent with the observations of Frazier (2012) that this mutation generates a constitutively active chloride channel that leads to hyperpolarization of the cell, which in turn will attenuate the opening of voltage-dependent $Ca^{++}$ (L-type) channels thus decreasing the levels of intracellular $Ca^{++}$.

These data regarding the GlyR are consistent with the hypothesis that the GlyR alpha-1 subunit L9'A forms a constitutively active chloride channel that leads to hyperpolarization of the cell, which in turn will attenuate the opening of voltage-dependent $Ca^{++}$ (L-type) channels thus decreasing the levels of intracellular $Ca^{++}$.

Example 9

Purpose

To evaluate the ability of AAV6 to transduce human neuronal cells in culture.

Methods

Under a dissection microscope, human dorsal root ganglia (hDRG) collected post-mortem from donors were cleaned of excess fat, connective tissue, and nerve roots. The ganglia were then sliced into small pieces. The pieces were digested in an enzyme cocktail of 0.25% Collagenase P and 0.1% Dispase I and incubated at 37° C. for 18 hours. Following digestion, the cells were washed free of the enzyme solution with Hanks balanced salt solution.

After purification, the dissociated cells were plated onto tissue culture dishes. Prior to plating the dishes were treated with 10 μg/ml poly-L-lysine and Type 1 rat-tail collagen. Cells were maintained in Neurobasal-A medium (Invitrogen) supplemented with B-27 Supplement (Invitrogen), 1% penicillin/streptomycin, 0.4 mM L-glutamine, 2.5 g/L glucose and 1% fetal bovine serum Once the cultured cells had stabilized (4-5 days) they were transduced with AAV6-hSyn-GFP was added to the cells at a concentration of 2.2e11 vg/mL and left in contact with the cells for a minimum of 6 hours. The cells were examined every 2-3 days under fluorescence microscope to check for GFP expression. Observations were recorded by means of digital images.

Results

At 4 days post-exposure to the AAV6 neuronal cells showed strong expression of GFP protein (FIG. 20). The expression of GFP was not visible in all neuronal cells which is consistent with previous studies in mice that show that AAV6 shows selectivity for small nociceptive neurons (Towne C. et al. (2009) Molecular Pain 5(1): 52). Glial cells did not express GFP either. This level of selectivity may be in part due to AAV6 tropism and is certainly influenced by the use of the hSyn promoter which allows for neuron-selective expression of the GFP.

Conclusion

These data show that AAV6 is capable of transducing human neuronal cells in culture. This observation suggests that, as demonstrated in rodents, AAV6 when injected into the periphery will transduce nociceptive neurons in the region of the injection and is capable of delivering genes that can affect the physiology of those neurons. These observations are consistent with the concept of using AAV6 to deliver an endogenously-activated or constitutively active chloride channel to peripheral nociceptive neurons, to prevent the transmission of pain signals from the periphery to the spinal cord in humans.

Incorporated by reference are all references, including publications, patent applications, and patents, cited herein to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of treating pain in a human in need thereof, comprising administering to the human an effective amount of an adeno-associated virus (AAV) vector comprising an expression cassette,
   wherein the expression cassette comprises a human synapsin-1 (hSyn) promoter operably linked to a nucleic acid encoding a human alpha-1-subunit of the glycine receptor (hGlyRa1),
   wherein the hGlyRa1 subunit is expressed and multimerizes with additional subunits to form a functional glycine receptor (GlyR),
   wherein activation of the functional GlyR comprising the hGlyRa1 subunit by an endogenous agonist results in a pain treatment, and
   wherein the method does not include administering a GlyR agonist to the human.

2. The method of claim 1, wherein the encoded hGlyRa1 subunit has at least 80% sequence identity to a wildtype hGlyRa1 subunit.

3. The method of claim 1, wherein the encoded hGlyRa1 subunit has at least 90% sequence identity to a wildtype hGlyRa1 subunit.

4. The method of claim 1, wherein the encoded hGlyRa1 subunit is a wildtype hGlyRa1 subunit.

5. The method of claim 1, wherein the AAV vector is an AAV vector selected from the group consisting of AAV1, AAV2, AAV3, AAV5, AAV6, AAVS8, AAV9, rAAV2/6 and scAAV2 vector.

6. The method of claim 5, wherein the AAV vector is an AAV6 vector.

7. The method of claim 5, wherein the AAV vector is a scAAV vector.

8. The method of claim 5, wherein the AAV vector is an AAV2 vector.

9. The method of claim 5, wherein the AAV vector is an AAV9 vector.

10. The method of claim 5, wherein the AAV vector is an rAAV2/6 vector.

11. The method of claim 1, wherein the AAV vector has tropism for peripheral neurons.

12. The method of claim 1, wherein the AAV vector has tropism for sensory neurons.

13. The method of claim 1, wherein the AAV vector has tropism for nociceptive neurons.

14. The method of claim 1, further comprising administering to the human one or more other therapeutic agents, wherein the one or more other therapeutic agents is not a glycine receptor agonist.

15. The method of claim 1, wherein the encoded hGlyRa1 subunit has at least 90% sequence identity to SEQ ID NO: 3.

16. The method of claim 1, wherein the encoded hGlyRa1 subunit has at least 95% sequence identity to SEQ ID NO:3.

17. The method of claim 1, wherein the nucleic acid encoding an hGlyRa1 subunit comprises a sequence having at least 90% sequence identity to SEQ ID NO:1.

18. The method of claim 1, wherein the nucleic acid encoding an hGlyRa1 subunit comprises a sequence having at least 95% sequence identity to SEQ ID NO:1.

19. The method of claim 1, wherein the encoded hGlyRa1 subunit has 99% sequence identity to SEQ ID NO:3.

20. The method of claim 1, wherein the encoded hGlyRa1 subunit comprises SEQ ID NO:3.

21. The method of claim 1, wherein the nucleic acid encoding an hGlyRa1 subunit comprises SEQ ID NO:1.

22. The method of claim 1, wherein the AAV vector infects a peripheral neuron.

23. The method of claim 1, wherein the AAV vector infects a sensory neuron.

24. The method of claim 1, wherein the AAV vector infects a nociceptive neuron.

25. The method of claim 1, wherein the pain is chronic pain.

26. The method of claim 1, wherein the pain is joint pain.

27. The method of claim 1, wherein the pain is neuropathic pain.

* * * * *

```
                         SEQUENCE LISTING

<160> NUMBER OF SEQ ID NOS: 15

<210> SEQ ID NO 1
<211> LENGTH: 1374
<212> TYPE: DNA
<213> ORGANISM: Homo sapiens

<400> SEQUENCE: 1
atgtacagct tcaatactct tcgactctac ctttgggaga ccattgtatt cttcagcctt      60
gctgcttcta aggaggctga agctgctcgc tccgcaccca agcctatgtc accctcggat     120
ttcctggata agctaatggg gagaacctcc ggatatgatg ccaggatcag gcccaatttt     180
aaaggtcccc cagtgaacgt gagctgcaac attttcatca acagctttgg ttccattgct     240
gagacaacca tggactatag ggtcaacatc ttcctgcggc agcaatggaa cgaccccgc      300 ctggcctata atgaatacc tgacgactct ctggacctgg acccatccat gctggactcc     360
atctggaaac ctgacctgtt ctttgccaac gagaagggg cccacttcca tgagatcacc      420
acagacaaca aattgctaag gatctcccgg aatgggaatg tcctctacag catcagaatc     480
accctgacac tggcctgccc catggacttg aagaatttcc ccatggatgt ccagacatgt     540
atcatgcaac tggaaagctt tggatatacg atgaatgacc tcatctttga gtggcaggaa     600
cagggagccg tgcaggtagc agatggacta actctgcccc agtttatctt gaaggaagag     660
aaggacttga gatactgcac caagcactac aacacaggta aattcacctg cattgaggcc     720
cggttccacc tggagcggca gatgggttac tacctgattc agatgtatat tcccagcctg     780
ctcattgtca tcctctcatg gatctccttc tggatcaaca tggatgctgc acctgctcgt     840
gtgggcctag gcatcaccac tgtgctcacc atgaccaccc agagctccgg ctctcgagca     900
tctctgccca aggtgtccta tgtgaaagcc attgacattt ggatggcagt ttgcctgctc     960
tttgtgttct cagccctatt agaatatgct gccgttaact ttgtgtctcg gcaacataag    1020
gagctgctcc gattcaggag gaagcggaga catcacaaga gccccatgtt gaatctattc    1080
caggaggatg aagctggaga aggccgcttt aacttctctg cctatgggat gggcccagcc    1140
tgtctacagg ccaaggatgg catctcagtc aagggcgcca acaacagtaa caccaccaac    1200 cccctcctg caccatctaa gtccccagag gagatgcgaa aactcttcat ccagagggcc     1260
aagaagatcg acaaaatatc ccgcattggc ttccccatgg ccttcctcat tttcaacatg    1320
ttctactgga tcatctacaa gattgtccgt agagaggacg tccacaacca gtga          1374

<210> SEQ ID NO 2
<211> LENGTH: 1374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atgtacagct tcaatactct tcgactctac ctttgggaga ccattgtatt cttcagcctt      60
gctgcttcta aggaggctga agctgctcgc tccgcaccca agcctatgtc accctcggat     120
ttcctggata agctaatggg gagaacctcc ggatatgatg ccaggatcag gcccaatttt     180
aaaggtcccc cagtgaacgt gagctgcaac attttcatca acagctttgg ttccattgct     240
```

```
gagacaacca tggactatag ggtcaacatc ttcctgcggc agcaatggaa cgacccccgc    300
ctggcctata atgaataccc tgacgactct ctggacctgg acccatccat gctggactcc    360
atctggaaac ctgacctgtt ctttgccaac gagaaggggg cccacttcca tgagatcacc    420
acagacaaca aattgctaag gatctcccgg aatgggaatg tcctctacag catcagaatc    480
accctgacac tggcctgccc catggacttg aagaatttcc ccatggatgt ccagacatgt    540
atcatgcaac tggaaagctt tggatatacg atgaatgacc tcatctttga gtggcaggaa    600
cagggagccg tgcaggtagc agatggacta actctgcccc agtttatctt gaaggaagag    660
aaggacttga gatactgcac caagcactac aacacaggta aattcacctg cattgaggcc    720
cggttccacc tggagcggca gatgggttac tacctgattc agatgtatat tcccagcctg    780
ctcattgtca tcctctcatg gatctccttc tggatcaaca tggatgctgc acctgctcgt    840
gtgggcctag gcatcaccac tgtggccacc atgaccaccc agagctccgg ctctcgagca    900
tctctgccca aggtgtccta tgtgaaagcc attgacattt ggatggcagt ttgcctgctc    960
tttgtgttct cagccctatt agaatatgct gccgttaact ttgtgtctcg caacataag   1020 gagctgctcc gattcaggag gaagcggaga catcacaaga gccccatgtt gaatctattc   1080
caggaggatg aagctggaga aggccgcttt aacttctctg cctatgggat gggcccagcc   1140
tgtctacagg ccaaggatgg catctcagtc aagggcgcca acaacagtaa caccaccaac   1200 cccctcctg caccatctaa gtccccagag gagatgcgaa aactcttcat ccagagggcc   1260
aagaagatcg acaaaatatc ccgcattggc ttccccatgg ccttcctcat tttcaacatg   1320
ttctactgga tcatctacaa gattgtccgt agagaggacg tccacaacca gtga         1374

<210> SEQ ID NO 3
<211> LENGTH: 457
<212> TYPE: PRT
<213> ORGANISM: Homo sapiens

<400> SEQUENCE: 3

Met Tyr Ser Phe Asn Thr Leu Arg Leu Tyr Leu Trp Glu Thr Ile Val
1               5                   10                  15

Phe Phe Ser Leu Ala Ala Ser Lys Glu Ala Glu Ala Ala Arg Ser Ala
                20                  25                  30

Pro Lys Pro Met Ser Pro Ser Asp Phe Leu Asp Lys Leu Met Gly Arg
            35                  40                  45

Thr Ser Gly Tyr Asp Ala Arg Ile Arg Pro Asn Phe Lys Gly Pro Pro
        50                  55                  60

Val Asn Val Ser Cys Asn Ile Phe Ile Asn Ser Phe Gly Ser Ile Ala
65                  70                  75                  80

Glu Thr Thr Met Asp Tyr Arg Val Asn Ile Phe Leu Arg Gln Gln Trp
                85                  90                  95

Asn Asp Pro Arg Leu Ala Tyr Asn Glu Tyr Pro Asp Asp Ser Leu Asp
            100                 105                 110

Leu Asp Pro Ser Met Leu Asp Ser Ile Trp Lys Pro Asp Leu Phe Phe
        115                 120                 125

Ala Asn Glu Lys Gly Ala His Phe His Glu Ile Thr Thr Asp Asn Lys
    130                 135                 140

Leu Leu Arg Ile Ser Arg Asn Gly Asn Val Leu Tyr Ser Ile Arg Ile
145                 150                 155                 160

Thr Leu Thr Leu Ala Cys Pro Met Asp Leu Lys Asn Phe Pro Met Asp
                165                 170                 175
```

Val Gln Thr Cys Ile Met Gln Leu Glu Ser Phe Gly Tyr Thr Met Asn
            180                 185                 190

Asp Leu Ile Phe Glu Trp Gln Gln Gly Ala Val Gln Val Ala Asp
        195                 200                 205

Gly Leu Thr Leu Pro Gln Phe Ile Leu Lys Glu Lys Asp Leu Arg
    210                 215                 220

Tyr Cys Thr Lys His Tyr Asn Thr Gly Lys Phe Thr Cys Ile Glu Ala
225                 230                 235                 240

Arg Phe His Leu Glu Arg Gln Met Gly Tyr Tyr Leu Ile Gln Met Tyr
                245                 250                 255

Ile Pro Ser Leu Leu Ile Val Ile Leu Ser Trp Ile Ser Phe Trp Ile
            260                 265                 270

Asn Met Asp Ala Ala Pro Ala Arg Val Gly Leu Gly Ile Thr Thr Val
            275                 280                 285

Leu Thr Met Thr Thr Gln Ser Ser Gly Ser Arg Ala Ser Leu Pro Lys
        290                 295                 300

Val Ser Tyr Val Lys Ala Ile Asp Ile Trp Met Ala Val Cys Leu Leu
305                 310                 315                 320

Phe Val Phe Ser Ala Leu Leu Glu Tyr Ala Ala Val Asn Phe Val Ser
                325                 330                 335

Arg Gln His Lys Glu Leu Leu Arg Phe Arg Arg Lys Arg Arg His His
            340                 345                 350

Lys Ser Pro Met Leu Asn Leu Phe Gln Glu Asp Glu Ala Gly Glu Gly
        355                 360                 365

Arg Phe Asn Phe Ser Ala Tyr Gly Met Gly Pro Ala Cys Leu Gln Ala
        370                 375                 380

Lys Asp Gly Ile Ser Val Lys Gly Ala Asn Asn Ser Asn Thr Thr Asn
385                 390                 395                 400

Pro Pro Pro Ala Pro Ser Lys Ser Pro Glu Glu Met Arg Lys Leu Phe
                405                 410                 415

Ile Gln Arg Ala Lys Lys Ile Asp Lys Ile Ser Arg Ile Gly Phe Pro
            420                 425                 430

Met Ala Phe Leu Ile Phe Asn Met Phe Tyr Trp Ile Ile Tyr Lys Ile
            435                 440                 445

Val Arg Arg Glu Asp Val His Asn Gln
    450                 455

<210> SEQ ID NO 4
<211> LENGTH: 21
<212> TYPE: PRT
<213> ORGANISM: Homo sapiens

<400> SEQUENCE: 4

Pro Ala Arg Val Gly Leu Gly Ile Thr Thr Val Leu Thr Met Thr Thr
1               5                   10                  15

Gln Ser Ser Gly Ser
            20

<210> SEQ ID NO 5
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Met Tyr Ser Phe Asn Thr Leu Arg Leu Tyr Leu Trp Glu Thr Ile Val
1               5                   10                  15

Phe Phe Ser Leu Ala Ala Ser Lys Glu Ala Glu Ala Ala Arg Ser Ala
                20                  25                  30

Pro Lys Pro Met Ser Pro Ser Asp Phe Leu Asp Lys Leu Met Gly Arg
            35                  40                  45

Thr Ser Gly Tyr Asp Ala Arg Ile Arg Pro Asn Phe Lys Gly Pro Pro
        50                  55                  60

Val Asn Val Ser Cys Asn Ile Phe Ile Asn Ser Phe Gly Ser Ile Ala
65                  70                  75                  80

Glu Thr Thr Met Asp Tyr Arg Val Asn Ile Phe Leu Arg Gln Gln Trp
                85                  90                  95

Asn Asp Pro Arg Leu Ala Tyr Asn Glu Tyr Pro Asp Asp Ser Leu Asp
            100                 105                 110

Leu Asp Pro Ser Met Leu Asp Ser Ile Trp Lys Pro Asp Leu Phe Phe
        115                 120                 125

Ala Asn Glu Lys Gly Ala His Phe His Glu Ile Thr Thr Asp Asn Lys
        130                 135                 140

Leu Leu Arg Ile Ser Arg Asn Gly Asn Val Leu Tyr Ser Ile Arg Ile
145                 150                 155                 160

Thr Leu Thr Leu Ala Cys Pro Met Asp Leu Lys Asn Phe Pro Met Asp
                165                 170                 175

Val Gln Thr Cys Ile Met Gln Leu Glu Ser Phe Gly Tyr Thr Met Asn
            180                 185                 190

Asp Leu Ile Phe Glu Trp Gln Glu Gln Gly Ala Val Gln Val Ala Asp
        195                 200                 205

Gly Leu Thr Leu Pro Gln Phe Ile Leu Lys Glu Glu Lys Asp Leu Arg
    210                 215                 220

Tyr Cys Thr Lys His Tyr Asn Thr Gly Lys Phe Thr Cys Ile Glu Ala
225                 230                 235                 240

Arg Phe His Leu Glu Arg Gln Met Gly Tyr Tyr Leu Ile Gln Met Tyr
                245                 250                 255

Ile Pro Ser Leu Leu Ile Val Ile Leu Ser Trp Ile Ser Phe Trp Ile
            260                 265                 270

Asn Met Asp Ala Ala Pro Ala Arg Val Gly Leu Gly Ile Thr Thr Val
        275                 280                 285

Ala Thr Met Thr Thr Gln Ser Ser Gly Ser Arg Ala Ser Leu Pro Lys
    290                 295                 300

Val Ser Tyr Val Lys Ala Ile Asp Ile Trp Met Ala Val Cys Leu Leu
305                 310                 315                 320

Phe Val Phe Ser Ala Leu Leu Glu Tyr Ala Ala Val Asn Phe Val Ser
                325                 330                 335

Arg Gln His Lys Glu Leu Leu Arg Phe Arg Arg Lys Arg Arg His His
            340                 345                 350

Lys Ser Pro Met Leu Asn Leu Phe Gln Glu Asp Glu Ala Gly Glu Gly
        355                 360                 365

Arg Phe Asn Phe Ser Ala Tyr Gly Met Gly Pro Ala Cys Leu Gln Ala
    370                 375                 380

Lys Asp Gly Ile Ser Val Lys Gly Ala Asn Asn Ser Asn Thr Thr Asn
385                 390                 395                 400

Pro Pro Pro Ala Pro Ser Lys Ser Pro Glu Glu Met Arg Lys Leu Phe
                405                 410                 415
```

Ile Gln Arg Ala Lys Lys Ile Asp Lys Ile Ser Arg Ile Gly Phe Pro
            420                 425                 430

Met Ala Phe Leu Ile Phe Asn Met Phe Tyr Trp Ile Ile Tyr Lys Ile
        435                 440                 445

Val Arg Arg Glu Asp Val His Asn Gln
    450                 455

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Pro Ala Arg Val Gly Leu Gly Ile Thr Thr Val Ala Thr Met Thr Thr
1               5                   10                  15

Gln Ser Ser Gly Ser
            20

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(23)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 7
ccctgggcgt gaccaccctg nnnac                                       25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(23)
<223> OTHER INFORMATION: a, c, t, g, unknown or other
<220> FEATURE:
<223> OTHER INFORMATION: See specification as filed for detailed
      description of substitutions and preferred embodiments

<400> SEQUENCE: 8
gcggactgag cggtcatggt nnnca                                       25

<210> SEQ ID NO 9
<211> LENGTH: 21
<212> TYPE: PRT
<213> ORGANISM: Unknown
<220> FEATURE:
<223> OTHER INFORMATION: Description of Unknown:
      helical pore-lining M2 domain peptide

<400> SEQUENCE: 9

Gly Glu Arg Val Ser Phe Lys Ile Thr Leu Leu Leu Gly Tyr Ser Val
1               5                   10                  15

```
Phe Leu Ile Ile Val
            20

<210> SEQ ID NO 10
<211> LENGTH: 21
<212> TYPE: PRT
<213> ORGANISM: Unknown
<220> FEATURE:
<223> OTHER INFORMATION: Description of Unknown:
      helical pore-lining M2 domain peptide

<400> SEQUENCE: 10

Gly Glu Lys Met Thr Leu Ser Ile Ser Val Leu Leu Ser Leu Thr Val
1               5                   10                  15

Phe Leu Leu Val Ile
            20

<210> SEQ ID NO 11
<211> LENGTH: 21
<212> TYPE: PRT
<213> ORGANISM: Unknown
<220> FEATURE:
<223> OTHER INFORMATION: Description of Unknown:
      helical pore-lining M2 domain peptide

<400> SEQUENCE: 11

Gly Glu Lys Ile Thr Leu Cys Ile Ser Val Leu Leu Ser Leu Thr Val
1               5                   10                  15

Phe Leu Leu Leu Ile
            20

<210> SEQ ID NO 12
<211> LENGTH: 21
<212> TYPE: PRT
<213> ORGANISM: Unknown
<220> FEATURE:
<223> OTHER INFORMATION: Description of Unknown:
      helical pore-lining M2 domain peptide

<400> SEQUENCE: 12

Gly Glu Lys Ile Ser Leu Gly Ile Thr Val Leu Leu Ser Leu Thr Val
1               5                   10                  15

Phe Met Leu Leu Val
            20

<210> SEQ ID NO 13
<211> LENGTH: 21
<212> TYPE: PRT
<213> ORGANISM: Unknown
<220> FEATURE:
<223> OTHER INFORMATION: Description of Unknown:
      helical pore-lining M2 domain peptide

<400> SEQUENCE: 13

Pro Ala Arg Thr Val Phe Gly Val Thr Thr Val Leu Thr Met Thr Thr
1               5                   10                  15

Leu Ser Ile Ser Ala
            20

<210> SEQ ID NO 14
<211> LENGTH: 21
<212> TYPE: PRT
<213> ORGANISM: Unknown
<220> FEATURE:
<223> OTHER INFORMATION: Description of Unknown:
```

```
                helical pore-lining M2 domain peptide

<400> SEQUENCE: 14

Pro Ala Arg Val Thr Leu Gly Val Thr Thr Leu Leu Thr Met Thr Ala
1               5                   10                  15

Gln Ser Ala Gly Ile
            20

<210> SEQ ID NO 15
<211> LENGTH: 21
<212> TYPE: PRT
<213> ORGANISM: Unknown
<220> FEATURE:
<223> OTHER INFORMATION: Description of Unknown:
      helical pore-lining M2 domain peptide

<400> SEQUENCE: 15

Ala Gly Arg Val Ala Leu Gly Val Thr Thr Leu Leu Thr Met Thr Thr
1               5                   10                  15

Met Gln Ser Ala Ile
            20
```